United States Patent
Santagata et al.

(10) Patent No.: US 9,696,313 B2
(45) Date of Patent: Jul. 4, 2017

(54) HSF1 AS A MARKER IN TUMOR PROGNOSIS AND TREATMENT

(71) Applicants: WHITEHEAD INSTITUTE FOR BIO-MEDICAL RESEARCH, Cambridge, MA (US); THE BRIGHAM AND WOMEN'S HOSPITAL, INC., Boston, MA (US)

(72) Inventors: Sandro Santagata, Jamaica Plain, MA (US); Susan Lindquist, Chestnut Hill, MA (US); Luke J. Whitesell, Somerville, MA (US); Tan A. Ince, Miami, FL (US)

(73) Assignees: Whitehead Institute for Biomedical Research, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 209 days.

(21) Appl. No.: 14/350,328

(22) PCT Filed: Oct. 5, 2012

(86) PCT No.: PCT/US2012/059086
§ 371 (c)(1),
(2) Date: Apr. 7, 2014

(87) PCT Pub. No.: WO2013/052888
PCT Pub. Date: Apr. 11, 2013

(65) Prior Publication Data
US 2014/0234858 A1 Aug. 21, 2014

Related U.S. Application Data

(60) Provisional application No. 61/544,216, filed on Oct. 6, 2011.

(51) Int. Cl.
  *C07K 14/47* (2006.01)
  *G01N 33/574* (2006.01)
  *C12Q 1/68* (2006.01)

(52) U.S. Cl.
  CPC ..... *G01N 33/57496* (2013.01); *C12Q 1/6886* (2013.01); *G01N 33/57484* (2013.01); *C12Q 2600/112* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

FOREIGN PATENT DOCUMENTS

WO  WO 2011022440 A2 * 2/2011 .......... C07D 239/47

OTHER PUBLICATIONS

Ciocca et al. ("Ciocca", Cell Stress and chaperones, 2005, 10, 86.*
Rawat et al. ("Rawat", BMC Nucl. Acids Res, 2011, 39m 5879-5892 published online Apr. 1, 2011).*
Santagata (2011, PNAS, 108, 18378-18283).*
Ciocca, et al., "Heat shock proteins in cancer: diagnostic, prognostic, predictive, and treatment implications", *Cell Stress & Chaperones*, 10(2); 86-103(2005).
De Thonel, et al., Implication of heat shock factors in tumorigenesis therapeutical potential, *Cancer*, 3; 1158-1181 (2011).
Hoang, et al., "A novel association between the human heat shock transcription factor 1 (HSF1 and prosate adenocarcinoma", *Am J Pathol.*, 156(3); 857-864 (2000).
Hui, et al., "Induction of HSF1 expression is associated with sporadic colorectal cancer", *World J. Gastroenterol*, 10(21); 3122-3126 (2004).
Ince, Tan, Abstract, Epigenetic Regulation of Normal and Transformed Breast Epithelial Cell Phenotype, Department of Defense, Grant No. W81XWH-08-1-0282 (Funding Start date 2008).
Min, et al., "Selective suppression of lymphomas by functional loss of Hsf1 in a p53-deficient mouse model for spontaneous tumors", *Oncogen*, 26; 5086-5097 (2007).
Santagata, Sandro, Abstract, Heat Shock Directed Drug Discovery for the Treatment of Gliomas, National Institutes of Health, Grant No. 1K08NS064168 (Funding Start date Sep. 1, 2008).
Taipale, et al., HSP90 at the Hub of Protein Homeostasis: Emerging Mechanistic Insights. *Nature Reviews Molecular Cell Biology*, 11(7): 515-528 (2010).
Tang, et al., "Expression of heat shock proteins and heat shock protein messenger ribonucleic acid in human prostate carcinoma in vitro and in tumors in vivo", *Cell Stress & Chaperones*, 10(1); 46-58 (2005).
Whitesell, et al., Inhibiting the transcription factor HSF1 as an anticancer strategy, *Expert Opin. Ther. Targets*, 13(4) 469-478 (2009).

(Continued)

*Primary Examiner* — Misook Yu
*Assistant Examiner* — Kauser Akhoon
(74) *Attorney, Agent, or Firm* — Lisa M. Warren, Esq.; Morse, Barnes-Brown & Pendleton, P.C.

(57) ABSTRACT

In some aspects, the invention relates to Heat Shock Protein-1 (HSF1) gene and HSF1 gene products. In some aspects, the invention provides methods of tumor diagnosis, prognosis, treatment-specific prediction, or treatment selection, the methods comprising assessing the level of HSF1 expression or HSF1 activation in a sample obtained from the tumor. In some aspects, the invention relates to the discovery that increased HSF1 expression and increased HSF1 activation correlate with poor outcome in cancer, e.g., breast cancer.

17 Claims, 12 Drawing Sheets
(11 of 12 Drawing Sheet(s) Filed in Color)

(56) References Cited

OTHER PUBLICATIONS

Young, Richard, Abstract Epigenomic Mapping in Human Tumor Stem Cells, National Cancer Institute, Grant No. R01-CA146445-01 (Funding Start Date Aug. 21, 2009).

International Search Report for International Application PCT/US2012/059086, dated Jan. 24, 2013.

* cited by examiner

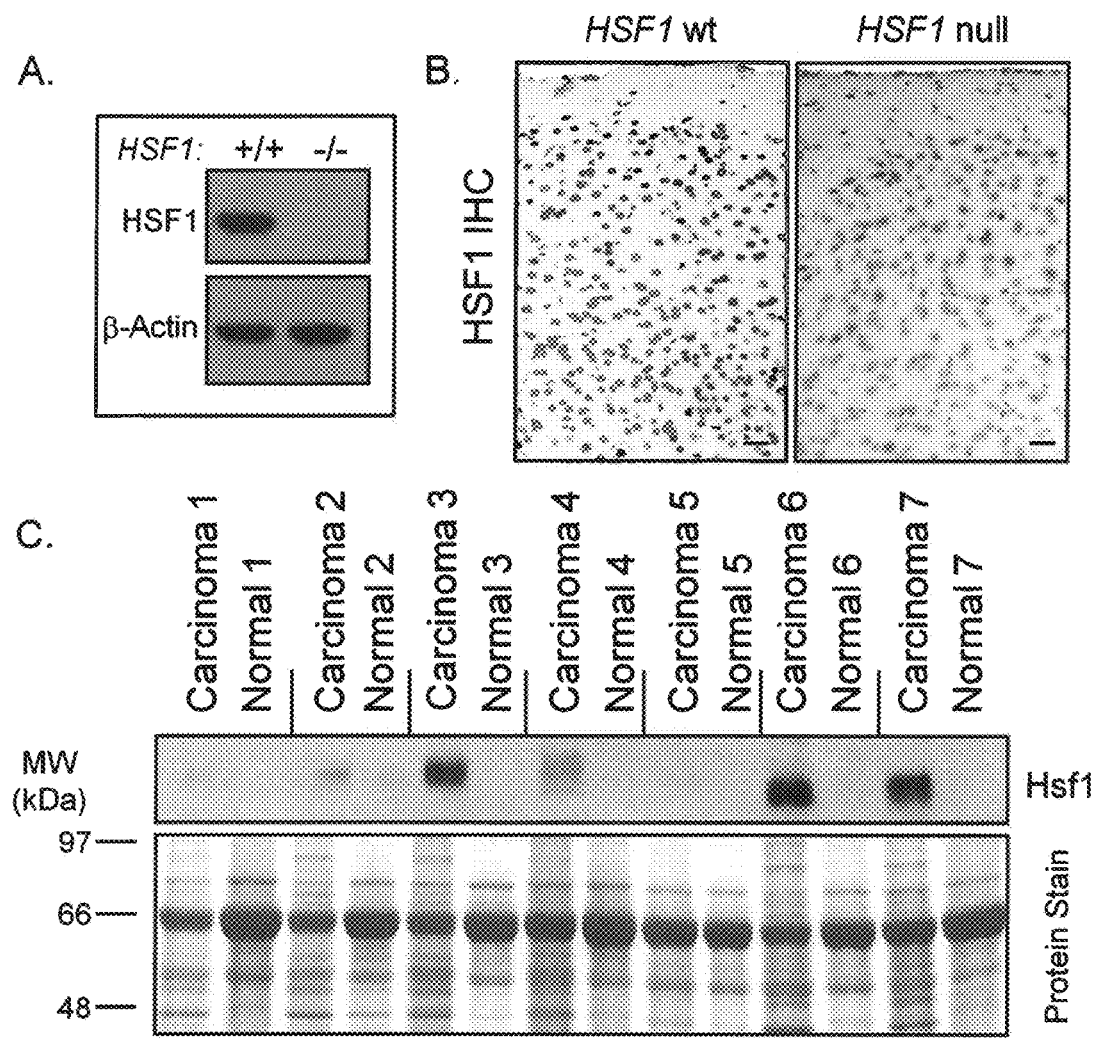
Figure 1. HSF1 protein is increased in breast cancer.

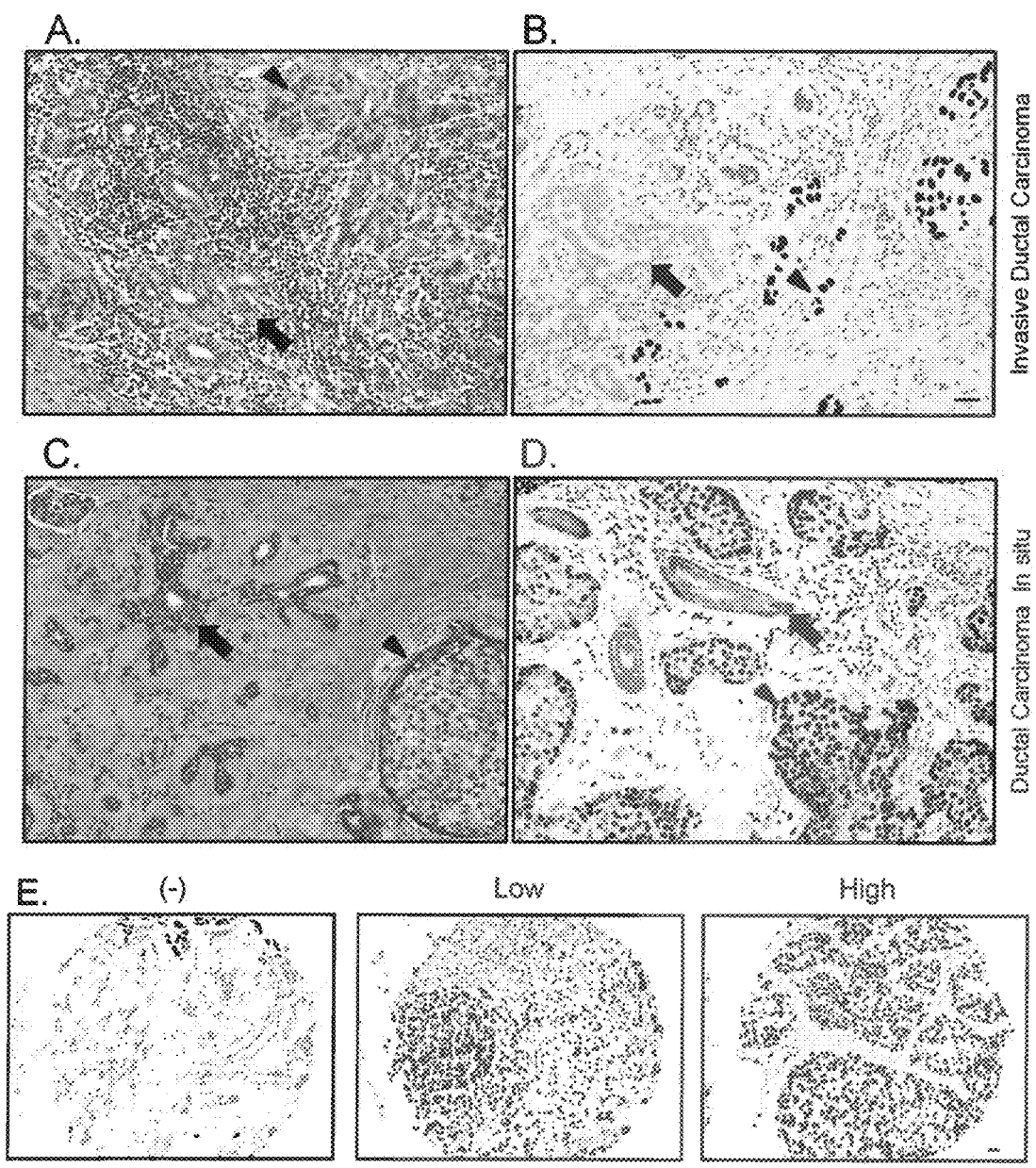
Figure 2. HSF1 is increased and localized to the nucleus in invasive and *in situ* breast carcinoma.

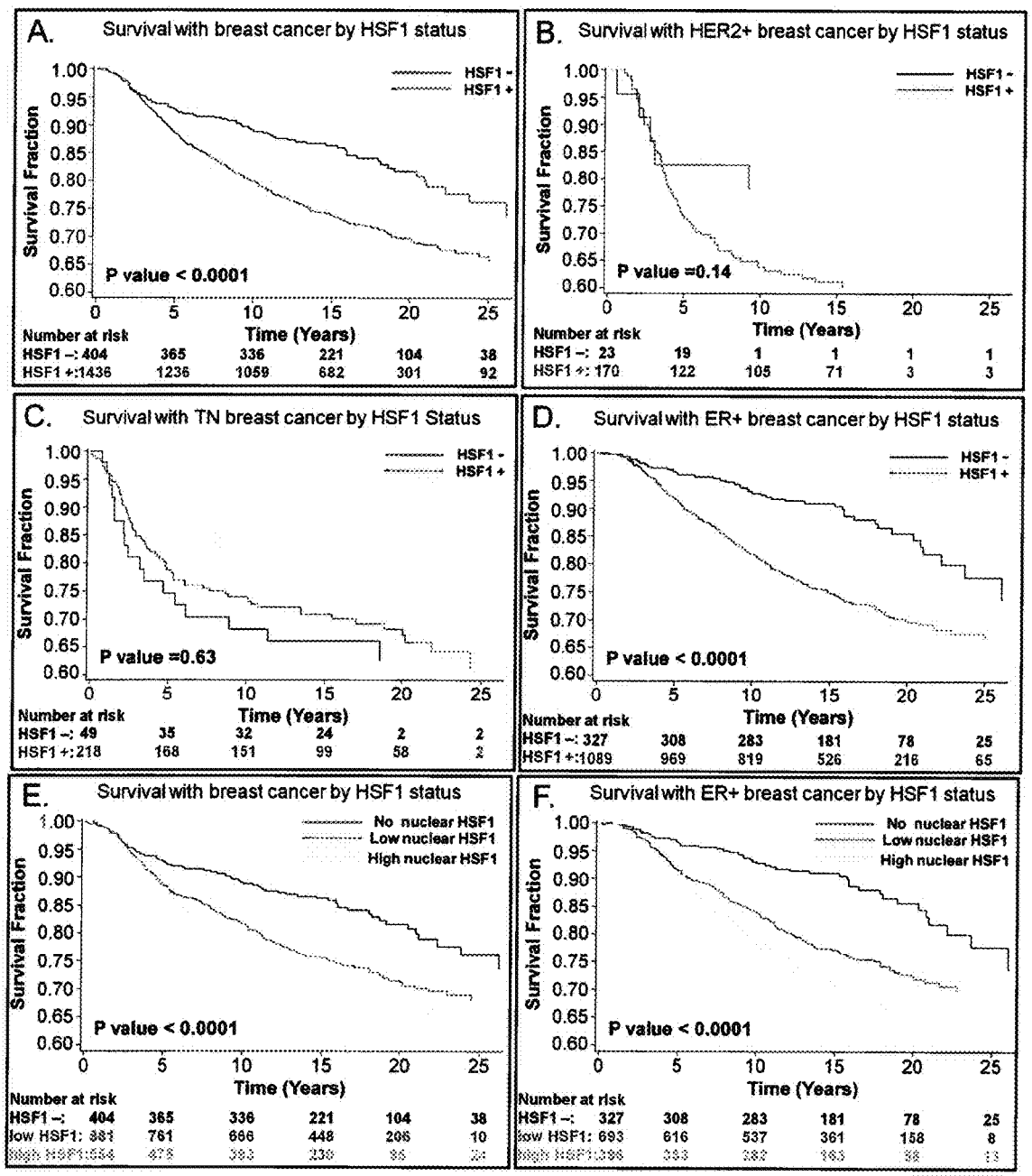
Figure 3. HSF1 positive tumors are associated with decreased survival in estrogen receptor-positive breast cancer.

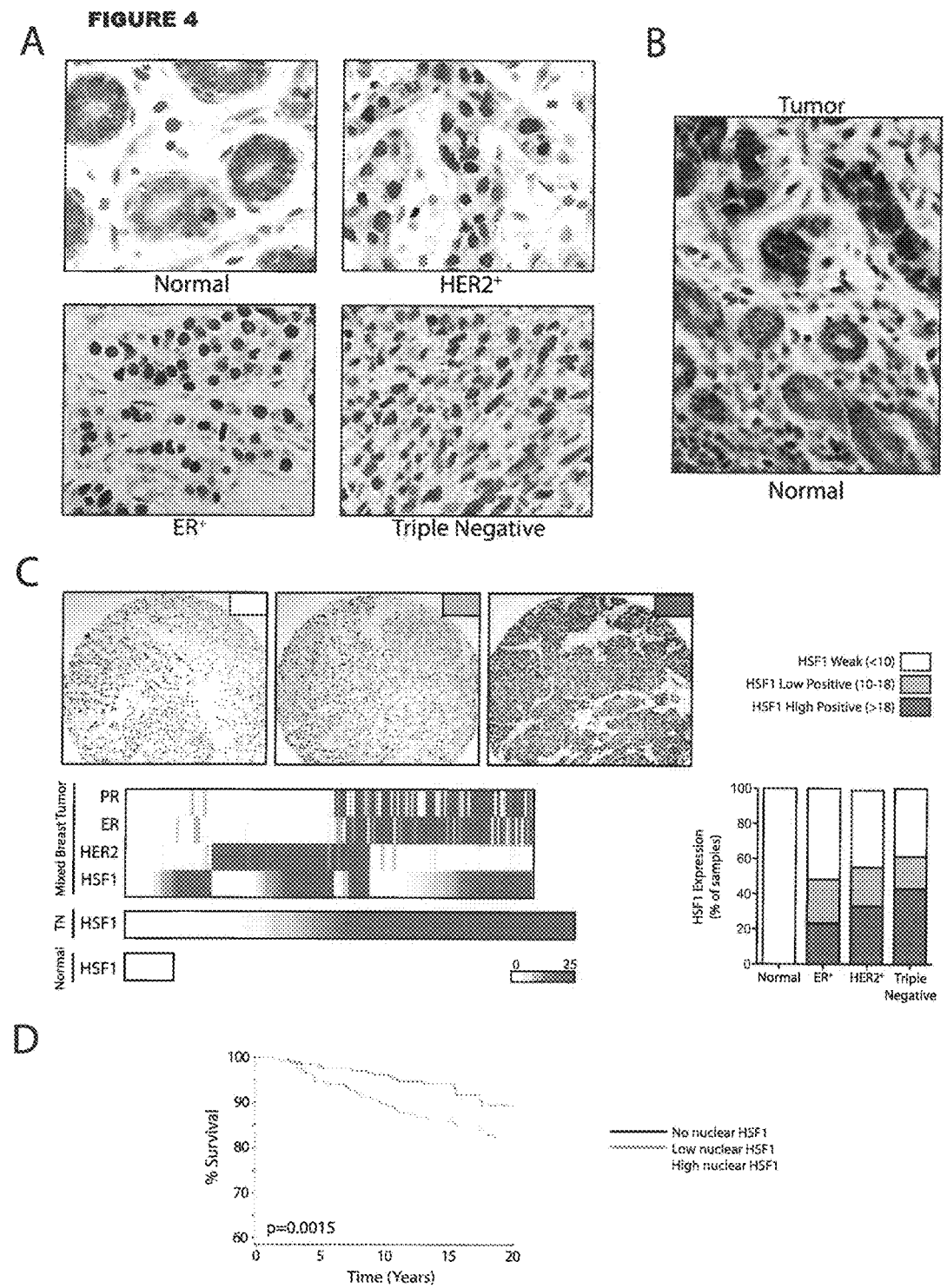

FIGURE 8
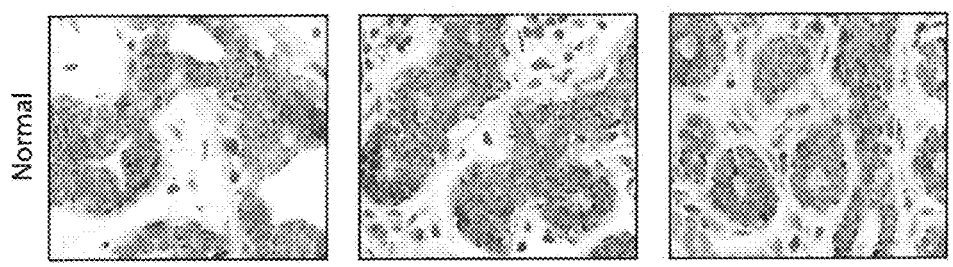
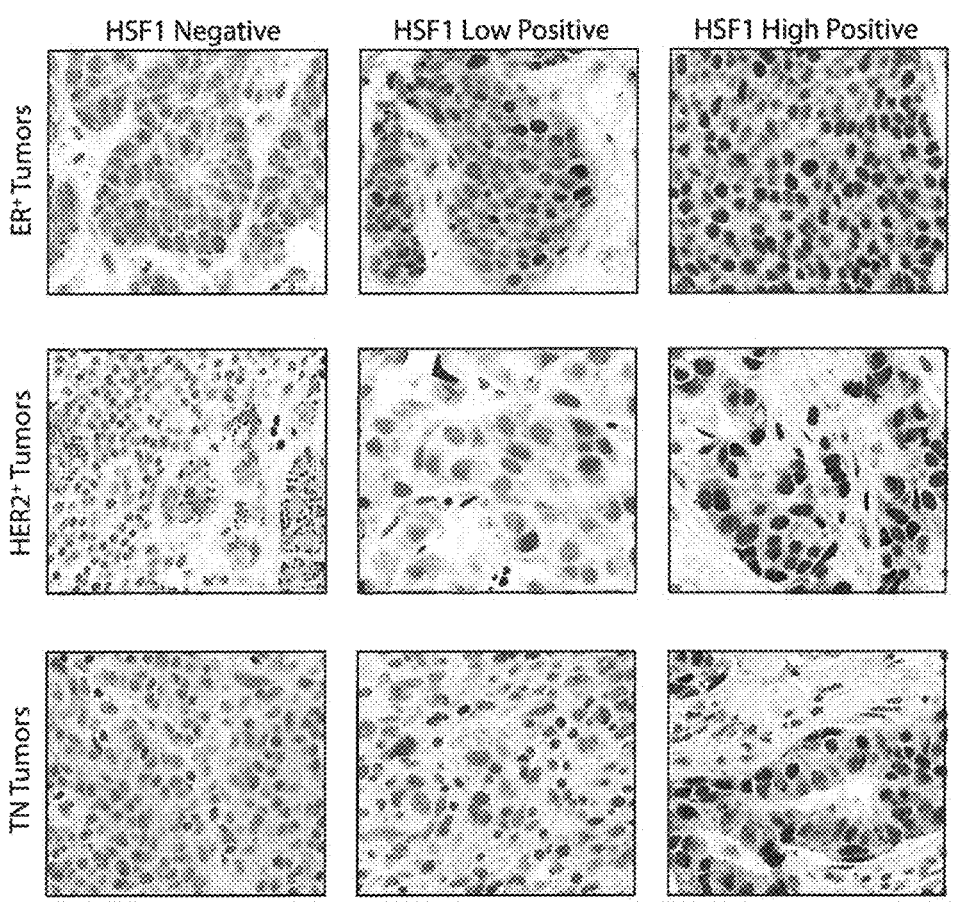

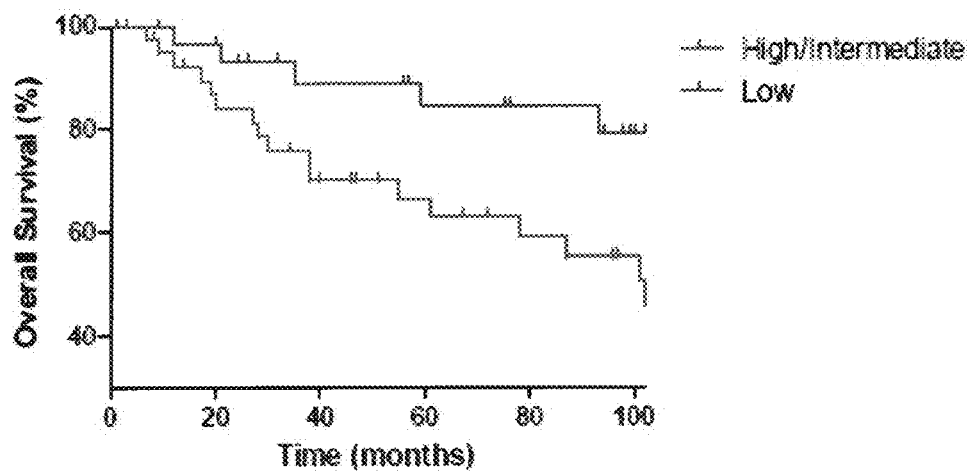
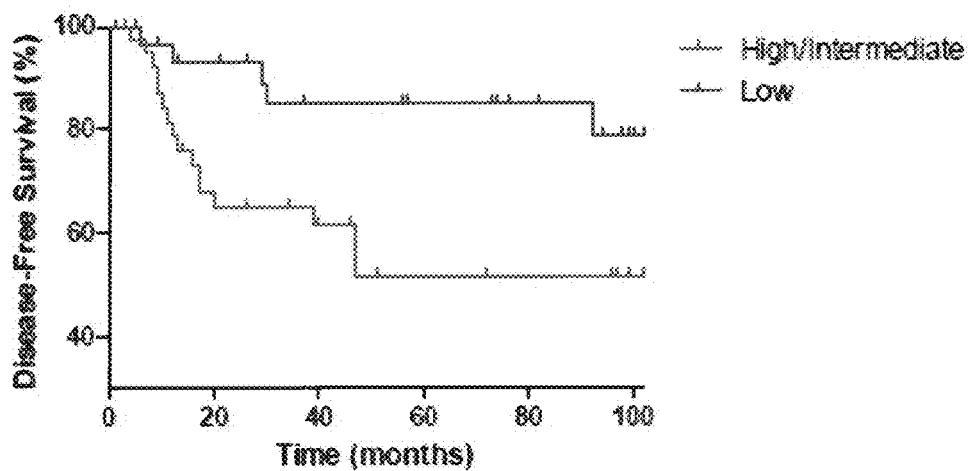
Fig. 9B

HSF1 AS A MARKER IN TUMOR PROGNOSIS AND TREATMENT

CROSS-REFERENCE TO RELATED APPLICATION

This application is a national stage filing under 35 U.S.C. 371 of International Application No. PCT/US2012/059086, filed Oct. 5, 2012, which claims the benefit under 35 U.S.C. §119(e) of U.S. Provisional Application No. 61/544,216, filed Oct. 6, 2011, the entire disclosure of which is incorporated herein by reference. International Application PCT/US2012/059086 was published under PCT Article 21(2) in English.

GOVERNMENT FUNDING STATEMENT

This invention was made with government support under R01-CA146445-01 awarded by the National Cancer Institute, under W81XWH-08-1-0282 BC-07456 awarded by the Department of Defense, and under K08NS064168 awarded by National Institutes of Health. The government has certain rights in the invention.

BACKGROUND OF THE INVENTION

Cancer is a leading cause of death worldwide and accounted for approximately 7.6 million deaths (around 13% of all deaths) in 2008 (Ferlay J, et al., GLOBOCAN 2008 v1.2, Cancer Incidence and Mortality Worldwide: IARC CancerBase No. 10 [Internet]. Lyon, France: International Agency for Research on Cancer; 2010). Although significant progress in the treatment of certain types of cancer such as childhood leukemia has been achieved over the past several decades, many of the most common types of cancer remain difficult to manage and are often incurable, particularly if discovered after the tumor has invaded locally or metastasized. Tumors can exhibit marked variability in terms of aggressiveness and response to treatment, despite displaying similar histopathologic features and stage. Such variability can complicate development of appropriate treatment plans for individual patients. There is a need in the art for identification and elucidation of pathways and cellular changes that contribute to malignancy. There is also a need in the art for innovative approaches for tumor prognosis and for selecting appropriate treatment regimens for individuals with cancer.

SUMMARY OF THE INVENTION

In some aspects, the invention provides a method of diagnosing cancer in a subject comprising the steps of: determining the level of Heat Shock Factor-1 (HSF1) expression or the level of HSF1 activation in a sample obtained from the subject, wherein increased HSF1 expression or increased HSF1 activation in the sample is indicative that the subject has cancer. In some embodiments, the method comprises comparing the level of HSF1 gene expression or HSF1 activation in the sample with a control level of HSF1 gene expression or HSF1 activation, wherein a greater level in the sample as compared with the control level is indicative that the subject has cancer. In some embodiments, the cancer is a cancer in situ (CIS). In some embodiments, the sample does not show evidence of invasive cancer. In some embodiments the sample comprises breast, lung, colon, prostate tissue, cervical, or nerve sheath tissue. In some embodiments the sample comprises breast tissue and the cancer is ductal carcinoma in situ (DCIS).

In some aspects, the invention provides a method of identifying cancer comprising the steps of: (a) providing a biological sample; and (b) determining the level of HSF1 expression or the level of HSF1 activation in the sample, wherein increased HSF1 expression or increased HSF1 activation in the sample is indicative of cancer. In some embodiments the method comprises comparing the level of HSF1 gene expression or HSF1 activation in the sample with a control level of HSF1 gene expression or HSF1 activation, wherein a greater level in the sample as compared with the control level is indicative of cancer. In some embodiments the sample does not show evidence of invasive cancer. In some embodiments the sample comprises breast, lung, colon, prostate, cervical, or nerve sheath tissue. In some embodiments the sample comprises breast tissue and the cancer is ductal carcinoma in situ (DCIS).

In some aspects, the invention provides a method of assessing a tumor with respect to aggressiveness, the method comprising: determining the level of HSF1 expression or HSF1 activation in a sample obtained from the tumor, wherein an increased level of HSF1 expression or activation is correlated with increased aggressiveness, thereby classifying the tumor with respect to aggressiveness. In some embodiments, the method comprises: (a) determining the level of HSF1 expression or the level of HSF1 activation in a sample obtained from the tumor; (b) comparing the level of HSF1 expression or HSF1 activation with a control level of HSF1 gene expression or HSF1 activation; and (c) assessing the aggressiveness of the tumor based at least in part on the result of step (b), wherein a greater level of HSF1 gene expression or HSF activation in the sample obtained from the tumor as compared with the control level of HSF1 gene expression or HSF activation, respectively, is indicative of increased aggressiveness.

In some aspects, the invention provides a method of classifying a tumor according to predicted outcome comprising steps of: determining the level of HSF1 expression or HSF1 activation in a sample obtained from the tumor, wherein an increased level of HSF1 expression or activation is correlated with poor outcome, thereby classifying the tumor with respect to predicted outcome. In some embodiments the method comprises (a) determining the level of HSF1 expression or the level of HSF1 activation in a tumor sample; and (b) comparing the level of HSF1 expression or HSF1 activation with a control level of HSF1 expression or HSF1 activation, wherein if the level determined in (a) is greater than the control level, the tumor is classified as having an increased likelihood of resulting in a poor outcome.

In some aspects, the invention provides a method of predicting cancer outcome in a subject, the method comprising: determining the level of HSF1 gene expression or the level of HSF1 activation in a tumor sample, wherein an increased level of HSF1 expression or activation is correlated with poor outcome, thereby providing a prediction of cancer outcome. In some embodiments the method comprises: (a) determining the level of HSF1 expression or the level of HSF1 activation in the tumor sample; and (b) comparing the level of HSF1 gene expression or HSF1 activation with a control level of HSF1 gene expression or HSF1 activation, wherein if the level determined in (a) is greater than the control level, the subject has increased likelihood of having a poor outcome.

In some aspects, the invention provides a method for providing prognostic information relating to a tumor, the method comprising: determining the level of HSF1 expression or HSF1 activation in a tumor sample from a subject in need of tumor prognosis, wherein if the level of HSF1 expression or HSF1 activation is increased, the subject is considered to have a poor prognosis. In some embodiments the method comprises: (a) determining the level of HSF1 expression or HSF1 activation in the sample; and (b) comparing the level with a control level, wherein if the level determined in (a) is greater than the control level, the subject is considered to have a poor prognosis.

In some aspects, the invention provides a method for providing treatment-specific predictive information relating to a tumor, the method comprising: determining the level of HSF1 expression or HSF1 activation in a tumor sample from a subject in need of tumor prognosis, wherein the level of HSF1 expression or HSF1 activation correlates with tumor sensitivity or resistance to a treatment, thereby providing treatment-specific predictive information. In some embodiments the treatment comprises hormonal therapy, and the method comprises steps of: (a) determining the level of HSF1 expression or HSF1 activation in the sample; and (b) comparing the level with a control level, wherein if the level determined in (a) is greater than the control level, the tumor has an increased likelihood of being resistant to hormonal therapy. In some embodiments, the treatment comprises proteostasis modulator therapy, method comprising steps of: (a) determining the level of HSF1 expression or HSF1 activation in the sample; and (b) comparing the level with a control level, wherein if the level determined in (a) is greater than the control level, the tumor has an increased likelihood of being sensitive to proteostasis modulator therapy. In some embodiments proteostasis modulator therapy comprises a heat shock response (HSR) inhibitor. In some embodiments proteostasis modulator therapy comprises an HSF1 inhibitor. In some embodiments proteostasis modulator therapy comprises an HSP90 inhibitor. In some embodiments proteostasis modulator therapy comprises a proteasome inhibitor.

In some aspects, the invention provides a method of determining whether a subject with a tumor is a suitable candidate for treatment with a proteostasis modulator, the method comprising assessing the level of HSF1 expression or HSF1 activation in a tumor sample obtained from the subject, wherein an increased level of HSF1 expression or an increased level of HSF1 activation in the sample is indicative that the subject is a suitable candidate for treatment with a proteostasis modulator. In some embodiments the proteostasis modulator is an HSR inhibitor. In some embodiments the proteostasis modulator is an HSF1 inhibitor. In some embodiments, the proteostasis modulator is an HSP90 inhibitor. In some embodiments the proteostasis modulator is a proteasome inhibitor.

In some aspects, the invention provides a method of predicting the likelihood that a tumor will be sensitive to a protein homeostasis modulator, the method comprising: (a) determining the level of HSF1 gene expression or the level of HSF1 activation in a sample obtained from the tumor; and (b) comparing the level of HSF1 gene expression or HSF1 activation with a control level of HSF1 gene expression or HSF1 activation, wherein if the level determined in (a) is greater than the control level, the tumor has an increased likelihood of being sensitive to the protein homeostasis modulator. In some embodiments the proteostasis modulator is an HSR inhibitor. In some embodiments the proteostasis modulator is an HSF1 inhibitor. In some embodiments, the proteostasis modulator is an HSP90 inhibitor. In some embodiments the proteostasis modulator is a proteasome inhibitor. In some embodiments the tumor is a carcinoma, e.g., an adenocarcinoma. In some embodiments the tumor is a CIS. In some embodiments the tumor is a Stage I tumor. In some embodiments the tumor is a breast, lung, colon, prostate, cervical, or malignant nerve sheath tumor. In some embodiments the tumor is a stage I lung adenocarcinoma or stage I breast tumor. In certain embodiments the tumor is a breast tumor, e.g., a breast tumor that is positive for estrogen receptor (ER) positive breast tumor, human epidermal growth factor 2 (HER2), or both. In some embodiments the tumor is a lymph node negative tumor, e.g., a lymph node negative breast tumor. In certain embodiments the tumor is a ductal carcinoma in situ (DCIS). In certain embodiments in which the tumor is a breast tumor, the method further comprises assessing the sample for ER, progesterone receptor (PR), HER2 status, or lymph node status (or any combination thereof).

In some aspects, the invention provides a method for tumor diagnosis, prognosis, treatment-specific prediction, or treatment selection comprising: (a) providing a sample obtained from a subject in need of diagnosis, prognosis, treatment-specific prediction, or treatment selection for a tumor; (b) determining the level of HSF1 expression or HSF1 activation in the sample; (c) scoring the sample based on the level of HSF1 expression or HSF1 activation, wherein the score provides diagnostic, prognostic, treatment-specific predictive, or treatment selection information. In some embodiments, scoring comprises determining the level of an HSF1 gene product in the sample. In some embodiments, scoring comprises determining the level of HSF1 in nuclei of cells in the sample. In some embodiments, scoring comprises generating a composite score based on the percentage of cells that exhibit nuclear HSF1 and the level of nuclear HSF1. In some embodiments, scoring comprises comparing the level of HSF1 expression or HSF1 activation in the sample with the level of HSF1 expression or HSF1 activation in a control. In some embodiments the tumor is a carcinoma, e.g., an adenocarcinoma. In some embodiments the tumor is a sarcoma. In some embodiments the tumor is a CIS. In some embodiments the tumor is a stage I tumor. In some embodiments the tumor is a breast, lung, colon, prostate, cervical, or malignant nerve sheath tumor. In some embodiments the tumor is a stage I lung adenocarcinoma or stage I breast tumor. In certain embodiments the tumor is a breast tumor, e.g., a breast tumor that is positive for estrogen receptor (ER) positive breast tumor, human epidermal growth factor 2 (HER2), or both. In some embodiments the tumor is a lymph node negative tumor, e.g., a lymph node negative breast tumor. In certain embodiments the tumor is a ductal carcinoma in situ (DCIS). In certain embodiments the tumor is an ER positive, lymph node negative breast tumor. In some embodiments wherein the tumor is a breast tumor and the method further comprises scoring the tumor for ER, PR, HER2, or lymph node status.

In some embodiments of any of the methods, determining the level of HSF1 expression comprises determining the level of an HSF1 gene product.

In some embodiments of any of the methods, determining the level of HSF1 expression comprises determining the level of HSF1 mRNA.

In some embodiments of any of the methods, determining the level of HSF1 expression comprises determining the level of HSF1 polypeptide.

In some embodiments of any of the methods, determining the level of HSF1 expression comprises detecting HSF1 polypeptide using an antibody that binds to HSF1 polypeptide.

In some embodiments of any of the methods, the sample comprises a tissue sample, and determining the level of expression or activation of HSF1 comprises performing immunohistochemistry (IHC) on the tissue sample.

In some embodiments of any of the methods, determining the level of HSF1 activation comprises measuring at least one bioactivity of HSF1 protein.

In some embodiments of any of the methods, determining the level of HSH activation comprises determining the localization of HSF1 polypeptide in cells, wherein nuclear localization is indicative of HSF1 activation. In some embodiments, nuclear localization is assessed using IHC.

In some embodiments of any of the methods, determining the level of HSF1 activation comprises detecting at least one post-translational modification of HSF1 polypeptide.

In some embodiments of any of the methods, determining the level of HSF1 activation comprises determining the level of phosphorylation of HSF1 polypeptide on serine 326, wherein phosphorylation of HSF1 polypeptide on serine 326 is indicative of HSF1 activation. In some embodiments the level of phosphorylated HSF1 (e.g., HSF1 phosphorylated on serine 326), is determined using an antibody that binds specifically to phosphorylated HSF1.

In some embodiments of any of the methods, determining the level of HSF1 activation comprises determining the level of chromatin occupancy by HSF1 polypeptide.

In some embodiments of any of the methods, determining the level of HSF1 activation comprises determining the level of a gene expression product of at least one HSF1-regulated gene other than a heat shock protein (HSP) gene.

In various embodiments of the methods described herein, a control sample can comprise normal non-neoplastic cells or tissue, e.g., normal non-neoplastic cells or tissue of the same type or origin as that from which a tumor arose. In various embodiments of the methods described herein, a control level of HSF1 expression or HSF1 activation can be a level measured in normal non-neoplastic cells or tissue, e.g., normal non-neoplastic cells or tissue of the same type or origin as that from which a tumor arose, e.g., as measured under conditions that do not activate the heat shock response.

In some embodiments, any of the methods can comprise providing a sample, e.g., a tumor sample. In some embodiments, any of the method can comprise providing a subject, e.g., a subject in need of tumor diagnosis, prognosis, or treatment selection.

In some embodiments, any of the methods can further comprise assessing at least one additional cancer biomarker. The at least one additional cancer biomarker is typically a gene or gene product (e.g., mRNA or protein) whose expression, activation, localization, or activity, correlates with the presence or absence of cancer, with cancer aggressiveness, with cancer outcome, cancer prognosis, or treatment-specific cancer outcome. The cancer biomarker(s) can be selected based on the tumor type.

In some embodiments, any of the methods can further comprise selecting or administering a therapeutic agent based at least in part on results of assessing the level of HSF1 expression or HSF1 activation. In some aspects, the invention provides a method comprising selecting or administering a treatment to a subject in need of treatment for a tumor, wherein the treatment is selected based at least in part on an assessment of the level of HSF1 expression or HSF1 activation in a sample obtained from the tumor. In some embodiments, a method comprises selecting or administering an appropriate therapy if CIS is detected. For example, the therapy can comprise surgical removal of the CIS. In some embodiments a method comprises selecting or administering a more aggressive therapy if a tumor (or sample obtained therefrom) is classified as having an increased likelihood of being aggressive, if a tumor or subject is classified as having an increased likelihood of having a poor outcome, or if a subject is classified as having a poor prognosis. For example, in some embodiments a method comprises selecting or administering adjuvant therapy (e.g., adjuvant chemotherapy) if a tumor (or sample obtained therefrom) is classified as having an increased likelihood of being aggressive, if a tumor or subject is classified as having an increased likelihood of having a poor outcome, or if a subject is classified as having a poor prognosis. In some embodiments a method comprises selecting or administering a proteostasis modulator if the level of HSF1 expression or the level of HSF1 activation is increased.

In some aspects, the invention provides a kit that comprises at least one agent of use to measure the level of HSF1 expression or HSF1 activation in a sample, e.g., an agent that specifically binds to an HSF1 gene product (e.g., HSF1 mRNA or HSF1 protein). The agent may be, e.g., an antibody, or a nucleic acid. In some embodiments the agent is validated for use in assessing HSF1 expression or HSF1 activation, in that results of an assay using the agent have been shown to correlate with cancer outcome, prognosis, or treatment efficacy of at least one specific treatment. In some embodiments the agent is an antibody useful for performing IHC.

Certain conventional techniques and concepts of cell biology, cell culture, molecular biology, microbiology, recombinant nucleic acid (e.g., DNA) technology, immunology, etc., which are within the skill and knowledge of those of ordinary skill in the art, may be of use in aspects of the invention. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005; Buchwalow, I. and Böcker, W. (2010) *Immunohistochemistry: Basics and Methods*, Methods in Molecular Medicine, Springer) Lodish H, et al. (2007). Molecular cell biology (6th ed.). New York: W.H. Freeman and CO. Further information on cancer and treatment thereof may be found in *Cancer: Principles and Practice of Oncology* (V. T. De Vita et al., eds., J.B. Lippincott Company, $8^{th}$ ed., 2008 or $9^{th}$ ed., 2011) and Weinberg, R A, *The Biology of Cancer*, Garland Science, 2006. All patents, patent applications, books, journal articles, databases, websites, and other publications mentioned herein are incorporated herein by reference in their entirety. In the event of a conflict or inconsistency with the specification, the specification shall control. Applicants reserve the right to amend the specification based on any of the incorporated references and/or to correct obvious errors. None of the content of the incorporated references shall limit the invention.

BRIEF DESCRIPTION OF THE DRAWING

The patent or application file contains at least one drawing executed in color. Copies of this patent or patent application publication with color drawings will be provided by the Office upon request and payment of the necessary fee.

FIG. 3. HSF1-positive tumors are associated with decreased survival in estrogen receptor-positive breast cancer. (A) Kaplan-Meier analysis of all individuals with breast cancer that were scored in this study. Kaplan-Meier analysis of participants with (B) HER2 positive (HER2+) breast cancer, (C) triple-negative breast cancer and (D) estrogen receptor-positive (ER+) breast cancer that had HSF1 in the nucleus (HSF1 +) or that had no detectable nuclear HSF1 (HSF1 −). In these analyses, low and high nuclear HSF1 expressors were included in the HSF1 + group. Kaplan-Meier analysis of individuals with (E) ER+, HER2+ and triple-negative breast cancer or (F) with only ER+ breast cancer expressing no nuclear HSF1, low nuclear HSF1 or high nuclear HSF1. Nurses' Health Study (1976-1997). Log-rank p values are shown.

FIG. 4. HSF1 is activated in multiple human breast carcinoma subtypes. A. High magnification of HSF1 staining in ER+, HER2+ and triple-negative breast sections. B. HSF1 is translocated from the cytoplasm to the nucleus in transformed cells in human breast tissue. Immunoperoxidase staining (brown) with an anti-HSF1 antibody of formalin-fixed paraffin-embedded human biopsy material containing both tumor and normal cells. Sections were counterstained with hematoxylin to identify nuclei (blue). C. Representative photomicrographs of tumors from the breast cancer TMAs that were stained by HSF1 immunohistochemistry and that were scored as having weak (white), low (pink), or high (red) HSF1 expression. Scoring for three TMAs are displayed as heatmaps. The top panel contains data from two TMAs, which together contain 138 breast tumors representing all major breast cancer subtypes. ER+ and HER2+ expression, in addition to HSF1 nuclear expression, are displayed. The middle panel displays the HSF1 nuclear expression of a triple-negative breast cancer TMA consisting of 151 tumors. The bottom panel displays the HSF1 nuclear expression of 16 normal mammary tissue sections. A summary of all HSF1 expression by tissue subtype is quantified in the bargraph on the right. D. HSF1 nuclear protein expression is correlated with poor outcome in ER+, lymph-node negative tumors from NHS.

FIG. 8: IHC of HSF1 in additional ER+, HER2+ & Triple Negative tumors. Immunoperoxidase staining (brown) with an anti-HSF1 antibody of formalin-fixed paraffin-embedded human biopsy material of (A) normal mammary tissue or (B) the indicated tumor subtypes. Blue staining nuclei with Mayer-hematoxylin counterstain are negative for HSF1. ER+ (estrogen receptor positive); TN (triple negative).

DETAILED DESCRIPTION OF CERTAIN EMBODIMENTS OF THE INVENTION

Glossary

Figure 1D:
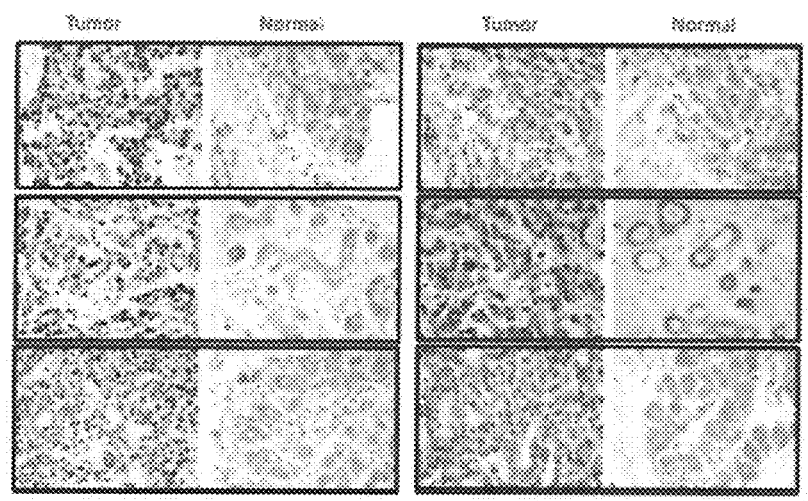
FIG. 1. HSF1 protein is increased in breast cancer. (A) Characterization of HSF1 antibody. Immunoblot analysis of spleen lysates from HSF1 wild-type (+/+) and HSF1 null mice (−/−). (B) Immunohistochemistry of mouse brain from HSF1 wild-type and HSF1 null mice, long development. Scale bar, 20 μM. (C) Upper panel, HSF1 immunoblot of matched pairs of invasive ductal carcinoma and adjacent normal breast from seven patients. Lower panel, protein stain for loading comparison. (D) HSF1 protein is increased in breast cancer (six matched tumor/normal pairs). HSF1 IHC of matched tumor and adjacent normal breast epithelium. Images are taken from the same section of tissue (i.e., the same slide).

For convenience, certain terms employed herein are collected below. It should be understood that any description of a term or concept below or elsewhere herein may be applied wherever such term or concept appears herein.

The term "antibody" refers to an immunoglobulin, whether natural or wholly or partially synthetically produced. An antibody may be a member of any immunoglobulin class, including any of the mammalian, e.g., human, classes: IgG, IgM, IgA, IgD, and IgE, or subclasses thereof, and may be an antibody fragment, in various embodiments of the invention. An antibody can originate from any of a variety of vertebrate (e.g., mammalian or avian) organisms, e.g., mouse, rat, rabbit, hamster, goat, chicken, human, etc. As used herein, the term "antibody fragment" refers to a derivative of an antibody which contains less than a complete antibody. In general, an antibody fragment retains at least a significant portion of the full-length antibody's specific binding ability. Examples of antibody fragments include, but are not limited to, Fab, Fab', F(ab')2, scFv, Fv, dsFv diabody, Fd fragments, and domain antibodies. Standard methods of antibody identification and production known in the art can be used to produce an antibody that binds to a polypeptide of interest. In some embodiments, an antibody is a monoclonal antibody. Monoclonal antibodies can be identified and produced, e.g., using hybridoma technology or recombinant nucleic acid technology (e.g., phage or yeast display). In some embodiments, an antibody is a chimeric or humanized or fully human antibody. In some embodiments, an antibody is a polyclonal antibody. In some embodiments an antibody is affinity purified. It will be appreciated that certain antibodies, e.g., recombinantly produced antibodies, can comprise a heterologous sequence not derived from naturally occurring antibodies, such as an epitope tags. In some embodiments an antibody further has a detectable label attached (e.g., covalently attached) thereto (e.g., the label can comprise a radioisotope, fluorescent compound, enzyme, hapten).

"Cancer" is generally used interchangeably with "tumor" herein and encompasses pre-invasive and invasive neoplastic growths comprising abnormally proliferating cells, including malignant solid tumors (carcinomas, sarcomas) and including hematologic malignancies such as leukemias in which there may be no detectable solid tumor mass. As used herein, the term cancer includes, but is not limited to, the following types of cancer: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma, oral cancer such as oral squamous cell carcinoma; ovarian cancer including ovarian cancer arising from epithelial cells, stromal cells, germ cells and mesenchymal cells; pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma. "Carcinoma" as used herein, refers to a cancer arising or believed to have arisen from epithelial cells, e.g., cells of the cancer possess various molecular, cellular, and/or histological characteristics typical of epithelial cells. "Cancer in situ" (CIS) refers to cancers in which neoplastic cells are present at a location, e.g., as a tumor, but have not detectably invaded beyond the original site where they were discovered, e.g., cancer cells have not detectably passed through the basal lamina. It will be appreciated that a CIS may have undergone some local spread at the time of discovery. In many embodiments a CIS is a tumor that would be classified as Stage 0, e.g., TisN0M0 or TaN0M0 according to the TNM Classification of Malignant Tumours (TNM) (Sobin L H, et al., eds. TNM Classification of Malignant Tumors, 7th ed. Wiley-Blackwell, Oxford 2009). In some embodiments, a CIS is a bladder cancer, breast cancer (e.g., ductal carcinoma in situ of the breast (DCIS)), cervical cancer (in which case the term high grade squamous epithelial lesion (HSIL) may be used instead of CIS), colon cancer, lung cancer (e.g., bronchioloalveolar carcinoma (BAC)), high grade prostatic intraepithelial neoplasia, or skin cancer.

The term "diagnostic method" generally refers to a method that provides information regarding the identity of a disease or condition that affects a subject or whether a subject is suffering from a disease or disorder of interest, such as cancer. For example, a diagnostic method may determine that a subject is suffering from a disease or condition of interest or may identify a disease or condition that affects a subject or may identify a subject suffering from a disease or condition of interest.

The term "modulator" refers to an agent or condition that alters, e.g., inhibits (reduces, decreases) or enhances (activates, stimulates, increases), a process, pathway, phenomenon, state, or activity. For example, a modulator of protein activity may increase or decrease the level of one or more activit(ies) of a protein.

The term "prognostic method", generally refers to a method that provides information regarding the likely course or outcome of a disease regardless of treatment or across treatments (e.g., after adjusting for treatment variables or assuming that a subject receives standard of care treatment). For example, a prognostic method may comprise classifying a subject or sample obtained from a subject into one of multiple categories, wherein the categories correlate with different likelihoods that a subject will experience a particular outcome. For example, categories can be low risk and high risk, wherein subjects in the low risk category have a lower likelihood of experiencing a poor outcome (e.g., within a given time period such as 5 years or 10 years) than do subjects in the high risk category. A poor outcome could be, for example, disease progression, disease recurrence, or death attributable to the disease.

The term "treatment-specific predictive method" generally refers to a method that provides information regarding the likely effect of a specified treatment, e.g., that can be used to predict whether a subject is likely to benefit from the treatment or to predict which subjects in a group will be likely or most likely to benefit from the treatment. It will be understood that a treatment-specific predictive method may be specific to a single treatment or to a class of treatments (e.g., a class of treatments having the same or a similar mechanism of action or that act on the same biological process, pathway or molecular target, etc.). A treatment-specific predictive method may comprise classifying a subject or sample obtained from a subject into one of multiple categories, wherein the categories correlate with different likelihoods that a subject will benefit from a specified treatment. For example, categories can be low likelihood and high likelihood, wherein subjects in the low likelihood category have a lower likelihood of benefiting from the treatment than do subjects in the high likelihood category. In some embodiments, a benefit is increased survival, increased progression-free survival, or decreased likelihood of recurrence. In some embodiments, a "suitable candidate for treatment" with a specified agent refers to a subject for whom there is a reasonable likelihood that the subject would benefit from administration of the agent, e.g., the tumor has one or more characteristics that correlate with a beneficial effect resulting from administration of the agent as compared with, e.g., no treatment or as compared with a standard treatment. In some embodiments, a "suitable candidate for treatment" with an agent refers to a subject for whom there is a reasonable likelihood that the subject would benefit from administration of the agent in combination with (i.e., in addition to) one or more other therapeutic interventions, e.g., the tumor has one or more characteristics that correlate with a beneficial effect from treatment with the agent and the other therapeutic interventions as compared with treatment with the other therapeutic interventions only. In some embodiments, a suitable candidate for treatment with an agent is a subject for whom there is a reasonable likelihood that the subject would benefit from addition of the agent to a standard regimen for treatment of cancer. See, e.g., De Vita, et al., supra for non-limiting discussion of standard regimens for treatment of cancer.

"Expression" refers to the cellular processes involved in producing RNA and protein such as, but not limited to, transcription, RNA processing, and translation.

As used herein, the term "gene product" (also referred to as a "gene expression product") encompasses products resulting from expression of a gene, such as RNA transcribed from a gene and polypeptides arising from translation of mRNA. RNA transcribed from a gene can be non-coding RNA or coding RNA (e.g., mRNA). It will be appreciated that gene products may undergo processing or modification by a cell. For example, RNA transcripts may be spliced, polyadenylated, etc., prior to mRNA translation, and/or polypeptides may undergo co-translational or post-translational processing such as removal of secretion signal sequences or modifications such as phosphorylation, fatty acylation, etc. The term "gene product" encompasses such processed or modified forms. Genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Exemplary databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest. It will be appreciated that multiple alleles of a gene may exist among individuals of the same species due to natural allelic variation. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations frequently do not alter the encoded amino acid sequence, although DNA polymorphisms that lead to changes in the amino acid sequences of the encoded proteins can exist. It will also be understood that multiple isoforms of certain proteins encoded by the same gene may exist as a result of alternative RNA splicing or editing. Examples of polymorphic variants can be found in, e.g., the Single Nucleotide Polymorphism Database (dbSNP) (available at the NCBI website at www.ncbi.nlm.nih.gov/projects/SNP/), which contains single nucleotide polymorphisms (SNPs) as well as other types of variations (see, e.g., Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (MD): National. Center for Biotechnology Information (US); 2002 (www.ncbi.nlm.nih.gov/bookshelf/br.fcgi?book=handbook&part=ch5). In general, where aspects of the invention relate to a gene or gene product it should be understood that embodiments relating to such isoforms or allelic variants are encompassed unless indicated otherwise. For example, in general, allelic variants and most isoforms would be detectable using the same reagents (e.g., antibodies, probes, etc.) and methods. Certain embodiments may be directed to a particular sequence or sequences, e.g., a particular allele or isoform. One of ordinary skill in the art could readily develop reagents and methods that could distinguish between different isoforms or allelic variants or could verify that particular isoform(s) or allelic variant(s) are detected by a particular detection method or reagent.

"Isolated", in general, means 1) separated from at least some of the components with which it is usually associated in nature; 2) prepared or purified by a process that involves the hand of man; and/or 3) not occurring in nature, e.g., present in an artificial environment.

"Nucleic acid" is used interchangeably with "polynucleotide" and encompasses in various embodiments naturally occurring polymers of nucleosides, such as DNA and RNA, and non-naturally occurring polymers of nucleosides or nucleoside analogs. In some embodiments a nucleic acid comprises standard nucleosides (abbreviated A, G, C, T, U). In other embodiments a nucleic acid comprises one or more non-standard nucleosides. In some embodiments, one or more nucleosides are non-naturally occurring nucleosides or nucleotide analogs. A nucleic acid can comprise modified bases (for example, methylated bases), modified sugars (2'-fluororibose, arabinose, or hexose), modified phosphate groups or other linkages between nucleosides or nucleoside analogs (for example, phosphorothioates or 5'-N-phosphoramidite linkages), locked nucleic acids, or morpholines, in various embodiments. In some embodiments, a nucleic acid comprises nucleosides that are linked by phosphodiester bonds, as in DNA and RNA. In some embodiments, at least some nucleosides are linked by non-phosphodiester bond(s). A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications, including use of non-standard nucleosides) known in the art as being useful in the context of RNA interference (RNAi), aptamer, antisense, primer, or probe molecules may be used in various embodiments of the invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. In some embodiments, a modification increases half-life and/or stability of a nucleic acid, e.g., relative to RNA or DNA of the same length and strandedness. A nucleic acid may comprise a detectable label, e.g., a fluorescent dye, radioactive atom, etc. "Oligonucleotide" refers to a relatively short nucleic acid, e.g., typically between about 4 and about 100 nucleotides long. Where reference is made herein to a polynucleotide, it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence, if presented herein, is presented in a 5' to 3' direction unless otherwise indicated.

"Polypeptide" refers to a polymer of amino acids. The terms "protein" and "polypeptide" are used interchangeably herein. A peptide is a relatively short polypeptide, typically between about 2 and 100 amino acids in length. Polypeptides used herein typically contain the standard amino acids (i.e., the 20 L-amino acids that are most commonly found in proteins). However, a polypeptide can contain one or more non-standard amino acids (which may be naturally occurring or non-naturally occurring) and/or amino acid analogs known in the art in certain embodiments. One or more of the amino acids in a polypeptide may be modified, for example, by the addition of a chemical entity thereto. Exemplary modifications include phosphorylation, glycosylation, SUMOylation, acetylation, methylation, acylation, etc. In some embodiments, a polypeptide is modified by attachment of a linker useful for conjugating the polypeptide to or with another entity. Polypeptides may be present in or purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence, if presented herein, is presented in an N-terminal to C-terminal direction unless otherwise indicated.

A "sample" as used herein can be any biological specimen that contains cells, tissue, or cellular material (e.g., cell lysate or fraction thereof). Typically, a sample is obtained from (i.e., originates from, was initially removed from) a subject. Methods of obtaining such samples are known in the art and include, e.g., tissue biopsy such as excisional biopsy, incisional biopy, or core biopsy; fine needle aspiration biopsy; brushings; lavage; or collecting body fluids such as blood, sputum, lymph, mucus, saliva, urine, etc., etc. In many embodiments, a sample contains at least some intact cells at the time it is removed from a subject and, in many embodiments, the sample retains at least some of the tissue microarchitecture. In many embodiments a sample will have been obtained from a tumor either prior to or after removal of the tumor from a subject. A sample may be subjected to one or more processing steps after having been obtained from a subject and/or may be split into one or more portions, which may entail removing or discarding part of the original sample. It will be understood that the term "sample" encompasses such processed samples, portions of samples, etc., and such samples are still considered to have been obtained from the subject from whom the initial sample was removed. In many embodiments, a sample is obtained from an individual who has been diagnosed with cancer or is at increased risk of cancer, is suspected of having cancer, or is at risk of cancer recurrence. A sample used in a method of the present invention may have been procured directly from a subject, or indirectly by receiving the sample from one or more persons who procured the sample directly from the subject, e.g., by performing a biopsy or other procedure on the subject. A "tumor sample" is a sample that includes at least some cells, tissue, or cellular material obtained from a tumor. In general, a "sample" as used herein is typically a tumor sample or a sample obtained from tissue being evaluated for presence of a tumor.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments a small molecule is an artificial (non-naturally occurring) molecule. In some embodiments, a small molecule is non-polymeric. In some embodiments, a small molecule is not an amino acid. In some embodiments, a small molecule is not a nucleotide. In some embodiments, a small molecule is not a saccharide. In some embodiments, the term "small molecule" excludes molecules that are ingredients found in standard tissue culture medium.

"Specific binding" generally refers to a physical association between a target molecule or complex (e.g., a polypeptide) and a binding agent such as an antibody or ligand. The association is typically dependent upon the presence of a particular structural feature of the target such as an antigenic determinant, epitope, binding pocket or cleft, recognized by the binding agent. For example, if an antibody is specific for epitope A, the presence of a polypeptide containing epitope A or the presence of free unlabeled A in a reaction containing both free labeled A and the binding molecule that binds thereto, will typically reduce the amount of labeled A that binds to the binding molecule. It is to be understood that specificity need not be absolute but generally refers to the context in which the binding occurs. For example, it is well known in the art that antibodies may in some instances cross-react with other epitopes in addition to those present in the target. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule such as HSF1). It is also to be understood that specificity may be evaluated in the context of additional factors such as the affinity of the binding agent for the target versus the affinity of the binding agent for other targets, e.g., competitors. If a binding agent exhibits a high affinity for a target molecule that it is desired to detect and low affinity for nontarget molecules, the antibody will likely be an acceptable reagent. Once the specificity of a binding molecule is established in one or more contexts, it may be employed in other contexts, e.g., similar contexts such as similar assays or assay conditions, without necessarily re-evaluating its specificity. In some embodiments specificity of an antibody can be tested by performing an appropriate assay on a sample expected to lack the target (e.g., a sample from cells in which the gene encoding the target has been disabled or effectively inhibited) and showing that the assay does not result in a signal significantly different to background.

"Subject" refers to any individual, e.g., any individual who has or may have cancer or is at risk of developing cancer or cancer recurrence. The subject is preferably a human or non-human animal, including but not limited to animals such as rodents (e.g., mice, rats, rabbits), cows, pigs, horses, chickens, cats, dogs, primates, etc., and is typically a mammal, and in many embodiments is a human. In some embodiments a subject is female. In some embodiments a subject is male. A subject may be referred to as a "patient".

HSF1 as a Marker for Cancer Classification

Heat shock factor 1 (HSF1), also known as heat shock transcription factor 1, is a multifaceted transcription factor that governs the cellular response to a variety of disruptions in protein homeostasis, serving as the master transcriptional regulator of the cellular response to heat and various other stressors in mammals. Under normal (non-stressed) conditions, HSF1 is predominantly located in the cytoplasm as a monomer, which is unable to bind DNA. Upon exposure to stressors, HSF1 is activated and translocates to the nucleus, where it regulates gene expression by binding to DNA sequence motifs known as heat-shock elements (HSE) located in the promoter regions of target genes. To protect the proteome under various physiologic or environmental stresses, HSF1 drives the production of classic heat-shock proteins (HSPs) such as HSP27, HSP70 and HSP90 that act as protein chaperones. Among other activities, HSPs facilitate proper protein folding and assembly and help prevent deleterious protein aggregation. This response, termed the heat shock response (HSR), is present in eukaryotes ranging from yeast to humans (1-3).

As described herein, Applicants have discovered that HSF1 expression and activation are increased across a broad range of human tumor types and that increased HSF1 expression and activation in tumors are an indicator of aggressive tumor phenotypes and poor clinical outcome. For example, Applicants observed a striking increase in the levels of HSF1, as well as a shift in its localization from the cytoplasm to the nucleus, in a panel of human breast cancer samples as compared with normal breast tissue. Applicants also found that HSF1 expression and nuclear localization were increased in lung, colon, prostate, cervical carcinomas as well in other tumors including malignant peripheral nerve sheath tumor. Nuclear HSF1 levels were elevated in ~80% of in situ and invasive breast carcinomas analyzed. In invasive carcinomas, HSF1 expression was associated with high histologic grade, larger tumor size, and nodal involvement at diagnosis. Applicants hypothesized that this increase in nuclear HSF1 might be associated with poor prognosis. To investigate this possibility, Applicants examined the relationship between HSF1, clinicopathological characteristics, and survival outcomes among over 1,800 invasive breast cancer cases from the Nurses' Health Study. They found that increased levels of HSF1 expression and nuclear localization in tumor samples correlated with high histologic grade, larger tumor size, and nodal involvement at diagnosis in invasive breast carcinomas. Increased HSF1 levels and nuclear localization of HSF1 were associated with advanced clinical stage at the time of diagnosis and with increased mortality. The prognostic value of HSF1 protein was retained after adjusting for age, stage, grade, and adjuvant therapy. Thus, HSF1 is an independent prognostic indicator of outcome in breast cancer. Increased HSF1 expression and activation were shown to correlate with decreased overall survival and decreased disease free progression in a group of 70 stage I lung cancer patients and with decreased survival in colon cancer patients. Thus, increased HSF1 expression and activation in tumors correlates with aggressive tumor phenotype and worse clinical outcomes.

Without wishing to be bound by any theory, Applicants hypothesize that HSF1 may in part enable more aggressive cancer phenotypes and lead to worse clinical outcomes as a result of HSP elevation, driven by HSF1 responding to the protein folding conditions that are common in malignancies, such as increased protein load from dysregulation of the translation machinery, accumulation of mutated or fusion proteins, and imbalances in the stoichiometry of protein complexes due to aneuploidy. However, Applicants hypothesize that HSF1's role in cancer is much broader. Malignant transformation alters cellular physiology and imposes significant metabolic and genetic stresses in addition to proteomic stresses. HSF1's impact on cell cycle control, survival signaling, and energy metabolism during tumor initiation and progression may allow tumor cells to cope with these malignancy-associated stressors and/or may facilitate progression to invasive cancer and/or emergence of drug resistance by enabling the generation of greater phenotypic diversity.

In some aspects, the invention provides methods of classifying a sample with respect to cancer diagnosis (e.g., the presence or absence of cancer), cancer aggressiveness, cancer outcome, or cancer treatment selection, based at least in part on assessing the level of HSF1 expression or HSF1 activation in the sample. In some aspects, the invention provides methods of cancer diagnosis, prognosis, or treatment-specific prediction, based at least in part on assessing the level of HSF1 expression or HSF1 activation in a sample, e.g., a tumor sample or suspected tumor sample. In some embodiments, the cancer is an adenocarcinoma. In some embodiments the cancer is a breast, lung, colon, prostate, or cervical cancer, e.g., a breast, lung, colon, prostate, or cervical adenocarcinoma. In some embodiments the tumor is a squamous cell carcinoma. In some embodiments the tumor is not a squamous cell carcinoma. In some embodiments the cancer is a sarcoma. In some embodiments the sarcoma is a nerve sheath tumor, e.g., a peripheral nerve sheath tumor. In some embodiments the nerve sheath tumor is a malignant nerve sheath tumor, e.g., a malignant peripheral nerve sheath tumor. In some embodiments a tumor is a Stage I tumor as defined in the TNM Classification of Malignant Tumours (2009). In some embodiments a tumor is a Stage II tumor as defined in the TNM Classification of Malignant Tumours (2009). It will be understood that results of an assay of HSF1 expression or HSF1 activation may be used in combination with results from other assays, or other information, to provide a sample classification, diagnosis, prognosis, or prediction relating to cancer, cancer outcome, or treatment response. Such combination methods are within the scope of the invention.

In some aspects, the invention relates to methods for classifying a sample according to the level of HSF1 expression (i.e., the level of expression of the HSF1 gene) or according to the level of HSF1 activation in the sample. For purposes hereof, a method that comprises assessing HSF1 expression or assessing HSF1 activation may be referred to as an "HSF1-based method". A procedure that is used to assess (detect, measure, determine, quantify) HSF1 expression or HSF1 activation may be referred to as an "HSF1-based assay". It will be understood that either HSF1 expression, HSF1 activation, or both, can be assessed in various embodiments of the invention. Certain assays such as IHC can be used to assess both expression and activation. In general, as described further in the Examples, the level of HSF1 activation detected in tumor samples correlated with the level of HSF1 expression, e.g., samples that exhibited increased nuclear HSF1 levels tended to have increased HSF1 protein expression.

In some embodiments, the level of HSF1 expression is assessed by determining the level of an HSF1 gene product in the sample. Thus in some embodiments, the invention relates to methods for classifying a sample according to the level of an HSF1 gene product in the sample. In some embodiments, the invention provides a method of classifying a sample, the method comprising steps of: (a) providing a sample obtained from a subject; and (b) assessing HSF1 expression in the sample, wherein the level of HSF1 expression is correlated with a phenotypic characteristic, thereby classifying the sample with respect to the phenotypic characteristic. In some embodiments, the invention provides a method of classifying a sample, the method comprising steps of: (a) providing a sample obtained from a subject; and (b) determining the level of an HSF1 gene product in the sample, wherein the level of an HSF1 gene product is correlated with a phenotypic characteristic, thereby classifying the sample with respect to the phenotypic characteristic. In some embodiments the phenotypic characteristic is presence or absence of cancer. In some embodiments, the cancer is invasive cancer. In some embodiments the sample does not show evidence of invasive cancer, and the phenotypic characteristic is presence or absence of pre-invasive cancer (cancer in situ). In some embodiments the phenotypic characteristic is cancer prognosis. In some embodiments the phenotypic characteristic is predicted treatment outcome. In some embodiments the HSF1 gene product is HSF1 mRNA. In some embodiments the HSF1 gene product is HSF1 polypeptide.

In some aspects, the invention provides a method of classifying a sample, the method comprising: (a) determining the level of HSF1 expression or the level of HSF1 activation in a sample; (b) comparing the level of HSF1 expression or HSF1 activation with a control level of HSF1 gene expression or HSF1 activation; and (c) classifying the sample with respect to cancer diagnosis, wherein a greater (increased) level of HSF1 gene expression or HSF1 activation in the sample as compared with the control level of HSF1 expression or HSF activation, respectively, is indicative of the presence of cancer. In some embodiments, a greater level of HSF1 expression or HSF1 activation in the sample is indicative of the presence of in situ cancer in a sample that does not show evidence of invasive cancer. If the level of HSF1 expression or HSF1 activation is not increased (e.g., HSF1 is not detectable or is not significantly greater than present in normal tissue), then cancer is not diagnosed based on HSF1.

In some aspects, the invention provides a method of classifying a sample, the method comprising: (a) determining the level of HSF1 expression or the level of HSF1 activation in a sample obtained from a tumor; (b) comparing the level of HSF1 expression or HSF1 activation with a control level of HSF1 gene expression or HSF1 activation; and (c) classifying the sample with respect to cancer prognosis, wherein a greater level of HSF1 gene expression or HSF activation in the sample obtained from the tumor as compared with the control level of HSF1 gene expression or HSF activation, respectively, is indicative that the sample originated from a tumor that belongs to a poor prognosis class. In some aspects, the invention provides a method of classifying a tumor, the method comprising: (a) determining the level of HSF1 expression or the level of HSF1 activation in a sample obtained from a tumor; (b) comparing the level of HSF1 expression or HSF1 activation with a control level of HSF1 gene expression or HSF1 activation; and (c) classifying the sample with respect to cancer prognosis, wherein a greater level of HSF1 gene expression or HSF activation in the sample obtained from the tumor as compared with the control level of HSF1 gene expression or HSF1 activation, respectively, is indicative that the tumor belongs to a poor prognosis class.

In some aspects, the invention relates to methods for classifying a sample according to the level of HSF1 activation in cells of the sample. As used herein, "HSF1 activation" refers the process in which HSF1 polypeptide is phosphorylated, trimerizes, and translocates to the nucleus, where it binds to DNA sequences and regulates expression of genes containing such sequences (e.g., in their promoter regions) ("HSF1-regulated genes"). In some embodiments, the invention is directed to a method of classifying a sample with respect to a phenotypic characteristic, the method comprising steps of: (a) providing a sample obtained from a subject; and (b) determining the level of activation of HSF1 polypeptide in the sample, wherein the level of activation of an HSF1 polypeptide is correlated with a phenotypic characteristic, thereby classifying the sample with respect to the phenotypic characteristic. In some embodiments the sample does not show evidence of invasive cancer, and the phenotypic characteristic is presence or absence of pre-invasive cancer. In some embodiments the phenotypic characteristic is cancer prognosis. In some embodiments the phenotypic characteristic is predicted treatment outcome. In some embodiments, the level of HSF1 activation is assessed by determining the level of nuclear HSF1 in the sample. Thus in some embodiments the invention relates to methods for classifying a sample according to the level of nuclear HSF1 in the sample. In some embodiments, assessing the level of HSF1 activation comprises assessing HSF1 activity. In some embodiments, assessing the level of HSF1 activity comprises measuring expression of one or more HSF1-regulated genesIn some embodiments, assessing the level of HSF1 activity comprises measuring binding of HSF1 to the promoter region of one or more HSF1-regulated genes.

In some aspects of the invention, detection of increased HSF expression or activation in a sample is of use for diagnosis of cancer, e.g., for detection of cancer. According to certain of the methods of the invention, samples can be classified as belonging to (i.e., obtained from) an individual who has cancer or is likely to develop cancer. Among other things, the present invention provides the recognition that HSF1 expression in many instances initially becomes elevated during the in situ stage of malignant transformation, prior to invasion. In some aspects of the invention, detection of elevated (increased) HSF expression or activation in a sample is of use for early diagnosis of cancer, e.g., for detection of cancer in situ. According to certain of the methods of the invention, samples can be classified as belonging to (i.e., obtained from) an individual who has cancer in situ (CIS) or is likely to develop CIS or who has CIS and is likely to develop invasive cancer. In some embodiments the sample can be classified as belonging to (i.e., obtained from) an individual who has or is likely to develop ductal carcinoma in situ of the breast (DCIS).

In some embodiments, detection of increased HSF1 expression or activation in a sample indicates that a subject has an increased likelihood of having CIS or developing CIS than would be the case in the absence of increased HSF1 expression or activation. In some embodiments, detection of increased HSF1 expression or activation in a sample is of use to detect a CIS before it becomes detectable on physical examination or, in some embodiments, before it becomes detectable on imaging. In some embodiments, detection of increased HSF1 expression or activation in a sample may be used to help differentiate lesions that are malignant or that have significant potential to become invasive or metastasize from benign lesions. In accordance with certain embodiments of the invention, a lesion has an increased likelihood of being malignant or having significant potential to become invasive or metastasize if increased HSF1 expression or activation is detected in the sample than would be the case if increased HSF1 expression or activation is not detected. Detection of increased HSF1 expression or activation in a sample could, for example, indicate a need for additional or more frequent follow-up of the subject or for treatment of the subject from whom the sample was obtained. In some embodiments, detection of elevated HSF1 expression or activation in a sample is used together with one or more other indicators of dysplasia and/or neoplasia to detect the presence of CIS or to differentiate lesions that are malignant or that have significant potential to become invasive or metastasize from benign lesions. In some embodiments, detection of elevated HSF1 expression may enable classification of a sample that could not be reliably classified (e.g., as high risk or low risk) using standard histopathologic criteria. It will be understood that whether a sample (or tumor from which the sample originated) has an increased level of HSF1 expression or HSF1 activation can be determined by comparing the sample with a suitable control.

In some aspects, the invention provides method of identifying CIS, comprising assessing expression of HSF1 or activation of HSF1 in a tissue or cell sample, wherein the sample does not show evidence of invasive cancer, and wherein increased expression of HSF1 or increased activation of HSF1 in the sample is indicative of CIS. In some aspects, the invention provides a method of predicting the likelihood that a subject will develop invasive cancer, comprising assessing expression of the HSF1 gene or activation of HSF1 in a tissue or cell sample obtained from the subject, wherein increased expression of HSF1 or increased activation of HSF1 in the sample is indicative of an increased likelihood that the subject will develop invasive cancer. In some aspects, the invention provides a method of method of diagnosing CIS in a subject, comprising assessing expression of HSF1 or activation of HSF1 in a tissue or cell sample obtained from the subject, wherein the sample does not show evidence of invasive cancer, and wherein increased expression of HSF1 or increased activation of HSF1 in the sample indicates the presence of CIS in the subject.

In some embodiments, classification of DCIS lesions based on HSF1 expression or HSF1 activation may be used to differentiate DCIS lesions that are likely to progress to invasive cancer from those lesions that are likely to remain unchanged over extended periods of time or to disappear. DCIS lesions that exhibit elevated HSF1 expression or activation in a sample obtained from the lesion would be classified as having a greater likelihood of progression (e.g., within a time period such as 1 year) than lesions that do not exhibit elevated HSF1 expression or HSF1 activation in a sample obtained therefrom.

In some embodiments, a method of identifying, detecting, or diagnosing cancer, e.g., cancer in situ, is applied to a sample obtained from a subject who is at increased risk of cancer (e.g., increased risk of developing cancer or having cancer) or is suspected of having cancer or is at risk of cancer recurrence. A subject at increased risk of cancer may be, e.g., a subject who has not been diagnosed with cancer but has an increased risk of developing cancer as compared with a control, who may be matched with regard to one or more demographic characteristics such as age, gender, etc. For example, the subject may have a risk at least 1.2, 1.5, 2, 3, 5, 10 or more times that of an age-matched control (e.g., of the same gender), in various embodiments of the invention. It will be understood that "age-matched" can refer to the same number of years of age as the subject or within the same age range as the subject (e.g., a range of 5 or 10 years). For example, a control may be up to 5 years older or younger than the subject. Determining whether a subject is considered "at increased risk" of cancer is within the skill of the ordinarily skilled medical practitioner. Any suitable test(s) and/or criteria can be used. For example, a subject may be considered "at increased risk" of developing cancer if any one or more of the following apply: (i) the subject has a mutation or genetic polymorphism that is associated with increased risk of developing or having cancer relative to other members of the general population not having such mutation or genetic polymorphism (e.g., certain mutations in the BRCA1 or BRCA2 genes are well known to be associated with increased risk of a variety of cancers, including breast cancer and ovarian cancer; mutations in tumor suppressor genes such as Rb or p53 can be associated with a variety of different cancer types); (ii) the subject has a gene or protein expression profile, and/or presence of particular substance(s) in a sample obtained from the subject (e.g., blood), that is/are associated with increased risk of developing or having cancer relative to other members of the general population not having such gene or protein expression profile, and/or substance(s) in a sample obtained from the subject; (iii) the subject has one or more risk factors such as having a family history of cancer, having been exposed to a tumor-promoting agent or carcinogen (e.g., a physical carcinogen, such as ultraviolet or ionizing radiation; a chemical carcinogen such as asbestos, tobacco components or other sources of smoke, aflatoxin, or arsenic; a biological carcinogen such as certain viruses or parasites), or has certain conditions such as chronic infection/inflammation that are correlated with increased risk of cancer; (iv) the subject is over a specified age, e.g., over 60 years of age, etc. In the case of breast cancer, a subject diagnosed as having lobular carcinoma in situ (LCIS) is at increased risk of developing cancer. A subject suspected of having cancer may be a subject who has one or more symptoms of cancer or who has had a diagnostic procedure performed that suggested or was at least consistent with the possible existence of cancer but was not definitive. A subject at risk of cancer recurrence can be any subject who has been treated for cancer such that the cancer was rendered undetectable as assessed, for example, by appropriate methods for cancer detection.

According to certain methods of the invention, a sample, tumor, or subject can be classified as belonging to a particular class of outcome based at least in part on the level of HSF1 expression or HSF1 activation. For example, in some embodiments, a sample, tumor, or subject can be classified as belonging to a high risk class (e.g., a class with a prognosis for a high likelihood of recurrence after treatment or a class with a prognosis for a high likelihood of discovery of metastasis post-diagnosis or a class with a poor prognosis for survival after treatment) or a low risk class (e.g., a class with a prognosis for a low likelihood of recurrence after treatment or a class with a prognosis for a low likelihood of discovery of metastasis post-diagnosis or a class with a good prognosis for survival after treatment). In some embodiments, survival after treatment is assessed 5 or 10 years after diagnosis, wherein increased expression of HSF1 or increased activation of HSF1 is predictive of decreased likelihood of survival at 5 years or 10 years post-diagnosis. In some embodiments, increased expression of HSF1 or increased activation of HSF1 is predictive of decreased mean (average) or median survival. In some embodiments survival is overall survival, wherein increased expression of HSF1 or increased activation of HSF1 is predictive of decreased overall survival (increased overall mortality). In some embodiments survival is disease-specific survival, wherein increased expression of HSF1 or increased activation of HSF1 is predictive of decreased disease-specific survival (i.e., increased disease-specific mortality), wherein "disease-specific" in the context of outcome, refers to considering only deaths due to cancer, e.g., breast cancer.

According to certain methods of the invention, a sample, tumor, or subject can be classified as belonging to a particular class with regard to tumor aggressiveness. For example, a sample or tumor can be classified into a more aggressive class or a less aggressive class or a subject can be classified as having a tumor that is more aggressive or less aggressive. "More aggressive" in this context means that the sample or tumor has one or more features that correlate with a poor outcome. A poor outcome may be, e.g., progression (e.g., after treatment), recurrence after treatment, or cancer-related mortality (e.g., within 5, 10, or 20 years after treatment). For example, a tumor classified as more aggressive may have an increased likelihood of having metastasized locally or to remote site(s) at the time of diagnosis, an increased likelihood of metastasizing or progressing locally (e.g., within a specified time period after diagnosis such as 1 year, 2 years, etc.), an increased likelihood of treatment resistance (e.g., a decreased likelihood of being eradicated or rendered undetectable by treatment). In some aspects, the invention provides a method of assessing the aggressiveness of a tumor, the method comprising: determining the level of HSF1 expression or the level of HSF1 activation in a sample obtained from the tumor, wherein if the level of HSF1 gene expression or HSF activation in the sample obtained from the tumor is increased, the tumor is classified as belonging to a more aggressive class. In some aspects, the invention provides a method of assessing the aggressiveness of a tumor, the method comprising: (a) determining the level of HSF1 expression or the level of HSF1 activation in a sample obtained from the tumor; (b) comparing the level of HSF1 expression or HSF1 activation with a control level of HSF1 gene expression or HSF1 activation; and (c) assessing the aggressiveness of the tumor based at least in part on the result of step (b), wherein a greater level of HSF1 gene expression or HSF activation in the sample obtained from the tumor as compared with the control level of HSF1 gene expression or HSF activation, respectively, is indicative of increased aggressiveness.

In some aspects, the invention provides a method of assessing the likelihood that a tumor has metastasized, the method comprising: determining the level of Heat Shock Factor-1 (HSF1) expression or the level of HSF1 activation in a sample obtained from the tumor, wherein if the level of HSF1 gene expression or HSF activation in the sample obtained from the tumor is increased, the tumor has an increased likelihood of having metastasized. In some aspects, the invention provides a method of assessing the likelihood that a tumor will metastasize, the method comprising: determining the level of HSF1 expression or the level of HSF1 activation in a sample obtained from the tumor, wherein if the level of HSF1 gene expression or HSF activation in the sample obtained from the tumor is increased, the tumor has an increased likelihood of metastasizing. In some aspects, the invention provides a method of assessing the likelihood that a tumor has metastasized, the method comprising: (a) determining the level of HSF1 expression or the level of HSF1 activation in a sample obtained from the tumor; (b) comparing the level of HSF1 expression or HSF1 activation with a control level of HSF1 gene expression or HSF1 activation, wherein a greater level of HSF1 gene expression or HSF activation in the sample obtained from the tumor as compared with a control level is indicative of a greater likelihood that the tumor has metastasized. In some aspects, the invention provides a method of assessing likelihood that a tumor will metastasized, the method comprising: (a) determining the level of HSF1 expression or the level of HSF1 activation in a sample obtained from the tumor; (b) comparing the level of HSF1 expression or HSF1 activation with a control level of HSF1 gene expression or HSF1 activation, wherein a greater level of HSF1 gene expression or HSF activation in the sample obtained from the tumor as compared with a control level is indicative of a greater likelihood that the tumor will metastasize.

An HSF1-based method of the invention may be useful for selecting a treatment regimen for a subject. For example, such results may be useful in determining whether a subject should receive, e.g., would likely benefit from, administration of one or more chemotherapeutic agents (chemotherapy), hormonal therapy, an anti-HER2 agent, or other treatment such as radiation. In some embodiments, "chemotherapeutic agent" refers to an anti-tumor agent that has cytotoxic or cytostatic properties and does not act primarily by interacting with (e.g., interfering with) a hormonal pathway that is specific or relatively specific to particular cell type(s). Exemplary chemotherapeutic agents include antimetabolites, alkylating agents, microtubule stabilizers or microtubule assembly inhibitors (e.g., taxanes or vinca alkaloids), topoisomerase inhibitors, and DNA intercalators (e.g., anthracycline antibiotics). Such agents are frequently administered systemically. Often, multiple agents are administered. Exemplary treatment regimens for breast cancer include CMF (cyclophosphamide, methotrexate, and 5-FU), AC (doxorubicin and cyclophosphamide), and anthracycline-based regimens. Capecitabine is a prodrug, that is enzymatically converted to 5-fluorouracil following administration (e.g., in tumor tissue) and is a component of a number of breast cancer treatment regimens. Tegafur is another 5-FU prodrug, which may be administered together with uracil, a competitive inhibitor of dihydropyrimidine dehydrogenase. A "hormonal therapy" (also termed "endocrine therapy") refers to an antitumor agent that acts primarily by interacting with the endocrine system, e.g., by interfering with a hormonal pathway that is active in a hormonally responsive tissue such as breast, prostate, or endometrium. Exemplary hormonal therapies include, e.g., drugs that inhibit the production or activity of hormones that would otherwise contribute to tumor cell survival, proliferation, etc. For example, in the case of breast cancer, hormonal therapy can comprise an agent that inhibits ER signaling. The agent may interact with and inhibit the ER or inhibit estrogen biosynthesis. In some embodiments hormonal therapy comprises a selective estrogen receptor modulator (SERM) such as tamoxifen, raloxifene, or toremifene. It will be appreciated that SERMs can act as ER inhibitors (antagonists) in breast tissue but, depending on the agent, may act as activators (e.g., partial agonists) of the ER in certain other tissues (e.g., bone). It will also be understood that tamoxifen itself is a prodrug that has relatively little affinity for the ER but is metabolized into active metabolites such as 4-hydroxytamoxifen (afimoxifene) and N-desmethyl-4-hydroxytamoxifen (endoxifen). Such active metabolites may be used as ER inhibitors. In some embodiments, hormonal therapy comprises a selective estrogen receptor down-regulators (SERD) such as fulvestrant or CH4986399. In some embodiments hormonal therapy comprises an agent that inhibits estrogen biosynthesis. For example, estrogen deprivation can be achieved using inhibitors that block the last stage in the estrogen biosynthetic sequence, i.e., the conversion of androgens to estrogens by the enzyme aromatase ("aromatase inhibitors"). Aromatase inhibitors include, e.g., letrozole, anastrazole, and exemestane. In the case of prostate cancer, "hormonal therapy" can comprise administering an agent that interferes with androgen receptor (AR) signaling. For example, antiandrogens are drugs that bind to and inhibit the AR, blocking the growth- and survival-promoting effects of testosterone on certain prostate cancers. Examples include flutamide and bicalutamide. Analogs of gonadotropin-releasing hormone (GnRH) can be used to suppress production of estrogen and progesterone from the ovaries, or to suppress testosterone production from the testes. Leuprolide and goserelin are GnRH analogs which are used primarily for the treatment of hormone-responsive prostate cancer.

"Adjuvant therapy" refers to administration of one or more antitumor agents in connection with, e.g., following, local therapy such as surgery and/or radiation. Adjuvant therapy may be used, e.g., when a cancer appears to be largely or completely eradicated, but there is risk of recurrence. Such therapy may help eliminate residual cells at the site of the primary tumor and/or cells that have disseminated.

"Neoadjuvant therapy" refers to adjuvant therapy administered prior to local therapy, e.g., to shrink a primary tumor.

"Anti-HER2" therapy refers to administration of an antitumor agent that acts primarily by interacting with (e.g., interfering with) HER2. Such agents may be referred to as "anti-HER2" agents. Anti-HER2 agents include, e.g., monoclonal antibodies that bind to HER2, such as trastuzumab and pertuzumab, and various small molecule kinase inhibitors that bind to HER2 and inhibits its kinase activity. Pertuzumab is a recombinant, humanized monoclonal antibody that binds to the extracellular domain II, sterically blocking homo- and heterodimerization with other ERBB receptors, thus preventing signal transduction. In some embodiments, an anti-HER2 agent inhibits HER2 and at least one other member of the human epidermal growth factor receptor family. Examples of such agents include, e.g., dual EGFR (Erb-B1) and HER2 kinase inhibitors such as lapatinib and pan-ERBB kinase inhibitors such as neratinib. In some embodiments, an anti-tumor agent is an antibody-drug conjugate (ADC). For example, an anti-HER2 antibody can be conjugated to a cytotoxic agent. Cytotoxic agents useful for such purposes include, e.g., calicheamicins, auristatins, maytansinoids, and derivatives of CC1065. For example, trastuzumab emtansine (T-DM1) is an antibody-drug conjugate ADC that combines intracellular delivery of the cytotoxic agent, DM1 (a derivative of maytansine) with the antitumor activity of trastuzumab.

In some embodiments, results of an HSF1-based assay may be useful for selecting an appropriate treatment regimen and/or for selecting the type or frequency of procedures to be used to monitor the subject for local or metastatic recurrence after therapy and/or the frequency with which such procedures are performed. For example, subjects classified as having a poor prognosis (being at high risk of poor outcome) may be treated and/or monitored more intensively than those classified as having a good prognosis. Thus any of the diagnostic, prognostic, or treatment-specific predictive methods can further comprise using information obtained from the assay to help in selecting a treatment or monitoring regimen for a subject suffering from cancer or at increased risk of cancer or at risk of cancer recurrence or in providing an estimate of the risk of poor outcome such as cancer related mortality or recurrence. The information may be used, for example, by a subject's health care provider in selecting a treatment or in treating a subject. A health care provider could also or alternatively use the information to provide a cancer patient with an accurate assessment of his or her prognosis. In some embodiments, a method of the invention can comprise making a treatment selection or administering a treatment based at least in part on the result of an HSF1-based assay. In some embodiments, a method of the invention can comprise selecting or administering more aggressive treatment to a subject, if the subject is determined to have a poor prognosis. In some embodiments, a method of the invention can comprise selecting or administering more aggressive treatment, if the subject is determined to have CIS that is positive for HSF1 expression or HSF1 activation. Often a "treatment" or "treatment regimen" refers to a course of treatment involving administration of an agent or use of a non-pharmacological therapy multiple times over a period of time, e.g., over weeks or months. A treatment can include one or more pharmacological agents (often referred to as "drugs" or "compounds") and/or one or more non-pharmacological therapies such as radiation, surgery, etc. A treatment regimen can include the identity of agents to be administered to a subject and may include details such as the dose(s), dosing interval(s), number of courses, route of administration, etc. "Monitoring regimen" refers to repeated evaluation of a subject over time by a health care provider, typically separated in time by weeks, months, or years. The repeated evaluations can be on a regular or predetermined approximate schedule and are often performed with a view to determining whether a cancer has recurred or tracking the effect of a treatment on a tumor or subject.

"More aggressive" treatment (also referred to as "intensive" or "more intensive" treatment herein) can comprise, for example, (i) administration of chemotherapy in addition to, or instead of, hormonal therapy; (ii) administration of a dose of one or more agents (e.g., chemotherapeutic agent) that is at the higher end of the acceptable dosage range (e.g., a high dose rather than a medium or low dose, or a medium dose rather than a low dose) and/or administration of a number of doses or a number of courses at the higher end of the acceptable range and/or use of non-hormonal cytotoxic/cytostatic chemotherapy; (iii) administration of multiple agents rather than a single agent; (iv) administration of more, or more intense, radiation treatments; (v) administration of a greater number of agents in a combination therapy; (vi) use of adjuvant therapy; (vii) more extensive surgery, such as mastectomy rather than breast-conserving surgery such as lumpectomy. For example, a method can comprise (i) selecting that the subject not receive chemotherapy (e.g., adjuvant chemotherapy) if the tumor is considered to have a good prognosis; or (ii) selecting that the subject receive chemotherapy (e.g., adjuvant chemotherapy), or administering such chemotherapy, if the tumor is considered to have a poor prognosis. In some embodiments, a method of the invention can comprise selecting that a subject receives less aggressive treatment or administering such treatment, if the subject is determined to have a good prognosis. "Less aggressive" (also referred to as "less intensive") treatment could entail, for example, using dose level or dose number at the lower end of the acceptable range, not administering adjuvant therapy, selecting a breast-conserving therapy rather than mastectomy, selecting hormonal therapy rather than non-hormonal cytotoxic/cytostatic chemotherapy, or simply monitoring the patient carefully. "More intensive" or "intensive" monitoring could include, for example, more frequent clinical and/or imaging examination of the subject or use of a more sensitive imaging technique rather than a less sensitive technique. "Administering" a treatment could include direct administration to a subject, instructing another individual to administer a treatment to the subject (which individual may be the subject themselves in the case of certain treatments), arranging for administration to a subject, prescribing a treatment for administration to a subject, and other activities resulting in administration of a treatment to a subject. "Selecting" a treatment or treatment regimen could include determining which among various treatment options is appropriate or most appropriate for a subject, recommending a treatment to a subject, or making a recommendation of a treatment for a subject to the subject's health care provider.

In some aspects, the invention provides a method of selecting a regimen for monitoring or treating a subject in need of treatment for cancer comprising: (a) assessing the level of HSF1 expression or HSF1 activation in a sample obtained from the subject; and (b) selecting an intensive monitoring or treatment regimen if the level of HSF1 expression or HSF1 activation is increased in the sample. In some aspects, the invention provides a method of selecting a regimen for monitoring or treating a subject in need of treatment for cancer, wherein said regimen is selected from among multiple options including at least one more intensive regimen and at least one less intensive regimen, the method comprising: (a) obtaining a classification of the subject, wherein the subject is classified into a high risk or a low risk group based at least in part on an assessment of the level of HSF1 expression or HSF1 activation in a sample obtained from the subject; and (b) selecting a more intensive regimen if the subject is classified as being in a high risk group or selecting a less intensive regimen if the subject is classified as being in a low risk group. In some aspects, the invention provides a method of monitoring or treating a subject in need of treatment for cancer comprising: (a) obtaining a classification of the subject, wherein the classification is based at least in part on an assessment of the level of HSF1 expression or HSF1 activation in a sample obtained from the subject; and (b) monitoring or treating the subject according to an intensive regimen if the subject is classified as being in a high risk group or monitoring or treating the subject with a less intensive regimen if the subject is classified as being in a low risk group. "Obtaining a classification" could comprise any means of ascertaining a classification such as performing an HSF1-based assay (or directing that an HSF1-based assay be performed) and assigning a classification based on the results, receiving results of an HSF1-based assay and assigning a classification using the results, receiving or reviewing a classification that was previously performed, etc.

In some embodiments a subject has been previously treated for the cancer, while in other embodiments the subject has not previously received treatment for the cancer. In some embodiments the previous treatment for a breast tumor is hormonal therapy such as tamoxifen or another anti-estrogen agent, e.g., another SERM.

In some embodiments, a subject falls within a selected age group or range, e.g., 40 years old or less, 50 years old or less, 55 years old or less, 60 years old or less, between 40 and 60 years of age, 40 years old or more, 50 years old or more, 55 years old or more, 60 years old or more, etc. Any age group or range may be selected in various embodiments of the invention, whether or not specifically mentioned here. In some embodiments, a female subject is pre-menopausal. In some embodiments, a female subject is post-menopausal.

In some embodiments a subject, e.g., a subject having or at risk of lung cancer or lung cancer recurrence, is a current smoker or former smoker. In some embodiments a subject, e.g., a subject having or at risk of developing lung cancer or lung cancer recurrence, is a non-smoker who has no or essentially no history of smoking.

In some embodiments, an HSF1-based method may be used to identify cancer patients that do not require adjuvant therapy, e.g., adjuvant hormonal therapy and/or adjuvant chemotherapy. For example, a prognostic method may identify patients that have a good prognosis and would be unlikely to experience clinically evident recurrence and/or metastasis even without adjuvant therapy. Since adjuvant therapy can cause significant side effects, it would be beneficial to avoid administering it to individuals whom it would not benefit. In some embodiments, an HSF1-based prognostic method of the invention may be used to identify cancer patients that have a poor prognosis (e.g., they are at high risk of recurrence and/or metastasis) and may therefore benefit from adjuvant therapy. In some embodiments, an HSF1-based prognostic method may be used to identify cancer patients that might not be considered at high risk of poor outcome based on other prognostic indicators (and may therefore not receive adjuvant therapy) but that are in fact at high risk of poor outcome, e.g., recurrence and/or metastasis. Such patients may therefore benefit from adjuvant therapy. In some embodiments, HST 1-based method may be used in a subject with cancer in whom an assessment of the tumor based on standard prognostic factors, e.g., standard staging criteria (e.g., TMN staging), histopathological grade, does not clearly place the subject into a high or low risk category for recurrence after local therapy (e.g., surgery) and/or for whom the likelihood of benefit from adjuvant therapy is unclear, as may be the case in various early stage cancers where, e.g., the cancer is small and has not detectably spread to regional lymph nodes or metastasized more remotely.

In some embodiments, an HSF1-based method may be used to provide prognostic information for a subject with a breast tumor that has one or more recognized clinicopathologic features and/or that falls into a particular class or category based on gene expression profiling. For example, breast cancers can be classified into molecular subtypes based on gene expression profiles, e.g., luminal A, luminal B, ERBB2-associated, basal-like, and normal-like (see, e.g., Sørlie, T., et al., Proc Natl Acad Sci USA. (2001) 98(19): 10869-74). Breast cancers can be classified based on a number of different clinicopathologic features such as histologic subtype (e.g., ductal; lobular; mixed), histologic grade (grade 1, 2, 3); estrogen receptor (ER) and/or progesterone receptor (PR) status (positive (+) or negative (−)), HER2 (ERBB2) expression status, and lymph node involvement. For example, the following breast cancer subtypes can be defined based on expression of estrogen receptor (ER) and human epidermal growth factor receptor 2 (HER2), e.g., as assessed by immunohistochemistry (IHC): (1) ER+, HER2+; (2) ER+, HER2; (3) ER−, HER2+; and (4) ER−, HER2−. The level of expression can be used to further divide these subtypes. Amplification of the HER2 locus can be assessed, e.g., using in situ hybridization (ISH), e.g., fluorescent in situ hybridization (FISH). In some embodiments, an HSF1-based method is applied to a tumor that is ER+. In some embodiments an HSF1-based method is applied to a tumor that is ER−. In some embodiments an HSF1-based method is applied to a tumor that is HER2+. In some embodiments an HSF1-based method is applied to a tumor that is HER2−. In some embodiments an HSF1-based method is applied to a tumor that is PR+. In some embodiments an HSF1-based method is applied to a tumor that is PR−. In some embodiments an HSF1-based method is applied to a tumor that is EGFR+. In some embodiments an HSF-based method is applied to a tumor that is EGER−. It will be understood that these markers may be present or absent in any combination in various embodiments. For example, in some embodiments an HSF1-based method is applied to a tumor that is ER+/HER2+ or ER+/HER2−(each of which categories can include tumors that are PR+ or PR− and are EGFR+ or EGFR−). In some embodiments, the sample or tumor is not "triple negative", i.e., the sample or tumor is negative for expression of ER, PR, and HER2.

In some embodiments a subject has DCIS. In some embodiments a subject has Stage I or Stage II breast cancer. In some embodiments a subject has Stage III breast cancer. In some embodiments, cancer stage is assigned using pathologic criteria, clinical criteria, or a combination of pathologic and clinical criteria.

In some embodiments a subject does not have detectable lymph node involvement, i.e., the subject is "lymph node negative" (LNN). For example, the subject may have be ER+/lymph node negative. The clinical management of subjects in this early stage group (e.g., treatment selection) is challenging due to the lack of markers indicating which small portion of the population will have a recurrence (e.g., following surgery) and could therefore benefit from more intensive monitoring and/or more aggressive treatment. In accordance with certain embodiments of the invention, a subject with ER+, LNN cancer that has increased HSF1 expression or increased HSF1 activation is monitored and/or treated more intensively than if the cancer does not have increased HSF1 expression or increased HSF1 activation.

In some embodiments, increased HSF1 expression or increased HSF1 activation in a sample from an ER+ breast tumor identifies patients having ER+ tumors that may be resistant to hormonal therapy. Such patients may benefit from use of a more aggressive treatment regimen, e.g., chemotherapy in addition to, or instead of, hormonal therapy, or more extensive surgery.

It has been reported that while about half of all breast cancers are assigned histologic grade 1 or 3 status (with a low or high risk of recurrence, respectively), a substantial percentage of tumors (30%-60%) are classified as histologic grade 2, which is less informative for clinical decision making because of intermediate risk of recurrence (Sotiriou C, et al., J Natl Cancer Inst., 98(4):262-72, 2006). Improved prognostic methods could be of significant use in this setting, for example. In some embodiments, an HSF1-based method is applied to a tumor classified as histologic grade 2, e.g., to classify histologic grade 2 tumors into high and low risk groups. In some embodiments, an HSF1-based method is applied to a tumor classified as histologic grade 2, e.g., to classify histologic grade 2 tumors into higher and lower risk groups, wherein tumors that have increased HSF1 expression or HSF1 activation are classified into the higher risk group. Tumors that do not have increased HSF1 expression or HSF1 activation would be classified into the lower risk group.

In some embodiments, an HSF1-based assay is used to provide sample classification, diagnostic, prognostic, or treatment-predictive information pertaining to lung cancer, e.g., non-small cell lung cancer (NSCLS), such as a lung adenocarcinoma. In some embodiments, the lung cancer, e.g., lung adenocarcinoma, is a Stage I cancer (T1 N0 M0 or T2 N0 M0). In some embodiments the cancer is a Stage IA lung cancer (T1N0M0). In some embodiments the cancer is a Stage IB lung cancer (T1N0M0). In some embodiments, the lung cancer, e.g., lung adenocarcinoma, is a Stage II cancer. Stage I and II lung cancers are typically treated by surgical resection of the tumor. Although surgery can be curative, a significant fraction of patients develop recurrence or metastases. Such patients might benefit from adjuvant therapy (radiation and/or chemotherapy). However, the current standard staging system (TMN) cannot predict which stage I or II lung cancers will recur. Although studies have shown adjuvant chemotherapy to be of benefit in groups of patients with stage II lung cancer, its role in treating stage I lung cancer is unclear. Without wishing to be bound by any theory, the number of patients diagnosed with stage I or II lung cancer may increase significantly at least in part due to the increased use of imaging modalities such as computed tomography (CT) scans for screening purposes, e.g., in individuals who have a significant smoking history. It would be useful to be able to identify those patients with stage I or stage II cancer who are at increased likelihood of recurrence and may therefore be more likely to benefit from adjuvant chemotherapy. In some embodiments, an HSF1-based method is applied to classify a stage I or stage II lung tumor into a higher or lower risk group, wherein tumors that have increased (e.g., high or intermediate) HSF1 expression or HSF1 activation are classified into the higher risk group. Tumors that have absent or low HSF1 expression or HSF1 activation are classified into the lower risk group. Subjects with tumors classified into the higher risk group have an increased likelihood of recurrence than subjects with tumors classified into the lower risk group and may benefit from adjuvant chemotherapy. Subjects with tumors classified into the lower risk group may be treated with surgery alone. Adjuvant chemotherapy for operable lung cancer frequently includes a platinum-based agent (e.g., cisplatin or carboplatin), optionally in combination with an anti-mitotic agent (e.g., an anti-microtubule agent) such as a taxane (e.g., paclitaxel (Taxol) or docetaxel (Taxotere)) or a vinca alkaloid such as vinblastine, vincristine, vindesine and vinorelbine. Other agents that may be administered as adjuvant chemotherapy in operable lung cancer, typically in combination with a platinum agent, include mitomycin, doxorubicin, or etoposide. Other adjuvant chemotherapy regiments include tegafur alone, uracil alone, a combination of tegafur and uracil, or a combination of tegafur and/or uracil with a platinum agent.

In some embodiments a subject has been previously treated for the cancer, while in other embodiments the subject has not previously received treatment for the cancer. In some embodiments the previous treatment for a breast tumor is hormonal therapy such as tamoxifen or another anti-estrogen agent, e.g., another SERM.

In some embodiments, a subject falls within a selected age group or range, e.g., 40 years old or less, 50 years old or less, 55 years old or less, 60 years old or less, between 40 and 60 years of age, 40 years old or more, 50 years old or more, 55 years old or more, 60 years old or more, etc. Any age group or range may be selected in various embodiments of the invention, whether or not specifically mentioned here. In some embodiments, a female subject is pre-menopausal. In some embodiments, a female subject is post-menopausal.

In some embodiments a subject, e.g., a subject having or at risk of lung cancer or lung cancer recurrence, is a current smoker or former smoker. In some embodiments a subject, e.g., a subject having or at risk of developing lung cancer or lung cancer recurrence, is a non-smoker who has no or essentially no history of smoking.

Any method of the invention that comprises assessing HSF1 expression or HSF1 activation or using the level of expression or activation of an HSF1 gene product may, in certain embodiments, further comprise assessing or using the level of expression, activation, or activity of one or more additional cancer biomarkers. In certain embodiments, the level of expression, activation, or activity of an HSF1 gene product is used in conjunction with the level of expression, activation, or activity of one or more additional cancer biomarkers in a method of providing diagnostic, prognostic, or treatment-specific predictive information. The additional cancer biomarker(s) may be selected based at least in part on the site in the body from which a sample was obtained or the suspected or known tissue of origin of a tumor. For example, in the case of suspected or known breast cancer, one or more breast cancer biomarkers may be assessed.

In some embodiments, an HSF1-based assay is used together with additional information, such as results of a second assay (or multiple assays) and/or clinicopathological information to provide diagnostic, prognostic, or treatment-predictive information pertaining to breast cancer. In some embodiments, such information comprises, e.g., subject age, tumor size, nodal involvement, tumor histologic grade, ER status, PR status, and/or HER2 status, menopausal status, etc.). In some embodiments, the additional information includes the PR status of the tumor. For example, a method can comprise determining the PR status of a tumor and, if the PR status is positive, classifying the tumor with respect to prognosis or treatment selection based on expression of HSF1 or activation of HSF1. In some embodiments, information from an HSF1-related assay is used together with a decision making or risk assessment tool such as the computer program Adjuvant! Online (https://www.adjuvantonline.com/index.jsp). The basic format of an early version of Adjuvant! was described in the article Ravdin, Siminoff, Davis, et al. JCO 19(4) 980-991, 2001. In some embodiments, the second assay is a gene expression profiling assay such as the MammaPrint® (Agendia BV, Amsterdam, the Netherlands), Oncotype DX™ (Genomic Health, Redwood City, Calif.), Celera Metastasis Score™ (Celera, Inc., Rockville, Md.), Breast BioClassifier (ARUP, Salt Lake City, Utah), Rotterdam signature 76-gene panel (Erasmus University Cancer Center, Rotterdam, The Netherlands), MapQuant Dx™ Genomic Grade test (Ipsogen, Stamford, Conn.), Invasiveness Gene Signature (OncoMed Pharmaceuticals, Redwood City, Calif.), NuvoSelect™ assay (Nuvera Biosciences, Woburn, Mass.), THEROS Breast Cancer IndexSM (BCI) (bioTheranostics, San Diego) that classifies tumors (e.g., into high or low risk groups) based on expression level of multiple genes using, e.g., a microarray or multiplex RT-polymerase chain reaction (PCR) assay. The phrase "used together" with in regard to two or more assays means that the two or more assays are applied to a particular tumor. In some embodiments, the two or more assays are applied to the same sample (or a portion thereof) obtained from the tumor.

In some embodiments, an HSF1-based assay may be used together with a gene expression profile in which expression level of at least 1, at least 5, or at least 10 different genes ("classifier genes") is used to classify a tumor. It will be understood that such gene expression profile assays may measure expression of control genes as well as classifier genes. In some embodiments an HSF1-based assay is used together with an H:I™ test (bioTheranostics, Carlsbad, Calif.), in which the ratio of expression of HOXB 13 and IL-17B genes is used to classify a tumor. In some embodiments, an HSF1-based assay is used together with an antibody-based assay, e.g., the ProEx™ Br (TriPath Oncology, Durham, N.C.), Mammostrat® (Applied Genomics, Inc., Huntsville, Ala.), ADH-5 (Atypical Ductal Hyperplasia) Breast marker antibody cocktail (Biocare Medical, Concord, Calif.), measurement of urokinase-like plasminogen activator (uPA) and/or its inhibitor plasminogen activator inhibitor 1 (PAI1), or a FISH-based test such as the eXaagenBC™ (eXagen Diagnostics, Inc., Albuquerque, N. Mex.). In some embodiments, an HSF1-based assay is used together with an assay that measures proliferation. For example, expression of a proliferation marker such as Ki67 (Yerushalmi et al., Lancet Oncol. (2010), 11(2):174-83) can be used. In some embodiments, an HSF1-based assay is used together with a miRNA-based assay (e.g., an assay that measures expression of one or more miRNAs or miRNA precursors). For example, in some embodiments, an HSF1-based assay is used together with a miR31-based assay, e.g., as described in PCT/US2009/067015 (WO/2010/065961).

An HSF1-based assay (e.g., any of the HSF1-based assays described herein) may be used together with another assay in any of a number of ways in various embodiments of the invention. For example, in some embodiments, if results of two tests are discordant (e.g., one test predicts that the subject is at high risk while the other predicts that the subject is at low risk), the subject may receive more aggressive therapeutic management than if both tests predict low risk. In some embodiments, if a result of a non-HSF1-based assay is inconclusive or indeterminate, an HSF1-based assay can be used to provide a diagnosis, prognosis, or predictive information. In some embodiments, one can have increased confidence if results of an HSF1-based assay and a second assay are in agreement. For example, if both tests indicate that the subject is at low risk, there can be increased confidence in the appropriateness of providing less aggressive therapeutic management, e.g., to not administer adjuvant chemotherapy, while if both tests indicate that the subject is at high risk, there can be increased confidence in the appropriateness of providing more aggressive therapeutic management.

In some embodiments, a method of the invention comprises providing treatment-specific predictive information relating to use of a proteostasis modulator to treat a subject with cancer, based at least in part on assessing the level of expression of HSF1 or activation of HSF1 in a sample obtained from the subject. "Proteostasis" (which term is used interchangeably with "protein homeostasis") refers to controlling the concentration, conformation (e.g., folding), binding interactions (quaternary structure), and subcellular location of the proteins within a cell, often through mechanisms such as transcriptional and/or translational changes, chaperone-assisted folding and disaggregation, or controlled protein degradation. Proteostasis can be thought of as a network comprising multiple distinguishable pathways ("proteostasis pathways") that may interact with and influence each other. Proteostasis pathways include, e.g., the HSR (discussed above), the ubiquitination-proteasome degradation pathway, and the unfolded protein response (UPR). "Proteostasis modulator" refers to an agent that modulates one or more proteostasis pathways.

In some embodiments, a sample can be classified as belonging to (i.e., obtained from) a subject with cancer who is a suitable candidate for treatment with a proteostasis modulator. For example, the invention provides a method of determining whether a subject with cancer is a suitable candidate for treatment with a proteostasis modulator, comprising assessing the level of HSF1 expression or HSF1 activation in a sample obtained from the subject, wherein an increased level of HSF1 expression or an increased level of HSF1 activation in the sample is indicative that the subject is a suitable candidate for treatment with a proteostasis modulator. In some embodiments, the invention provides a method of determining whether a subject with cancer is likely to benefit from treatment with a proteostasis modulator, comprising: assessing the level of HSF1 expression or HSF1 activation in a sample obtained from the subject, wherein an increased level of HSF1 expression or an increased level of HSF1 activation in the sample is indicative that the subject is likely to benefit from treatment with a proteostasis modulator. In some embodiments, the invention provides a method of identifying a subject with cancer who is likely to benefit from treatment with a proteostasis modulator, comprising assessing the level of HSF1 expression or HSF1 activation in a sample obtained from the subject, wherein an increased level of HSF1 expression or an increased level of HSF1 activation in the sample identifies the subject as being likely to benefit from treatment with a proteostasis modulator. In some embodiments, the invention provides a method of predicting the likelihood that a tumor will be sensitive to a protein homeostasis modulator, the method comprising: assessing the level of HSF1 expression or the level of HSF1 activation in a sample obtained from the tumor; wherein if the level of HSF1 expression or activation is increased, the tumor has an increased likelihood of being sensitive to the protein homeostasis modulator. A tumor is "sensitive" to a treatment if the subject experiences a partial or complete response or stabilization of disease following treatment. Response can be assessed, for example, by objective criteria such as anatomical tumor burden, as known in the art. In some embodiments, a response correlates with increased progression-free survival or increased overall survival. Thus in some embodiments, a tumor is sensitive to a treatment if administration of the treatment correlates with increased progression-free survival or increased overall survival.

In some embodiments, treatment with a proteostasis modulator comprises administering a proteostasis modulator to the subject in addition to a standard treatment regimen for treating the subject's cancer. It will be understood that the proteostasis modulator is typically administered in an effective amount in a suitable pharmaceutical composition that may comprise one or more pharmaceutically acceptable carriers. "Pharmaceutically acceptable carrier" refers to a diluent, excipient, or vehicle with which the therapeutically active agent is administered. An effective amount may be administered in one dose or multiple doses.

Without wishing to be bound by any theory, increased HSF1 activity may help tumor cells cope with the stress of therapy (e.g., pharmacological agents, radiation, etc.) and/or may promote phenotypic diversity among tumor cells by helping tumor cells cope with the consequences of mutations. Such effects may contribute to poor outcomes in cancer by, for example, promoting emergence of malignant or more aggressive tumor subclones and/or promoting treatment resistance. Administration of a proteostasis modulator may counteract such effects. In some embodiments, a therapeutic benefit could result at least in part from a proteostasis modulator reducing the likelihood that a tumor will become resistant to such treatment or at least in part reversing resistance that may be present at the time of treatment. For example, addition of a proteostasis modulator to a standard chemotherapy or hormonal regimen for breast cancer may reduce the likelihood that a tumor will become resistant to such regimen, or at least in part reverse resistance that may be present at the time of treatment. Based at least in part on the discovery that HSF1 expression and HSF1 activation are increased in pre-invasive cancer, the invention encompasses the recognition that intervention at the pre-invasive stage of cancer with a proteostasis modulator (e.g., to counteract HSF1's activity) may delay or reduce the likelihood of progression to invasive cancer. In some aspects, the invention encompasses the recognition that treatment of subjects without evidence of cancer (e.g., subjects at increased risk of cancer) with a proteostasis modulator (e.g., to counteract HSF1's activity) may inhibit or reduce the likelihood that the subject will develop cancer. It should be noted that a subject may be a suitable candidate for treatment with a proteostasis modulator even if the tumor does not exhibit increased HSF1 expression or increased HSF1 activation. For example, subjects with early stage cancer that has not progressed to a state in which HSF1 is activated may benefit In some aspects, the invention provides a method of treating a subject who has pre-invasive cancer, the method comprising administering a proteostasis modulator to a subject with pre-invasive cancer. Such treatment may, for example, inhibit progression of the pre-invasive cancer to invasive cancer. In some aspects, the invention provides a method of treating a subject at increased risk of cancer, the method comprising administering a proteostasis modulator to the subject. In some aspects, the invention provides a method of inhibiting development of cancer in a subject, the method comprising administering a proteostasis modulator to the subject.

In some aspects, the invention provides a method of inhibiting recurrence of cancer in a subject, the method comprising administering a proteostasis modulator to the subject. In some embodiments, the cancer is characterized by increased HSF1 expression or increased HSF1 activation.

In some aspects, the invention provides a method of inhibiting emergence of resistance to therapy in a subject with cancer, the method comprising administering a proteostasis modulator to the subject in combination with an additional therapy, thereby reducing the likelihood of resistance to the additional therapy. In some embodiments, the additional therapy is a chemotherapeutic agent. In some embodiments, the additional therapy is a hormonal agent. In some embodiments, the cancer is characterized by increased HSF1 expression or increased HSF1 activation.

In some embodiments, a proteostasis modulator is an HSR modulator, e.g., an HSR inhibitor. "HSR inhibitor" refers to an agent that inhibits expression or activity of at least one component of the HSR. HSR components include, e.g., HSF1 itself and heat shock proteins such as HSP 40, HSP70, and HSP90. In some embodiments, the component of the HSR is HSP90. For purposes of the present invention, HSP90 refers to HSP90A family HSP90, commonly referred to in the art as "cytoplasmic HSP90" (see Taipale, M, et al., Nat. Rev. Mol. Cell. Biol. (2010) 11(7):515-28 for review). Most vertebrates, including humans, have two genes encoding HSP90A proteins with very similar sequences and highly overlapping functions: HSP90AA1 (Gene ID for human gene: 3320; Gene ID for mouse ortholog: 15519) and HSP90AB1 (Gene ID for human gene: 3326; Gene ID for mouse gene: 15516). The proteins encoded by HSP90AA1 and HSP90AB1 are referred to as HSP90α and HSP90β, respectively. For purposes of the present invention, an "HSP90 inhibitor" refers to a compound that inhibits at least one HSP90A, e.g., HSP90β. In some embodiments, the compound inhibits both HSP90α and HSP90β. HSP90A is an ATPase and contains three main structural domains: a highly conserved N-terminal (NTD) domain of ~25 kDa, which contains a binding pocket for ATP; a middle domain (MD) of ~40 kDa, and a C-terminal domain (CTD) of ~12 kDa. HSP90A forms homodimers and undergoes a dynamic cycle termed the "chaperone cycle" involving ATP binding and hydrolysis, during which it undergoes conformational shifts that are important in its recognition and release of client proteins.

Numerous HSP90 inhibitors are known in the art. In general, an HSP90 inhibitor can inhibit HSP90 activity in any of a variety of ways, such as by inhibiting the ATPase activity of HSP90. In some embodiments an HSP90 inhibitor specifically binds to the ATP binding pocket of HSP90. In some embodiments an HSP90 inhibitor binds outside the ATP binding pocket. A number of HSP90 inhibitors have shown promise in the treatment of cancer, and others are under investigation. Exemplary HSP90 inhibitors include, e.g., benzoquinone ansamycins such as geldanamycin and herbimycin, resorcylic acid lactones such as radicicol, purine scaffold compounds, and a variety of synthetic compounds based on other chemical scaffolds (see, e.g., Taldone, T., et al. Bioorg Med. Chem., 17(6):2225-35, 2009 or Trepel, J., et al., Nat Rev Cancer.10(8):537-49, 2010). Exemplary HSP90 inhibitors that have entered clinical development (i.e., they have been administered to at least one human subject in a clinical trials) include, e.g., geldanamycin analogs such as 17-allylamino-17-demethoxygeldanamycin (17-AAG, also called tanespimycin), 17-dimethylaminoethylamino-17-demethoxygeldanamycin (17-DMAG), retaspimycin (IPI-504), alvespimycin (IPI-493), SNX-5422, AUY922, STA-9090, HSP990, CNF2024 (BIIB021), XL888, AT13387, and MPC-3100.

An ongoing challenge in the development of HSP90 inhibitors has been the identification of which patients are likely to benefit from treatment with these drugs (36-39). The basal level of HSP90 in tumors per se has generally not proven to be predictive. Without wishing to be bound by any theory, the effectiveness of HSF1, even as a single marker, in predicting the outcome of cancers as described herein may reflect the fact that HSF1, as a dominant regulator of the entire heat shock network, serves as a better indicator of the overall stress levels within a tumor and consequently the "load" on the HSP-based chaperone machinery. In accordance with certain aspects of the invention, this load could determine which patients might benefit from a HSP90 inhibitor, either alone or in combination with other agents. In some embodiments, the HSP90 inhibitor has entered clinical development for, e.g., treatment of cancer. In some embodiments the HSP90 inhibitor is a small molecule.

In some embodiments, a proteostasis modulator is an HSF1 inhibitor. As used herein, an "HSF1 inhibitor" is an agent that inhibits expression or activity of HSF1. In some embodiments, an HSF1 inhibitor is an RNAi agent, e.g., a short interfering RNA (siRNA) or short hairpin RNA (shRNA) that, when present in a cell (e.g., as a result of exogenous introduction of an siRNA or intracellular expression of a shRNA) results in inhibition of HSF expression by RNA interference (e.g., by causing degradation or translational repression of mRNA encoding HSF1, mediated by the RNAi-induced silencing complex). Exemplary RNAi agents that inhibit HSF1 expression are disclosed, e.g., in PCT/EP2010/069917 (WO/2011/073326) or in reference 6. In some embodiments an HSF1 inhibitor may be an intrabody that binds to HSF1, or an agent such as a single chain antibody, aptamer, or dominant negative polypeptide that binds to HSF1, wherein the agent optionally comprises a moiety that allows it to gain entry into tumor cells. For example, the agent may comprise a protein transduction domain that allows the agent to cross the plasma membrane or a ligand that binds to a cell surface receptor such that the agent is internalized, e.g., by endocytosis. In some embodiments the HSF1 inhibitor comprises a small molecule. In some embodiments the HSF1 inhibitor comprises an agent that inhibits activation of HSF1. For example, the agent may at least in part block assembly of multimers, e.g., trimers, comprising HSF1. Suitable agents for inhibiting HSF1 may be identified using a variety of screening strategies.

In some embodiments, a proteostasis modulator is a proteasome inhibitor. The proteasome is a large, multi-protein complex that unfolds and proteolyses substrate polypeptides, reducing them to short fragments (Lodish, et al., supra). Most protein degradation by the proteasome occurs via the ubiquitination-proteasome degradation pathway (UPD pathway), a multistep enzymatic cascade in eukaryotes in which ubiquitin is conjugated via a lysine residue to target proteins for destruction. Proteins tagged with lysine-linked chains of ubiquitin are marked for degradation in the proteasome. Proteasome-mediated protein degradation, e.g., via the UPD pathway, allows cells to eliminate excess and misfolded proteins and regulates various biological processes, such as cell proliferation. "Proteasome inhibitor" refers to an agent that inhibits activity of the proteasome or inhibits synthesis of a proteasome componnet. Proteasome inhibitors include, e.g., a variety of peptidic and non-peptidic agents that bind reversibly to the proteasome, bind covalently to the active site of the proteasome, or bind to the proteasome outside the active site (sometimes termed "allosteric inhibitors") (Ruschak A M, et al., J Natl Cancer Inst. (2011) 103(13):1007-17). A number of proteasome inhibitors have shown promise in the treatment of cancer, including bortezomib (Velcade®) (approved by the US FDA), and various others under investigation. Exemplary proteasome inhibitors that have been tested in clinical trials in cancer include bortezomib, CEP-18770, MLN-9708, carfilzomib, ONX 0912, and NPI-0052 (salinosporamide A). HIV protease inhibitors such as nelvinavir also inhibit the proteasome. Other agents that inhibit the proteasome include chloroquine, 5-amino-8-hydroxyquinoline (5AHQ), disulfuram, tea polyphenols such as epigallocatechin-3-gallate, MG-132, PR-39, PS-I, PS-IX, and lactacystin. In some embodiments, a method of the invention is applied with regard to proteasome inhibitor that has entered clinical development for, e.g., treatment of cancer.

In some aspects, the invention encompasses use of a method comprising assessing the level of HSF1 expression or HSF1 activation as a "companion diagnostic" test to determine whether a subject is a suitable candidate for treatment proteostasis modulator. In some embodiments a proteostasis modulator may be approved (allowed to be sold commercially for treatment of humans or for veterinary purposes) by a government regulatory agency (such as the US FDA, the European Medicines Agency (EMA), or government agencies having similar authority over the approval of therapeutic agents in other jurisdictions) with the recommendation or requirement that the subject is determined to be a suitable candidate for treatment with the proteostasis modulator based at least in part on assessing the level of HSF1 expression or HSF1 activation in a tumor sample obtained from the subject. For example, the approval may be for an "indication" that includes the requirement that a subject or tumor sample be classified as having high levels or increased levels of HSF1 expression or HSF1 activation. Such a requirement or recommendation may be included in the package insert provided with the agent. In some embodiments a particular method for detection or measurement of an HSF1 gene product or of HSF1 activation or a specific test reagent (e.g., an antibody that binds to HSF1 polypeptide or a probe that hybridizes to HSF1 mRNA) or kit may be specified. In some embodiments, the method, test reagent, or kit will have been used in a clinical trial whose results at least in part formed the basis for approval of the proteostasis modulator. In some embodiments, the method, test reagent, or kit will have been validated as providing results that correlate with outcome of treatment with the proteostasis modulator.

In some aspects, the invention provides a method of assessing efficacy of treatment of cancer comprising: (a) assessing the level of HSF1 expression or HSF1 activation in a sample obtained from a subject that has been treated for cancer, wherein absence of increased HSF1 expression or increased HSF1 activation in said sample indicates effective treatment. In some embodiments, step (a) is repeated at one or more time points following treatment of the subject for cancer, wherein continued absence of increased HSF1 expression or increased HSF1 activation of over time indicates effective treatment. The sample may be obtained, for example, from or close to the site of a cancer that was treated (e.g., from or near a site from which a tumor was removed).

In some aspects, the invention provides a method of assessing efficacy of treatment of cancer comprising: (a) assessing the level of HSF1 expression or HSF1 activation in a sample obtained from a subject having cancer, and (b) repeating step (a) at one or more time points during treatment of the subject for cancer, wherein decreased HSF1 expression or decreased HSF1 activation of over time indicates effective treatment. The sample may be obtained, for example, from or close to the site of a cancer being treated.

In some aspects, the invention provides a method of monitoring a subject for cancer recurrence comprising: (a) assessing the level of HSF1 expression or HSF1 activation in a sample obtained from a subject that has been treated for cancer, wherein presence of increased HSF1 expression or increased HSF1 activation in the sample indicates cancer recurrence. In some embodiments, step (a) is repeated at one or more time points following treatment of the subject for cancer. The sample may be obtained, for example, from or close to the site of a cancer that was treated (e.g., from or near a site from which a tumor was removed).

In certain embodiments of any aspect of the invention, a cancer is breast cancer. In certain aspects, the invention provides the recognition that assessment of HSF1 expression or activation for diagnostic, prognostic, or predictive purposes may be of particular use in estrogen receptor (ER) positive breast cancer. In certain embodiments of any of the inventive methods relating to breast cancer, the breast cancer is estrogen receptor (ER) positive breast cancer.

Certain aspects and embodiments of the invention are described herein mainly in regard to breast cancer (e.g., breast tumor cells, breast tumor samples, breast tumors, and/or subjects in need of prognosis, diagnosis, or treatment selection for breast cancer). It will be understood that the invention encompasses embodiments in which products and processes described herein are applied in the context of tumors arising from organs or tissues other than the breast. One of ordinary skill in the art will recognize that certain details of the invention may be modified according, e.g., to the particular tumor type or tumor cell type of interest. Such embodiments are within the scope of the invention.

It will be understood that many of the methods provided herein, e.g., methods of classification, may be described in terms of samples, tumors, or subjects and such descriptions maybe considered equivalent and freely interchangeable. For example, where reference is made herein to a method of classifying a sample, such method may be expressed as a method of classifying a tumor from which the sample was obtained or as a method of classifying a subject from which the sample originated in various embodiments. Similarly, where reference is made herein to assessing the level of HSF1 expression or HSF1 activation in a sample, such method may be expressed as a method of assessing the level of HSF1 expression or HSF1 activation in a tumor from which the sample was obtained in various embodiments. It will also be understood that a useful diagnostic, prognostic, or treatment-specific predictive method need not be completely accurate. For example, "predicting", "predicting the likelihood", and like terms, as used herein, do not imply or require the ability to predict with 100% accuracy and do not imply or require the ability to provide a numerical value for a likelihood (although such value may be provided). Instead, such terms typically refer to forecast of an increased or a decreased probability that a result, outcome, event, etc., of interest exists or will occur, e.g., when particular criteria or conditions exist, as compared with the probability that such result, outcome, or event, etc., exists or will occur when such criteria or conditions are not met.

Methods of Assessing HSF1 Expression or HSF1 Activation

HSF1 genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Exemplary databases include, e.g., GenBank, RefSeq, Gene, UniProtKB/SwissProt, UniProtKB/Trembl, and the like. The HSF1 gene has been assigned NCBI GeneID: 3297. The NCBI Reference Sequence accession numbers for human HSF1 mRNA and polypeptide are NM_005526 and NP_005517, respectively, and the human HSF1 polypeptide GenBank acc. no. is AAA52695.1. The human HSF1 gene is located on chromosome 8 (8q24.3), RefSeq accession number NC_000008.10. Sequences of other nucleic acids and polypeptides of interest herein could also be readily obtained from such databases. Sequence information may be of use, for example, to generate reagents for detection of HSF1 gene products.

In general, the level of HSF1 expression of HSF1 activation can be assessed using any of a variety of methods. In many embodiments, the level of HSF1 expression is assessed by determining the level of an HSF1 gene product in a sample obtained from a tumor. In some embodiments an HSF1 gene product comprises HSF1 mRNA. In general, any suitable method for measuring RNA can be used to measure the level of HSF1 mRNA in a sample. For example, methods based at least in part on hybridization and/or amplification can be used. Exemplary methods of use to detect mRNA include, e.g., in situ hybridization, Northern blots, microarray hybridization (e.g., using cDNA or oligonucleotide microarrays), reverse transcription PCR (e.g., real-time reverse transcription PCR), nanostring technology (see, e.g., Geiss, G., et al., Nature Biotechnology (2008), 26, 317-325; U.S. Ser. No. 09/898,743 (U.S. Pat. Pub. No. 20030013091) for exemplary discussion of nanostring technology and general description of probes of use in nanostring technology). A number of such methods include contacting a sample with one or more nucleic acid probe(s) or primer(s) comprising a sequence (e.g., at least 10 nucleotides in length, e.g., at least 12, 15, 20, or 25 nucleotides in length) substantially or perfectly complementary to a target RNA (e.g., HSF1 mRNA). The probe or primer is often detectably labeled using any of a variety of detectable labels. In many embodiments the sequence of the probe or primer is sufficiently complementary to HSF1 mRNA to allow the probe or primer to distinguish between HSF1 mRNA and most or essentially all (e.g., at least 99%, or more) transcripts from other genes in a mammalian cell, e.g., a human cell, under the conditions of an assay. In some embodiments, "substantially complementary" refers to at least 90% complementarity, e.g., at least 95%, 96%, 97%, 98%, or 99% complementarity. A probe or primer may also comprise sequences that are not complementary to HSF1 mRNA, so long as those sequences do not hybridize to other transcripts in a sample or interfere with hybridization to HSF1 mRNA under conditions of the assay. Such additional sequences may be used, for example, to immobilize the probe or primer to a support. A probe or primer may be labeled and/or attached to a support or may be in solution in various embodiments. A support may be a substantially planar support that may be made, for example, of glass or silicon, or a particulate support, e.g., an approximately spherical support such as a microparticle (also referred to as a "bead" or "microsphere"). In some embodiments, a sequencing-based approach such as serial analysis of gene expression (SAGE) (including variants thereof) or RNA-Sequencing (RNA-Seq) is used. RNA-Seq refers to the use of any of a variety of high throughput sequencing techniques to quantify RNA transcripts (see, e.g., Wang, Z., et al. Nature Reviews Genetics (2009), 10, 57-63). Other methods of use for detecting RNA include, e.g., electrochemical detection, bioluminescence-based methods, fluorescence-correlation spectroscopy, etc. It will be understood that certain methods that detect mRNA may, in some instances, also detect at least some pre-mRNA transcript(s), transcript processing intermediates, and degradation products of sufficient size. It will also be understood that a probe or primer may in some embodiments be substantially or perfectly complementary to a complement of HSF1 RNA.

In some embodiments an HSF1 gene product comprises HSF1 polypeptide. In general, any suitable method for measuring proteins can be used to measure the level of HSF1 polypeptide in a sample. In many embodiments, an immunological method or other affinity-based method is used. In general, immunological detection methods involve detecting specific antibody-antigen interactions in a sample such as a tissue section or cell sample. The sample is contacted with an antibody that binds to the target antigen of interest. The antibody is then detected using any of a variety of techniques. In some embodiments, the antibody that binds to the antigen (primary antibody) or a secondary antibody that binds to the primary antibody has been tagged or conjugated with a detectable label. In some embodiments a label-free detection method is used. A detectable label may be, for example, a fluorescent dye (e.g., a fluorescent small molecule) or quencher, colloidal metal, quantum dot, hapten, radioactive atom or isotope, or enzyme (e.g., peroxidase). It will be appreciated that a detectable label may be directly detectable or indirectly detectable. For example, a fluorescent dye would be directly detectable, whereas an enzyme may be indirectly detectable, e.g., the enzyme reacts with a substrate to generate a directly detectable signal. Numerous detectable labels and strategies that may be used for detection, e.g., immunological detection, are known in the art. Exemplary immunological detection methods include, e.g., immunohistochemistry (IHC); enzyme-linked immunosorbent assay (ELISA), bead-based assays such as the Luminex® assay platform (Invitrogen), flow cytometry, protein microarrays, surface plasmon resonance assays (e.g., using BiaCore technology), microcantilevers, immunoprecipitation, immunoblot (Western blot), etc. IHC generally refers to immunological detection of an antigen of interest (e.g., a cellular constituent) in a tissue sample such as a tissue section. As used herein, IHC is considered to encompass immunocytochemistry (ICC), which term generally refers to the immunological detection of a cellular constituent in isolated cells that essentially lack extracellular matrix components and tissue microarchitecture that would typically be present in a tissue sample. Traditional ELISA assays typically involve use of primary or secondary antibodies that are linked to an enzyme, which acts on a substrate to produce a detectable signal (e.g., production of a colored product) to indicate the presence of antigen or other analyte. IHC generally refers to the immunological detection of a tissue or cellular constituent in a tissue or cell sample comprising substantially intact (optionally permeabilized) cells. As used herein, the term "ELISA" also encompasses use of non-enzymatic reporters such as fluorogenic, electrochemiluminescent, or real-time PCR reporters that generate quantifiable signals. It will be appreciated that the term "ELISA" encompasses a number of variations such as "indirect", "sandwich", "competitive", and "reverse" ELISA.

In some embodiments, e.g., wherein IHC is used for detecting HSF1, a sample is in the form of a tissue section, which may be a fixed or a fresh (e.g., fresh frozen) tissue section or cell smear in various embodiments. A sample, e.g., a tissue section, may be embedded, e.g., in paraffin or a synthetic resin or combination thereof. A sample, e.g., a tissue section, may be fixed using a suitable fixative such as a formalin-based fixative. The section may be a paraffin-embedded, formalin-fixed tissue section. A section may be deparaffinized (a process in which paraffin (or other substance in which the tissue section has been embedded) is removed (at least sufficiently to allow staining of a portion of the tissue section). To facilitate the immunological reaction of antibodies with antigens in fixed tissue or cells it may be helpful to unmask or "retrieve" the antigens through pretreatment of the sample. A variety of antigen retrieval procedures (sometimes called antigen recovery), can be used in IHC. Such methods can include, for example, applying heat (optionally with pressure) and/or treating with various proteolytic enzymes. Methods can include microwave oven irradiation, combined microwave oven irradiation and proteolytic enzyme digestion, pressure cooker heating, autoclave heating, water bath heating, steamer heating, high temperature incubator, etc. To reduce background staining in IHC, the sample may be incubated with a buffer that blocks the reactive sites to which the primary or secondary antibodies may otherwise bind. Common blocking buffers include, e.g., normal serum, non-fat dry milk, bovine serum albumin (BSA), or gelatin, and various commercial blocking buffers. The sample is then contacted with an antibody that specifically binds to the antigen whose detection is desired (e.g., HSF1 protein). After an appropriate period of time, unbound antibody is then removed (e.g., by washing) and antibody that remains bound to the sample is detected. After immunohistochemical staining, a second stain may be applied, e.g., to provide contrast that helps the primary stain stand out. Such a stain may be referred to as a "counterstain". Such stains may show specificity for discrete cellular compartments or antigens or stain the whole cell. Examples of commonly used counterstains include, e.g., hematoxylin, Hoechst stain, or DAPI. The tissue section can be visualized using appropriate microscopy, e.g., light microscopy, fluorescence microscopy, etc. In some embodiments, automated imaging system with appropriate software to perform automated image analysis is used.

In some embodiments, flow cytometry (optionally including cell sorting) is used to detect HSF1 expression. The use of flow cytometry would typically require the use of isolated cells substantially removed from the surrounding tissue microarchitecture, e.g., as a single cell suspension. HSF1 mRNA or polypeptide level could be assessed by contacting cells with a labeled probe that binds to HSF1 mRNA or a labeled antibody that binds to HSF1 protein, respectively, wherein said probe or antibody is appropriately labeled (e.g., with a fluorophore, quantum dot, or isotope) so as to be detectable by flow cytometry. In some embodiments, cell imaging can be used to detect HSF1.

In some embodiments, an antibody for use in an immunological detection method, e.g., IHC, is monoclonal. In some embodiments an antibody is polyclonal. In some embodiments, an antibody is a preparation that comprises multiple monoclonal antibodies. In some embodiments, the monoclonal or polyclonal antibodies have been generated using the same portion of HSF1 (or full length HSF) as an immunogen or binding target. In some embodiments, an antibody is an anti-peptide antibody. In some embodiments, a monoclonal antibody preparation may comprise multiple distinct monoclonal antibodies generated using different portions of HSF1 as immunogens or binding targets. Many antibodies that specifically bind to HSF1 are commercially available and may be used in embodiments of the present invention. One of ordinary skill in the art would readily be able to generate additional antibodies suitable for use to detect HSF1 polypeptide using standard methods.

In some embodiments, a ligand that specifically binds to HSF1 but is not an antibody is used as an affinity reagent for detection of HSF1. For example, nucleic acid aptamers or certain non-naturally occurring polypeptides structurally unrelated to antibodies based on various protein scaffolds may be used as affinity reagents. Examples include, e.g., agents referred to in the art as affibodies, anticalins, adnectins, synbodies, etc. See, e.g., Gebauer, M. and Skerra, A., Current Opinion in Chemical Biology, (2009), 13(3): 245-255 or PCT/US2009/041570. In some embodiments an aptamer is used as an affinity reagent. The terms "affinity reagent" and "binding agent" are used interchangeably herein.

In some embodiments, a non-affinity based method is used to assess the level of HSF1 polypeptide or HSF1 activation. For example, mass spectrometry could be used to detect HSF1 or to specifically detect phosphorylated HSF1.

In some embodiments, an antibody (or other affinity reagent) or procedure for use to detect HSF1 (or HSF1 phosphorylated on serine 326) can be validated, if desired, by showing that the classification obtained using the antibody or procedure correlate with a phenotypic characteristic of interest such as presence or absence of CIS, cancer prognosis, or treatment outcome, in an appropriate set of samples. For example, as described in the Examples, a commercially available monoclonal antibody preparation RT-629-PABX (Thermo Scientific) comprising a combination of rat monoclonal antibodies ("antibody cocktail") was validated for use in IHC for detection of HSF1 and classification of samples and subjects into different categories correlated with presence or absence of CIS, cancer prognosis, or treatment outcome. Other exemplary antibodies of use for detecting or isolating HSF1 are disclosed in the Examples. In some embodiments, an antibody or antibody preparation or a protocol or procedure for performing IHC may be validated for use in an inventive method by establishing that its use provides similar results to those obtained using RT-629-PABX and the procedures described in the Examples on an appropriate set of test samples. For example, an antibody or antibody preparation or a procedure may be validated by establishing that its use results in the same classification (concordant classification) of at least 80%, 85%, 90%, 95% or more of samples in an appropriate set of test samples as is obtained using the antibody preparation of RT-629-PABX. A set of test samples may be selected to include, e.g., at least 10, 20, 30, or more samples in each category in a classification scheme (e.g., "positive" and "negative" categories; categories of "no", "low", or "high" expression, scores of 1, 2, 3; etc.). In some embodiments, a set of test samples comprises breast tissue samples, e.g., from the NHS. In some embodiments a set of samples is in the form of a tissue microarray. Once a particular antibody or procedure is validated, it can be used to validate additional antibodies or procedures. Likewise, a probe, primer, microarray, or other reagent(s) or procedure(s) to detect HSF1 RNA can be validated, if desired, by showing that the classification obtained using the reagent or procedure correlates with a phenotypic characteristic of interest such as presence or absence of CIS, cancer prognosis, or treatment outcome, in an appropriate set of samples.

It will be understood that suitable controls and normalization procedures can be used to accurately quantify HSF1 expression, where appropriate. For example, measured values can be normalized based on the expression of one or more RNAs or polypeptides whose expression is not correlated with a phenotypic characteristic of interest. In some embodiments, a measured value can be normalized to account for the fact that different samples may contain different proportions of a cell type of interest, e.g., cancer cells, versus non-cancer cells. For example, in some embodiments, the percentage of stromal cells, e.g., fibroblasts, may be assessed by measuring expression of a stromal cell-specific marker, and the overall results adjusted to accurately reflect HSF1 mRNA or polypeptide level specifically in the tumor cells. Similarly, appropriate controls and normalization procedures can be used to accurately quantify HSF1 activation, where appropriate. It would also be understood that if a sample such a tissue section contains distinguishable (e.g., based on standard histopathological criteria), areas of neoplastic and non-neoplastic tissue, such as at the margin of a tumor, the level of HSF1 expression or activation could be assessed specifically in the area of neoplastic tissue, e.g., for purposes of comparison with a control level, which may optionally be the level measured in the non-neoplastic tissue.

In certain embodiments of the invention the level of HSF1 mRNA or protein level is not measured or analyzed simply as a contributor to a cluster analysis, dendrogram, or heatmap based on gene expression profiling in which expression at least 20; 50; 100; 500; 1,000, or more genes is assessed. In certain embodiments of the invention, e.g., if HSF1 mRNA or protein level is measured as part of such a gene expression profile, the level of HSF1 mRNA or protein is used to classify samples or tumors (e.g., for diagnostic, prognostic or treatment-specific predictive purposes) in a manner that is distinct from the manner in which the expression of many or most other genes in the gene expression profile are used. For example, the level of HSF1 mRNA or polypeptide may be used independently of most or all of the other measured expression levels or may be weighted more strongly than many or most other mRNAs in analyzing or using the results.

In some embodiments, HSF1 mRNA or polypeptide level is used together with levels of a set of no more than 10 other mRNAs or proteins that are selected for their utility for classification for diagnostic, prognostic, or predictive purposes in one or more types of cancer, such as breast cancer. For example, in the case of breast cancer, HSF1 mRNA or polypeptide levels can be used together with a measurement of estrogen receptor (ER), progesterone receptor (PR), or human epidermal growth factor receptor 2 (HER2) mRNA or polypeptide levels. In some embodiments, measurement of ER, PR, HER2 mRNA and/or other mRNA is performed using ISH. In some embodiments, measurement of ER, PR, HER2 polypeptide and/or other polypeptides is performed using IHC. In some embodiments such testing is performed in accordance with recommendations of the American Society of Clinical Oncology/College of American Pathologists Guideline Recommendations for Immunohistochemical Testing of Estrogen and Progesterone Receptors in Breast Cancer or the American Society of Clinical Oncology/College of American Pathologists Guideline Recommendations for Human Epidermal Growth Factor Receptor 2 Testing in Breast Cancer. In some embodiments such testing is performed according to recommendations of a commercially available kit, e.g., a kit approved by a governmental regulatory agency (e.g., the U.S. Food and Drug Administration) for use in clinical diagnostic, prognostic, or predictive purposes.

In general, the level of HSF1 activation can be assessed using any of a variety of methods in various embodiments of the invention. In some embodiments, the level of HSF1 activation is determined by detecting HSF1 polypeptide in cell nuclei, wherein nuclear localization of HSF1 polypeptide is indicative of HSF1 activation. HSF1 localization can be assessed, for example, using IHC, flow cytometry, FACS, etc. Alternately, or additionally, cell nuclei could be isolated and HSF1 polypeptide detected by immunoblot. In some embodiments, HSF1 nuclear localization could be assessed by staining for HSF1 protein, counterstaining with a dye that binds to a nuclear component such as DNA, and assessing co-localization of HSF1 and such nuclear component. Cell imaging can be used in some embodiments. It will be understood that "detecting" as used herein, can encompass applying a suitable detection procedure and obtaining a negative result, i.e., detecting a lack of expression or activation.

In some embodiments, the level of HSF1 activation is determined by determining the level of HSF1 phosphorylation, wherein HSF1 phosphorylation is indicative of HSF1 activation. In some embodiments, phosphorylation of HSF1 on serine 326 is determined as an indicator of HSF1 activation. Phosphorylation of HSF1 on serine 326 can be assessed, for example, using antibodies that bind specifically to HSF1 phosphorylated on serine 326. In some embodiments, a ratio of phosphorylated HSF1 to unphosphorylated HSF1 (on serine 326) is used as an indicator of HSF1 activation, with a higher ratio indicating more activation. Measurement of other post-translational modifications indicative of HSF1 activation could be used in various embodiments.

In some embodiments, the level of HSF1 activation is determined by measuring a gene expression profile of one or more genes whose expression is regulated by HSF1, wherein increased expression of a gene that is positively regulated by HSF1 or decreased expression of a gene that is negatively regulated by HSF1 is indicative of HSF1 activation. In many embodiments, the HSF1-regulated gene is not an HSP (e.g., HSP90) or, if HSP expression is measured, at least one additional HSF1-regulated gene other than an HSP is also measured. In some embodiments a gene expression profile measures expression of at least 5 HSF1-regulated genes, e.g., between 5 and about 1,000 HSF1-regulated genes. Of course the gene expression profile may in some embodiments also measure expression of one or more genes that are not regulated by HSF1. In some embodiments measurement of expression of one or more genes that are not regulated by HSF1 is used as a control or for normalization purposes. In some embodiments measurement of expression of one or more genes that are not regulated by HSF1 may be disregarded. In some embodiments no more than 1%, 5%, 10%, 20%, 30%, 40%, or 50%, of measurements are of genes that are not regulated by HSF1. In some embodiments, determining whether HSF1 is activated comprises comparing a gene expression profile obtained from a sample of interest with gene expression profile(s) obtained from one or more samples in which HSF1 is activated or is not activated. If the gene expression profile obtained from the sample clusters with or resembles the gene expression profile obtained from sample(s) in which HSF1 is activated, the sample of interest can be classified as exhibiting HSF1 activation. On the other hand, if the gene expression profile obtained from the sample of interest clusters with or resembles the gene expression profile obtained from sample(s) in which HSF1 is not activated, the sample of interest can be classified as not exhibiting HSF1 activation. Methods for clustering samples are well known in the art or assigning a sample to one of multiple clusters are well known in the art and include, e.g., hierarchical clustering, k-means clustering, and variants of these approaches.

In some embodiments, the level of HSF1 activation is determined by measuring binding of HSF1 to the promoter of one or more HSF1-regulated genes, wherein binding of HSF1 to the promoter of an HSF1-regulated gene is indicative of HSF1 activation. In some embodiments, an HSF1-regulated gene is a gene whose expression level (e.g., as assessed based on mRNA or protein levels) is increased or decreased by at least a factor of 1.2 as a result of HSF1 activation. In some embodiments, an HSF1-regulated gene is among the 1,000 genes in the human genome whose expression is most strongly affected (increased or inhibited) by HSF1. In some embodiments, an HSF1-regulated gene is among the 1,000 genes in the human genome whose promoter is most strongly bound by HSF1 under conditions in which HSF1 is activated. Methods for measuring binding of a protein (e.g., HSF1) to DNA (e.g., genomic DNA) include, e.g., chromatin immunoprecipitation using an antibody to the protein followed by microarray hybridization to identify bound sequences, commonly referred to as ChIP-on-chip (see, e.g., U.S. Pat. Nos. 6,410,243; 7,470,507; 7,575,869); ChIP-Sequencing, which uses chromatin immunoprecipitation followed by high throughput sequencing to identify the bound DNA; and DamID (DNA adenine methyltransferase identification; see, e.g., Vogel M J, et al (2007). "Detection of in vivo protein-DNA interactions using DamID in mammalian cells", Nat Protoc 2 (6): 1467-78).

In some embodiments, an assay to detect HSF1 expression or activation makes use of fluorescence resonance energy transfer (FRET).

In some embodiments, the level of an HSF1 gene product or the level of HSF1 activation is determined to be "increased" or "not increased" by comparison with a suitable control level or reference level. The terms "reference level" and "control level" may be used interchangeably herein. A suitable control level can be a level that represents a normal level of HSF1 gene product or HSF1 activation, e.g., a level of HSF1 gene product or HSF1 activation existing in cells or tissue in a non-diseased condition and in the substantial absence of stresses that activate the heat shock response. Thus any method that includes a step of (a) assessing (determining) the level of HSF1 gene expression or the level of HSF1 activation in a sample can comprise a step of (b) comparing the level of HSF1 gene expression or HSF1 activation with a control level of HSF1 gene expression or HSF1 activation, wherein if the level determined in (a) is greater than the control level, then the level determined in (a) is considered to be "increased" (or, if the level determined in (a) is not greater than the control level, then the level determined in (a) is considered to be "not increased". For example, if a tumor has an increased level of HSF1 expression or HSF1 activation as compared to a control level, the tumor is classified as having a high risk of poor outcome, while if the tumor does not have a significantly increased level of HSF1 relative to a control level, the tumor is classified as having a low risk of poor outcome. A control level may be determined in a variety of ways. In some embodiments a control level is an absolute level. In some embodiments a control level is a relative level, such as the percentage of tumor cells exhibiting nuclear HSF1 staining or the percentage of tumor cells or tumor cell nuclei exhibiting intense staining for HSF1. A comparison can be performed in various ways. For example, in some embodiments one or more samples are obtained from a tumor, and one or more samples are obtained from nearby normal (non-tumor) tissue composed of similar cell types from the same patient. The relative level of HSF1 gene product or HSF1 activation in the tumor sample(s) versus the non-tumor sample(s) is determined. In some embodiments, if the relative level (ratio) of HSF1 gene product in the tumor samples versus the non-tumor sample(s) is greater than a predetermined value (indicating that cells of the tumor have increased HSF1), the tumor is classified as high risk. In some embodiments the predetermined value is, e.g., at least 1.5, 2, 2.5, 3, 5, 10, 20, or more. In some embodiments the predetermined value is between about 1.5 and about 10. A control level can be a historical measurement. For example, the data provided herein provide examples of levels of HSF1 expression and HSF1 activation in normal breast, cervix, colon, lung, pancreas, prostate, and meningeal tissue and tissue from breast, cervix, colon, lung, pancreas, prostate, and meningeal tumors, thereby providing examples of suitable control levels. It will be understood that in at least some embodiments a value may be semi-quantitative, qualitative or approximate. For example, visual inspection (e.g., using light microscopy) of a stained IHC sample can provide an assessment of the level of HSF1 expression or HSF1 activation without necessarily counting cells or nuclei or precisely quantifying the intensity of staining.

Various risk categories may be defined. For example, tumors may be classified as at low, intermediate, or high risk of poor outcome. A variety of statistical methods may be used to correlate the risk of poor outcome with the relative or absolute level of HSF1 expression or HSF1 activation.

For purposes of description herein it is assumed that the control or reference level represents normal levels of HSF1 expression or HSF1 activation present in non-cancer cells and tissues. However, it will be understood that a level of HSF1 expression or HSF1 activation characteristic of cancer (e.g., breast cancer) could be used as a reference or control level. In that case, the presence of HSF1 expression or HSF1 activation at a level comparable to, e.g., approximately the same, as or greater than the control level would be indicative of the presence of cancer, poor cancer prognosis, aggressive cancer phenotype, or to identify a subject who is a suitable candidate for treatment with a proteostasis modulator, while a decreased level of HSF1 expression or HSF1 activation as compared with the control level would be predictive of good cancer prognosis, less aggressive cancer phenotype or to identify a subject who may not be a suitable candidate for treatment with a proteostasis modulator, etc.

Methods have generally been stated herein mainly in terms of conclusions or predictions that can be made if increased HSF1 expression or increased HSF1 activation is present. Methods could equally well have been stated in terms of conclusions or predictions that can be made if increased HSF1 expression or increased HSF1 activation is not present. For example, if HSF1 expression is absent in a sample being assessed for the presence or absence of cancer, the sample would not be classified as cancer based on HSF1 expression. If HSF1 expression or HSF activation is absent or low in a sample from an invasive tumor, the tumor would be classified as having a good prognosis. If HSF1 expression or HSF activation is absent or low in a sample from an invasive tumor, the subject may not benefit from treatment with a proteostasis modulator.

Any of the methods of the invention may, in certain embodiments, comprise assigning a score to a sample (or to a tumor from which a sample was obtained) based on the level of HSF1 expression or HSF1 activation measured in the sample, e.g., based on the level of an HSF1 gene product or the level of HSF1 activation or a combination thereof.

In some embodiments a score is assigned based on assessing both HSF1 polypeptide level and HSF1 activation level. For example, a score can be assigned based on the number (e.g., percentage) of nuclei that are positive for HSF1 and the intensity of the staining in the positive nuclei. For example, a first score (e.g., between 0 and 5) can be assigned based on the percentage positive nuclei, and a second score (e.g., between 0 and 5) assigned based on staining intensity in the nuclei. In some embodiments, the two scores are added to obtain a composite score (e.g., ranging between 0 and 10). In some embodiments the two scores are multiplied to obtain a composite score (e.g., ranging between 0 and 25). The range can be divided into multiple (e.g., 2 to 5) smaller ranges, e.g., 0-9, 10-18, 19-25, and samples or tumors are assigned an overall HSF1 expression/activation score based on which subrange the composite score falls into. For example, 0-9 is low, 10-18 is intermediate, and 19-25 is high in some embodiments. A higher score indicates, for example, increased aggressiveness, increased likelihood of poor outcome, poor prognosis. Thus in some aspects, the invention provides a method of assigning a score to a sample comprising cells, the method comprising steps of: (a) assigning a first score to the sample based on the number or percentage of cell nuclei that are positive for HSF1 protein; (b) assigning a second score to the sample based on the level of HSF1 protein in cell nuclei; and (c) obtaining a composite score by combining the scores obtained in step (a) and step (b). In some embodiments, combining the scores comprises adding the scores. In some embodiments combining the scores comprises multiplying the scores. In some embodiments the method further comprises assigning the sample to an HSF1 expression/activation category based on the composite score. It will be understood that if the sample is a tissue sample that comprises areas of neoplastic tissue and areas of non-neoplastic tissue (e.g., as identified using standard histopathological criteria), the score(s) can be assigned based on assessing neoplastic tissue. The non-neoplastic tissue may be used as a control.

In some embodiments, a score is assigned using a scale of 0 to X, where 0 indicates that the sample is "negative" for HSF1 (e.g., no detectable HSF1 polypeptide in cell nuclei), and X is a number that represents strong (high intensity) staining in the majority of cell nuclei. X can be, e.g., 2, 3, 4, or 5 in various embodiments. In some embodiments, a score is assigned using a scale of 0, 1, or 2, where 0 indicates that the sample is negative for HSF1 (no detectable HSF1 polypeptide in cell nuclei), 1 is low level nuclear staining and 2 is strong (high intensity) staining in the majority of cell nuclei. A higher score indicates a less favorable prognosis than a lower score, e.g., more likely occurrence of metastasis, shorter disease free survival, lower likelihood of 5 year survival, lower likelihood of 10 year survival, or shorter average survival. A score can be obtained by evaluating one field or multiple fields in a cell or tissue sample. Multiple samples from a tumor may be evaluated in some embodiments. It will be understood that "no detectable HSF1" could mean that the level detected, if any, is not noticeably or not significantly different to background levels. It will be appreciated that a score can be represented using numbers or using any suitable set of symbols or words instead of, or in combination with numbers. For example, scores can be represented as 0, 1, 2; negative, positive; negative, low, high; −, +, ++, +++; 1+, 2+, 3+, etc.

In some embodiments, at least 20, 50, 100, 200, 300, 400, 500, 1000 cells, or more (e.g., tumor cells) are assessed to evaluate HSF1 expression or HSF activation in a sample or tumor, e.g., to assign a score to a sample or tumor. In some embodiments, samples or tumors that do not exhibit HSF1 polypeptide in nuclei, e.g., as assessed using IHC, may be considered negative for HSF1.

The number of categories in a useful scoring or classification system can be at least 2, e.g., between 2 and 10, although the number of categories may be greater than 10 in some embodiments. The scoring or classification system often is effective to divide a population of tumors or subjects into groups that differ in terms of an outcome such as local progression, local recurrence, discovery or progression of regional or distant metastasis, death from any cause, or death directly attributable to cancer. An outcome may be assessed over a given time period, e.g., 2 years, 5 years, 10 years, 15 years, or 20 years from a relevant date. The relevant date may be, e.g., the date of diagnosis or approximate date of diagnosis (e.g., within about 1 month of diagnosis) or a date after diagnosis, e.g., a date of initiating treatment. Methods and criteria for evaluating progression, response to treatment, existence of metastases, and other outcomes are known in the art and may include objective measurements (e.g., anatomical tumor burden) and criteria, clinical evaluation of symptoms), or combinations thereof. For example, 1, 2, or 3-dimensional imaging (e.g., using X-ray, CT scan, or MRI scan, etc.) and/or functional imaging (e.g., PET scan) may be used to detect or assess lesions (local or metastatic), e.g., to measure anatomical tumor burden, detect new lesions, etc. In some embodiments, a difference between groups is statistically significant as determined using an appropriate statistical test or analysis method, which can be selected by one of ordinary skill in the art. In many embodiments, a difference between groups would be considered clinically meaningful or clinically significant by one of ordinary skill in the art.

Kits and Systems

In some aspects, the invention provides kits comprising reagents suitable for performing an assay to assess HSF1 expression or HSF1 activation, e.g., for use in a method of the invention. Such kits may contain, e.g., (i) a probe or primer (optionally labeled and/or attached to a support) for detecting, reverse transcribing, and/or amplifying an HSF1 RNA, (e.g., HSF1 mRNA); (ii) a probe or primer for detecting, reverse transcribing, and/or amplifying an RNA (e.g., mRNA) transcribed from an HSF1-regulated gene; (iii) an antibody that binds to an HSF1 polypeptide (e.g., for use in IHC); (iv) one or more control reagents; (v) a detection reagent such as a detectably labeled secondary antibody or a substrate; (vi) one or more control or reference samples that can be used for comparison purposes or to verify that a procedure for detecting HSF1 expression or activation is performed appropriately or is giving accurate results. A control reagent can be used for negative or positive control purposes. A control reagent may be, for example, a probe or primer that does not detect or amplify HSF1 mRNA or an antibody that does not detect HSF1 polypeptide or a purified HSF1 polypeptide or portion thereof (e.g., an HSF1 peptide). A probe, primer, antibody, or other reagent may be attached to a support, e.g., a bead, slide, chip, etc.

Individual kit components may be packaged in separate containers (e.g., tubes, bottles, etc.) The individual component containers may be packaged together in a larger container such as a box for commercial supply. Optionally the kit comprises written material, e.g., instructions, e.g., in a paper or electronic format (e.g., on a computer-readable medium). Instructions may comprise directions for performing the assay and/or for interpreting results, e.g., in regard to tumor classification, diagnosis, prognosis, or treatment-specific prediction. Such material could be provided online.

In some embodiments, the invention provides a system which is adapted or programmed to assess HSF1 expression or HSF1 activation, e.g., for use in a method of the invention. In some embodiments the system may include one or more instruments (e.g., a PCR machine), an automated cell or tissue staining apparatus, an imaging device (i.e., a device that produces an image), and/or one or more computer processors. The system may be programmed with parameters that have been selected or optimized for detection and/or quantification of an HSF1 gene product, e.g., in tumor samples. The system may be adapted to perform the assay on multiple samples in parallel and/or may have appropriate software to analyze samples (e.g., using computer-based image analysis software) and/or provide an interpretation of the result. The system can comprise appropriate input and output devices, e.g., a keyboard, display, etc.

In some embodiments, an assay is performed at one or more central testing facilities, which may be specially qualified or accredited (e.g., by a national or international organization which, in some embodiments, is a government agency or organization or a medical or laboratory professional organization) to perform the assay and, optionally, provide a result. A sample can be sent to the laboratory, and a result of the assay, optionally together with an interpretation, is provided to a requesting individual or entity. In some embodiments, determining the level of HSF1 expression or the level of HSF1 activation in a sample obtained from the tumor comprises providing a tumor sample to a testing facility. In some aspects, the invention provides a method comprising: providing to a testing facility (a) a sample obtained from a subject; and (b) instructions to perform an assay to assess the level of HSF1 expression or HSF1 activation (and, optionally, instructions to perform one or more additional assays, e.g., one or more additional assays described herein). In some embodiments a method comprises entering an order for an assay of HSF1 expression or HSF1 activation into an electronic ordering system, e.g., of a health care facility. In some aspects, the invention provides a method comprising: (a) providing to a testing facility a sample obtained from a subject; and (b) receiving results of an assay of HSF1 expression or HSF1 activation. In some aspects, the invention further provides a method comprising providing, e.g., electronically, a result of such an assay, to a requestor. In some embodiments a result is provided at least in part by entering the result into a computer, e.g., into a database, electronic medical record, laboratory information system (sometimes termed laboratory information management system), etc., wherein it may be accessed by or under direction of a requestor. In some embodiments a result may be provided via phone, voicemail, fax, text message, or email. In some embodiments a result is provided at least in part over a network, e.g., the Internet. In some aspects, the invention further provides a method comprising receiving, e.g., electronically, a sample and a request for an assay of HSF1 expression or HSF1 activation, performing such assay, and reporting the result of such assay to a requestor. A result can comprise one or more measurements, scores and/or a narrative description. In some embodiments, a result provided comprises a measurement, score, or image of the sample, with associated diagnostic, prognostic, or treatment-specific predictive information. In some embodiments, a result provided comprises a measurement, score, or image of the sample, without associated diagnostic, prognostic, or treatment-specific predictive information. The invention contemplates that an assay may be performed at a testing facility which is remote from the site where the sample is obtained from a subject (e.g., at least 1 kilometer away) although of course an assay may be performed at the site where the sample is obtained or any other site in various embodiments. It is contemplated that samples and/or results may be transmitted to one or more different entities, which may carry out one or more steps of an assay or a method of the invention or transmit or receive results thereof. All such activities are within the scope of various embodiments of the invention.

In some embodiments a method described herein is computer-assisted. "Computer-assisted" as used herein encompasses methods in which a computer is used to gather, process, manipulate, display, visualize, receive, transmit, store, or in any way handle or analyze information (e.g., data, results, images, etc.). A computer may be used, for example, in sample processing, automated sample staining, automated image analysis, sample tracking, transmitting a request for an assay, transmitting a result of an assay, storing a result, etc. A method may comprise causing the processor of a computer to execute instructions to gather, process, manipulate, display, receive, transmit, or store data or other information. The instructions may be embodied in a computer program product comprising a computer-readable medium. A computer-readable medium may be any tangible medium (e.g., a non-transitory storage medium) having computer usable program instructions embodied in the medium. Any combination of one or more computer usable or computer readable medium(s) may be utilized in various embodiments. A computer-usable or computer-readable medium may be or may be part of, for example but not limited to, an electronic, magnetic, optical, electromagnetic, infrared, or semiconductor system, apparatus, or device. Examples of a computer-readable medium include, e.g., a hard disk, a random access memory (RAM), a read-only memory (ROM), an erasable programmable read-only memory (e.g., EPROM or Flash memory), a portable compact disc read-only memory (CDROM), a floppy disk, an optical storage device, or a magnetic storage device. In some embodiments a method comprises transmitting or receiving data or other information over a communication network. Data or information may be generated at or stored on a first computer-readable medium at a first location, transmitted over the communication network, and received at a second location, where it may be stored on a second computer-readable medium. A communication network may, for example, comprise one or more intranets or the Internet. In some embodiments results of an assay are stored in a database, which may be stored on a computer-readable medium. In some embodiments result(s) are stored in association with a sample identifier. In some embodiments result(s) are stored in association with a subject identifier. In some embodiments results of an assay are stored in a subject's electronic health record. Additional information regarding a tumor may be stored as well. Such information may comprise, for example, an assessment of tumor grade, tumor stage, tumor type (e.g., cell type or tissue of origin) and/or results of assessing expression of one or more genes of interest. In some embodiments a result is provided in a report.

EXEMPLIFICATION

Materials and Methods Used in Examples 1-8

Study Design and Population

The Nurses' Health Study (NHS) is a prospective cohort study initiated in 1976 (40, 41). 121,700 female US-registered nurses between the ages of 30-55 completed a questionnaire on factors relevant to women's health with follow-up biennial questionnaires used to update exposure information and ascertain non-fatal incident diseases (40). The follow-up rate was greater than 90% through 1996. Participants who developed breast cancer were identified through the biennial questionnaires and permission was obtained for a review of the medical record. The diagnosis of cancer was confirmed by chart review in 99% participants who self-reported the development of breast cancer. Tumor size, existence of metastatic disease, histologic subtype and invasive or in situ status were recorded from the medical record. This information was used to assign a clinical stage to the patients using the parameters listed in the legend of Table 1. In cases of deceased participants, death certificates and medical records were obtained to ascertain information relevant to the study. Use of this information and associated pathology materials for the study reported here was approved by the Human Subjects Committee at Brigham and Women's Hospital in Boston, Mass.

Tissue Microarray Construction

The NHS breast cancer tissue block collection and tissue microarray (TMA) assembly have been described previously (40, 41). Formalin fixed paraffin-embedded tissue blocks were collected from breast cancers that developed within a follow-up period of 20 years spanning 1976 to 1996. Samples were successfully obtained from 3,752 of the 5,620 participants that were eligible for block collection. The diagnosis, tumor type, and histologic grade were confirmed by review of Hematoxylin and eosin (H&E) stained sections. A total of 23 TMA blocks were constructed at the Dana Farber/Harvard Cancer Center Tissue Microarray Core Facility in Boston from 3,093 primary tumors and lymph nodes with metastatic disease derived from 2,897 study participants. For this study, tissue was available from 21TMAs including samples from 2656 individuals.

Paraffin blocks were also obtained from the archives of Brigham and Women's Hospital (BWH) in accordance with the regulations for excess tissue use stipulated by the BWH institutional review board. Twenty-four blocks from individual patients were used to construct an additional tissue microarray from normal breast tissue derived from breast reduction mammoplasty procedures. Normal breast epithelial lobules were identified on H&E stained sections and three 0.6 mm cores were taken and transferred into a recipient paraffin block at the Dana Farber/Harvard Cancer Center Tissue Microarray Core Facility. Epithelium from 16 lobules could be identified in the sections used for this study. Additional whole tissue sections were made from paraffin blocks of invasive ductal carcinoma or ductal carcinoma in situ, invasive ductal carcinoma, and matched normal breast controls from the invasive carcinoma cases.

Lung, colon, and prostate tissue studied was also formalin-fixed paraffin-embedded human biopsy material. Tissue microarrays were purchased from Pantomics (Richmond, Calif.) for carcinoma of the breast (BRC1501, BRC1502), cervix (CXC1501), colon (COC1503), lung (LUC1501), pancreas (PAC481) and prostate (PRC1961). Whole sections of 40 meningioma specimens were retrieved from the archives of BWH. Normal tissue cores on the TMAs and adjacent normal tissues in the whole sections were used to evaluate expression of HSF1 in non-neoplastic tissues.

Immunohistochemistry of Tissues

Paraffin sections of human and mouse tissues and tissue microarrays were stained with a rat monoclonal antibody cocktail to HSF1 (Thermo Scientific RT-629-PABX). According to the manufacturer's data sheet, this antibody preparation contains a combination of monoclonal antibodies obtained from hybridoma clones 4B4, 10H4, and 10H8, generated using recombinant mouse HSF1 protein (amino acids 1-503) as an immunogen, and reported to recognize an epitope within amino acids 288-439. Deparaffinized sections were blocked with 3% H2O2, antigen retrieval was performed using a pressure cooker with Dako citrate buffer (pH 6.0) at 120° C. +/−2° C., 15 +/−5 PSI, slides were blocked with 3% normal rabbit serum and primary HSF1 antibody (1:2000) was incubated at room temperature for 40 minutes. Application of the primary antibodies was followed by 30 minute incubation with Dako Labeled Polymer-HRP anti-rat IgG as a secondary antibody, and visualized with 3,3'-diaminobenzidine (DAB) as a chromogen (Dako Envision+ System). Mayer-hematoxylin was used for counterstaining.

Immunostained sections were reviewed by light microscopy and scored visually with a value assigned to each individual core. Scoring was based on a semi-quantitative review of staining intensity with 0 indicating no nuclear staining, 1 indicating low level nuclear staining and 2 indicating strong nuclear staining for HSF1. The immunostained sections were evaluated independently by two pathologists (SS and TAI) who were blinded to the survival outcomes of the participants and scores given by the other pathologist. Scoring averages were determined per case from values assigned to all evaluable cores from the two independent readings. If diagnostic tissue was absent or if the staining was uninterpretable for all three cores, the case status was recorded as missing. The kappa value was used to measure inter-observer variability among the two pathologist reviews. The kappa statistic was 0.92 for the scoring of HSF1-positive versus negative tumors and 0.84 for the scoring of HSF1-negative, HSF1-low, versus HSF1-high tumors. Cases with no detectable HSF1 or only cytoplasmic immunoreactivity are referred to as HSF1-negative tumors and cases with low or high nuclear HSF1 are referred to as HSF1-positive tumors unless indicated otherwise. The ER, PR and HER2 status of each case was determined as previously described (42). HSF1 wild-type and null mice as a source of tissue for immunostaining controls were a kind gift from Ivor Benjamin (3).

Figure 5A:
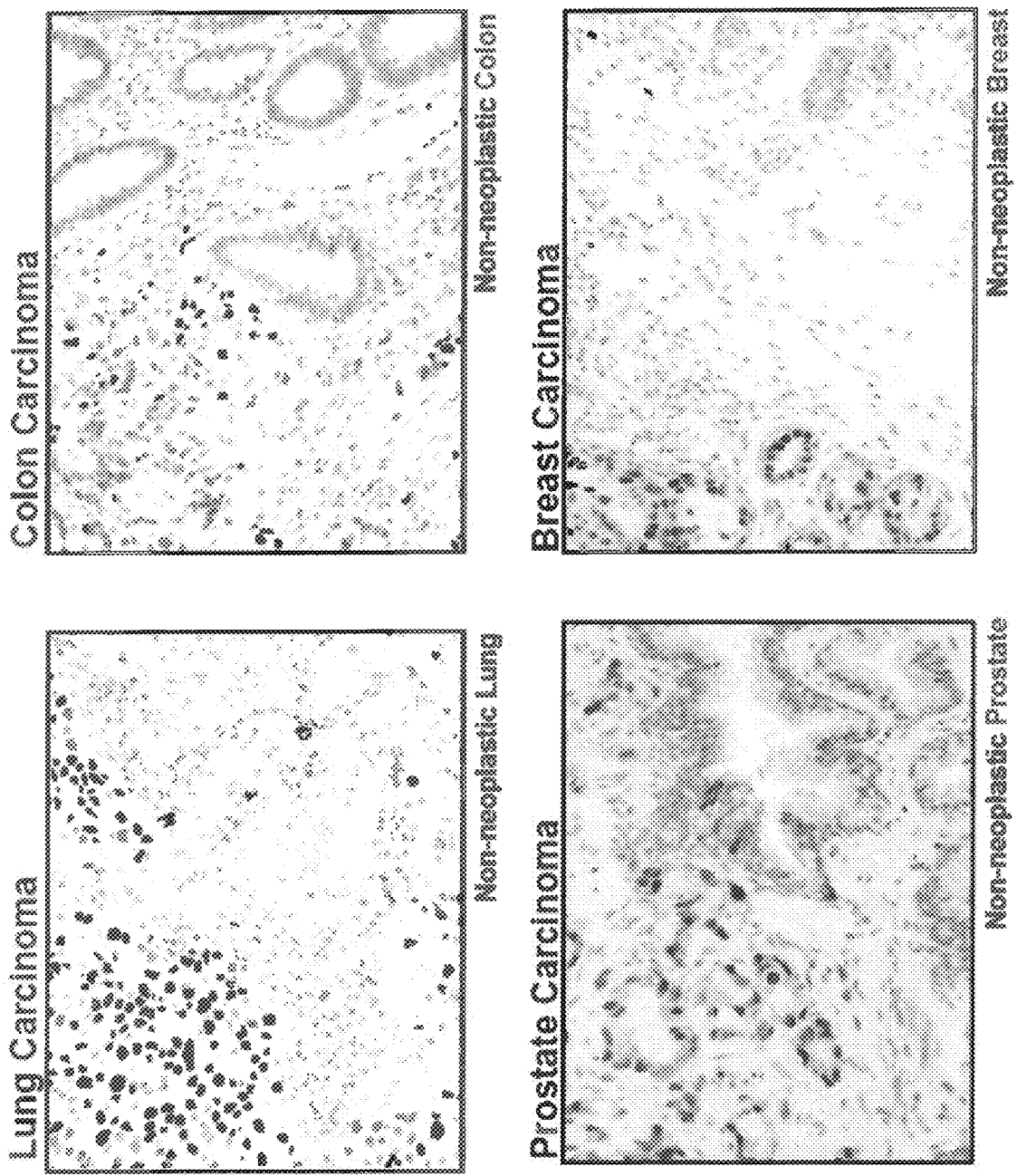
FIG. 5. HSF1 is activated in multiple human tumor types. (A). Immunoperoxidase staining (brown) with an anti-HSF1 antibody of formalin-fixed paraffin-embedded human biopsy material of the indicated tissue types (lung, colon, prostate, breast) showing areas of neoplastic (cancerous) and non-neoplastic (noncancerous) tissue as indicated. (B) Representative images of HSF1 IHC showing high level nuclear staining in a panel of invasive human tumors including carcinomas of the cervix, colon, lung, pancreas, and prostate and in a mesenchymal tumor, meningioma; T, Tumor; N, Normal adjacent tissue. A quantitative summary of all HSF1 IHC results categorized by tissue type from an analysis of TMAs or whole tissue sections is presented in the bar graph (right).
Figure 5B:
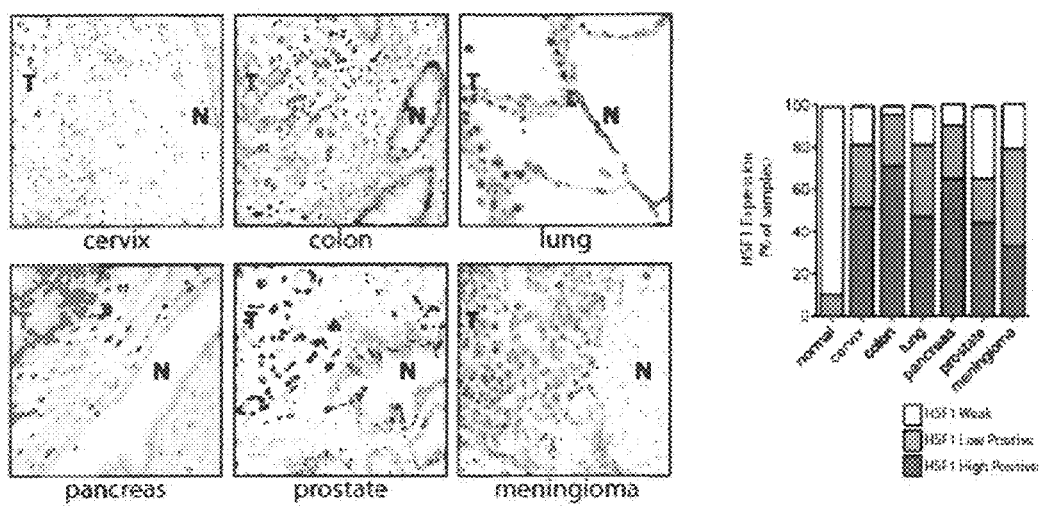

In the analysis depicted in FIGS. 4C and 4D and 5B (see last paragraph of Example 1) and described in Example 6, scoring was performed as follows: Scoring was based on a 0 to 5 scale for percent of cells that exhibited staining (0 being no staining, 1 being <20% of cells staining, 2 being 20%-40% of cells staining, 3 being 40%-60% of cells staining, 4 being 60%-80% of cells staining, 5 being 80%-100% of cells staining) and a 0 to 5 score for intensity. The percent score and intensity score were then multiplied to get a total score between 0 and 25, thus the overall score ranged from 0-25. Tumors with a score greater than 18 were assigned to the HSF1 high positive group; tumors with a score between 10 and 18 (inclusive) were assigned to the HSF1 low positive group; tumors with a score below 10 were assigned to the HSF1 weak group.

In the analysis described in Example 8 and depicted in FIG. 9, scoring was based on a 0 to 5 scale for percent of cells that exhibited staining (0 being no staining, 1 being <20% of cells staining, 2 being 20%-40% of cells staining, 3 being 40%-60% of cells staining, 4 being 60%-80% of cells staining, 5 being 80%-100% of cells staining) and a 0 to 5 score for intensity. The percent score and intensity score were then multiplied to get a total score between 0 and 25, thus the overall score ranged from 0-25. Tumors with a score greater than or equal to 20 were assigned to the HSF1 high group; the HSF1 intermediate group had a score of 10-20; and the HSF1 low group had scores <10.

Immunoblotting

Tissue blot IMB-130a from Imgenex Corp (San Diego, Calif.) was blocked with 5% non-fat dry milk in 1X PBS (pH 7.4) and washed with 1X PBS (pH 7.4) containing 0.1% Tween 20. Primary antibodies were applied in 1X PBS (pH 7.4)+0.5% non-fat dry milk for 1 hour at room temperature. Peroxidase-conjugated secondary antibodies were applied at room temperature for 1 hour and the signal was visualized by incubation with a chemiluminescent substrate (Pico-West, Thermo-Fisher). Tissues lysates from HSF1 wild-type and null mice were made from freshly harvested organs that were immediately frozen in liquid nitrogen, and subsequently extracted in cold lysis buffer (100 mM NaCl, 30 mM Tris-HCl (pH 7.6), 1% NP-40, 1 mM EDTA, 1 mM sodium orthovanadate, 30 mM sodium fluoride, and a complete protease inhibitor cocktail tablet (Roche Diagnostics)). Protein concentrations were determined using a BCA reagent (Pierce Biochemical) and proteins were separated on NuPAGE® Novex gels and transferred to Immun-Blot® PVDF membrane (Bio-Rad).

Selection Criteria for Outcome Analysis

This study included women with either ductal carcinoma in situ or invasive breast carcinoma that were diagnosed between 1976, after the completion of the baseline initial questionnaire, and 1996. Inclusion in the study (n=2656) required that tissue from the primary breast lesion was available for TMA construction and that outcome data was also available. Kaplan-Meier analysis and multivariate analysis were performed with data from participants with invasive breast cancer at diagnosis. Participants were excluded from outcome analysis if they had in situ carcinoma only (n=408), stage 1V breast cancer at the time of diagnosis (n=50) or HSF1-status could not be evaluated due to missing cores (n=357). Hence, outcome analysis was performed on 1,841 women. Expression of HSF1 was also analyzed in 200 cases of ductal carcinoma in situ which were not included in outcome analysis.

Covariates Evaluated in the Analysis

The medical record and supplemental questionnaires were used to garner information on the breast tumor and treatments including year of diagnosis, stage, radiation, chemotherapy and hormonal treatments. Histological grade was determined by centralized pathology review as described previously (41). Covariates considered in the multivariate model were based on both statistical significance and clinical significance. They included age at diagnosis, date of diagnosis, estrogen receptor status, disease stage, tumor grade, radiation treatment, chemotherapy and hormonal treatment.

Statistical Analysis

HSF1-positive (including HSF1-high and HSF-low) and HSF1-negative tumors were compared according to tumor characteristics and treatment variables by the chi-square test or Wilcoxon rank sum test, as appropriate. The survival endpoint was death from breast cancer. Deaths from any other causes were censored. Therefore, all mention of survival and mortality refer only to breast cancer-specific survival and mortality. Survival curves were estimated by the Kaplan-Meier method and statistical significance was assessed with the log-rank test. Cox proportional hazards regression models were used to evaluate the relationship between HSF1 status and breast cancer-specific mortality after adjusting for covariates. All analyses of the NHS data were run with SAS version 9.1 statistical software. Survival of patients from Van de Vivjer et al. (17) was analyzed by Kaplan-Meier methods and statistical significance was assessed with the log-rank test using GraphPad Prism 5. All statistical tests were two-sided and a P value of <0.05 was considered statistically significant.

Example 1

Characterization of HSF1 Antibody and HSF1 Expression in Breast Cancer and Various Other Cancer Types To facilitate our studies of HSF1, we verified the specificity of a commercially-available HSF1 antibody cocktail on samples from HSF1 wild-type and null mice. A strong immunoreactive band of the expected size for HSF1 was present in wild-type lysates but was absent in lysates null for HSF1 (FIG. 1A). Strong nuclear staining was observed by immunohistochemistry (IHC) in wild-type mouse tissues but not in corresponding tissues from HSF1 null mice (FIG. 1B) validating this antibody cocktail for IHC applications.

We examined the expression of HSF1 in invasive carcinoma and matched normal adjacent breast tissue from seven patients by immunoblot (FIG. 1C). More HSF1 was present in the tumors than the matched controls in all cases. Interestingly, there was a strong HSF1 band in three of seven samples obtained from the tumors and moderate to weak bands in the remaining tumors. The variation observed in this pilot study indicated that human breast tumors express HSF1 at different amounts, and encouraged us to examine whether the amount of HSF1 protein expression correlates with prognosis.

Figure 2F:
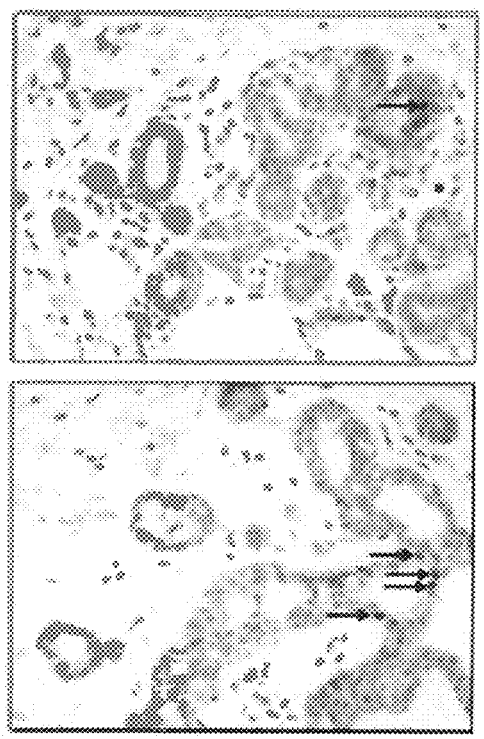
FIG. 2. HSF1 is increased and localized to the nucleus in invasive and in situ breast carcinoma. Photomicrographs of H&E sections and HSF1 immunohistochemistry of (A, B) invasive ductal carcinoma and (C, D) the pre-invasive lesion, ductal carcinoma in situ (DCIS). Non-neoplastic breast epithelium is indicated by the arrows and neoplastic cells are indicated by the arrowheads. (E) Representative photomicrographs of tumors from the NHS tissue microarrays that were stained by HSF1 immunohistochemistry and that were scored as having either no (−), low, or high nuclear HSF1 expression. This example with no nuclear HSF1 expression (−) demonstrates weak immunoreactivity in the cytoplasm. Scale bar, 20 μM. (F) HSF1 protein is expressed at low levels in occasional normal breast epithelial cells. HSF1 IHC was conducted with 1:500 dilution of the HSF1 antibodymixture (i.e., four times the increased antibody concentration than typically used in this study). Occasional cells in scattered normal breast lobules demonstrate nuclear HSF1 staining (arrows).

As a transcription factor HSF1 is active only in the nucleus. Hence, we examined the localization and expression levels of HSF1 in tumor cells versus normal cells by IHC in a small panel of breast carcinoma tissue sections. A striking difference between malignant cells and the adjacent normal breast epithelium was apparent (FIGS. 2A, 2B). While no nuclear HSF1 was detectable in nearly all cases in normal breast epithelium (n=16), there was nuclear staining in the majority of breast tumors. In samples of normal breast and in the tumors lacking nuclear HSF1, there was occasionally a weak cytoplasmic signal. The increase in HSF1 levels and its shift from the cytoplasm in normal cells into the nucleus in invasive tumors supported the premise that HSF1 is activated in the malignant state.

Figure 6:
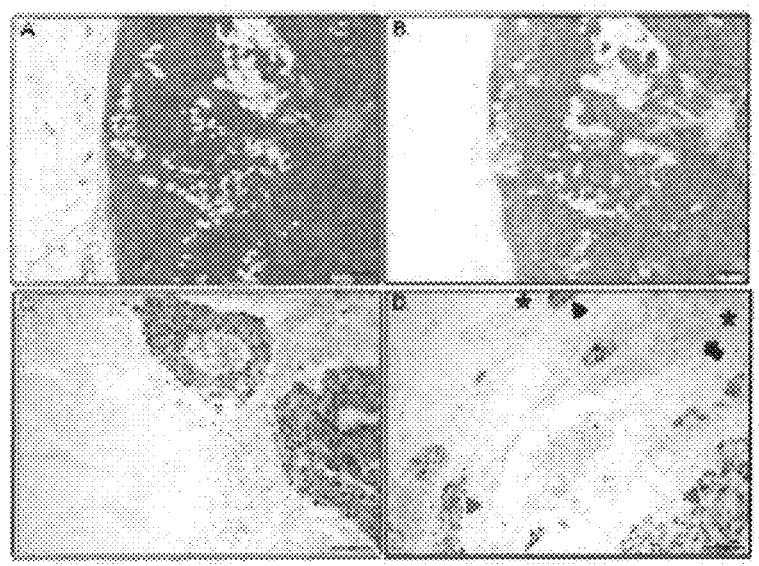
FIG. 6. HSF1 is uniformly expressed in invasive ductal carcinoma cells. (A) Low magnification H&E image of an invasive breast carcinoma. Scale bar, 150 μM. (B) HSF1 immunohistochemistry of the same area of the tumor demonstrates uniform HSF1 expression in invasive ductal carcinoma cells across the tumor cross section. There was no difference in intensity of staining at the center of the tumor versus the outer tumor/stroma interface. HSF1 immunohistochemistry demonstrating uniform HSF1 expression in invasive ductal carcinoma cells (C) embedded in a region of necrosis and (D) independent of adjacent inflammation or blood vessels. The black arrow indicates non-neoplastic breast epithelium. The black arrowhead indicates tumor cells adjacent to small blood vessels (asterisks). The two red arrowheads indicate tumor cells that are embedded in a region with desmoplasia and marked inflammation. These two photomicrographs are from neighboring regions of the same section of tumor. Scale bar, 100 μM.

In 20 HSF1-positive tumors, there was widespread uniform expression of HSF1 throughout the tumor cell nuclei. The uniform intensity of HSF1 expression is important to contrast with the variable patterns seen with most prognostic markers that are surveyed in human tumor sections with IHC. HSF1 staining was not stronger in tumor cells at the center of the tumor versus those at the stromal interface (FIG. 6A-B), or in regions of necrosis where macroenvironmental stress was likely to be severe (FIG. 6C). Staining intensity was also not dependent on the distance from stromal desmoplasia, inflammation or microvasculature (FIG. 6C-D). Without wishing to be bound by any theory, these observations suggest that increases in HSF1 in tumor cells are not principally due to external microenvironmental stress but more commonly result from internal, cell autonomous factors.

We also monitored HSF1 localization and levels of expression by immunohistochemistry (IHC) in a set of 301 clinical cases of invasive ductal carcinoma. The tumors were also characterized for expression of conventional breast cancer biomarkers, including estrogen receptor (ER), progesterone receptor (PR) and HER2. In total, 67 ER+ and/or PR+ tumors, 54 HER2+ tumors, and 180 triple negative (TN) tumors were evaluated along with 16 normal mammary tissue samples. In samples of normal breast tissue, HSF1 was rarely present in the nucleus (FIGS. 4A and 8). In stark contrast, HSF1 staining was dramatically elevated in many breast tumors and the signal was most often localized to the nucleus (FIGS. 4A, B and 8). Interestingly, higher levels of HSF1 staining were seen in HER2+ and TN tumors (FIG. 4C), which are breast cancer subtypes associated with more malignant behavior and worse outcome.

The findings in ten in situ carcinomas were similar to those in invasive cancer. In the majority of ductal carcinoma in situ (DCIS) cases, there was increased nuclear HSF1 compared to neighboring normal breast epithelium (FIG. 2C, 2D). The levels of HSF1 were also uniform in the DCIS cells (i.e., staining intensity was similar among the DCIS cells). These findings suggest that HSF1 expression is elevated during the in situ stage of malignant transformation and prior to invasion as well as subsequently.

We also examined HSF1 expression and localization in a range of other tumor types including lung, colon, and prostate adenocarcinomas using IHC. Increased HSF1 expression and increased nuclear HSF1 were seen in the neoplastic tissue in each of these tumor types (FIG. 5A). Elevated HSF1 expression and nuclear localization were also observed in cervical cancer and malignant peripheral nerve sheath tumors (data not shown).

We examined more than 300 formalin-fixed surgical specimens taken directly from patients. We included not only colon and lung cancer but also a wide variety of other tumor types. Normal cells adjacent to the tumor demonstrated low HSF1 levels and cytoplasmic localization of the protein. In contrast, high-level nuclear expression of HSF1 was common across every cancer type we examined, including carcinomas of the cervix, colon, lung, pancreas and prostate as well as mesenchymal tumors such as meningioma (FIG. 5B). In these tumors, expression was generally uniform across the sample, with nearly all tumor cells expressing similar levels of nuclear HSF1.

Example 2

Nuclear HSF1 is Highest in High-grade Breast Cancer and is Associated with Advanced Clinical Stage at Diagnosis We next performed an in-depth analysis of HSF1 protein expression in a large breast cancer cohort. 1,841 invasive breast cancer cases from the Nurses' Health Study (NHS) were evaluated for HSF1 localization and expression (FIG. 2E). 404 (21.9%) were negative for nuclear HSF1 and 1437 had detectable nuclear HSF1 (78.1%) with 882 (47.9%) demonstrating low and 555 (30.2%) high HSF1. Levels of HSF1 expression differed by histological-grade (P<0.0001). 40.5% of well-differentiated low-grade carcinomas were HSF1-negative and only 14.4% showed high nuclear HSF1 (Table 1). Conversely, in poorly-differentiated high-grade cancers, only 13.0% were HSF1-negative and 48.1% showed high HSF1 expression. Levels of HSF1 also differed by clinical parameters. Compared with HSF1-negative tumors, those with nuclear HSF1 expression were more likely to be diagnosed at a more advanced clinical stage (P<0.0001) (Table 1). Also, compared with HSF1-negative tumors, high-HSF1 tumors were more likely to be ER-negative (P<0.0001), HER2-positive (P=0.0003) and triple-negative (P=0.0084) supporting an association between HSF1 expression and a more malignant phenotype.

TABLE 1

Means and frequencies of participants' characteristics by HSF1-status (N = 1841), Nurses' Health Study (1976-1996).

| Characteristic | None | Low | High |
|---|---|---|---|
| N (%) | 404 (21.9) | 882 (47.9) | 555 (30.2) |
| Age at diagnosis, mean (N), yr | 57.8 (404) | 56.8 (882) | 57.6 (555) |
| Menopausal status at diagnosis, N* (%) | | | |
| Premenopausal | 74 (18.6) | 219 (25.3) | 109 (20.2) |
| Postmenopausal | 325 (81.5) | 648 (74.7) | 432 (79.9) |
| ER status, N* (%) | | | |
| Positive | 334 (82.7) | 702 (79.4) | 412 (71.2) |
| Negative | 70 (17.3) | 182 (20.6) | 167 (28.8) |
| HER2 status, N* (%) | | | |
| Positive | 23 (5.8) | 95 (10.7) | 81 (14.1) |
| Negative | 375 (94.2) | 794 (89.3) | 494 (85.9) |
| Triple-negative tumors, N* (%) | | | |
| Yes | 49 (12.2) | 122 (13.7) | 108 (18.7) |
| No | 353 (87.8) | 766 (86.3) | 471 (81.4) |

TABLE 1-continued

Means and frequencies of participants' characteristics by HSF1-status (N = 1841), Nurses' Health Study (1976-1996).

| Characteristic | None | Low | High |
|---|---|---|---|
| Nodal involvement, N (%) | | | |
| None | 290 (71.8) | 590 (66.9) | 324 (58.4) |
| 1-3 | 72 (17.8) | 166 (18.8) | 134 (24.1) |
| 4-9 | 26 (6.4) | 78 (8.8) | 55 (9.9) |
| ≥10 | 16 (4.0) | 48 (5.4) | 42 (7.6) |
| Tumor size (cm), N (%) | | | |
| ≤2 | 301 (74.5) | 589 (66.8) | 295 (53.2) |
| >2 | 103 (25.5) | 293 (33.2) | 260 (46.9) |
| Histological grade, N* (%) | | | |
| I (low) | 143 (35.8) | 159 (18.2) | 51 (9.3) |
| II (intermediate) | 199 (49.8) | 543 (62.1) | 284 (51.7) |
| III (high) | 58 (14.5) | 173 (19.8) | 214 (39.0) |
| Stage†, N (%) | | | |
| I | 239 (59.2) | 452 (51.3) | 217 (39.1) |
| II | 114 (28.2) | 283 (32.1) | 225 (40.5) |
| III | 51 (12.6) | 147 (16.7) | 113 (20.4) |
| Chemotherapy, N* (%) | | | |
| Yes | 101 (33.2) | 263 (41.9) | 217 (50.6) |
| No | 203 (66.8) | 365 (58.1) | 212 (49.4) |
| Hormone treatment, N* (%) | | | |
| Yes | 207 (68.8) | 415 (66.3) | 280 (66.0) |
| No | 94 (31.2) | 211 (33.7) | 144 (34.0) |
| Radiation treatment, N* (%) | | | |
| Yes | 136 (44.4) | 275 (43.7) | 185 (43.3) |
| No | 170 (55.6) | 354 (56.3) | 242 (56.7) |

*N doesn't add to total because of missing information.
†Stage I = tumor size <=2 cm and no nodal involvement;
II = tumor size <=2 cm & 1-3 nodes or 2-4 cm & 0-3 nodes or 4+ cm & 0 nodes;
III = tumor size <=2 cm & 4+ nodes or 2-4 cm & 4+ nodes or >4 cm & 1+ nodes.

Example 3

HSF1 Accumulates in the Nuclei of In Situ Carcinomas

Nuclear HSF1 was detected in 84.5% of the DCIS cases. The frequency and levels of HSF1 expression were similar between DCIS and invasive cancer, confirming our earlier observations on a smaller number of tumor sections. No statistically significant association was found between HSF1 expression and DCIS nuclear grade, however (Table 6). Our limited sample size of DCIS cases (n=200) may have limited the power to detect such an association. Nonetheless, these observations highlight that HSF1 is activated before malignant cells gain the ability to invade across the basement membrane.

TABLE 6

Frequency of HSF1 expression in DCIS according to tumor grade, Nurses' Health Study (1976 to 1996). Number of cases and (%). Chi-square analysis.

| HSF1 Expression | None | Low | High | P-value |
|---|---|---|---|---|
| DCIS | | | | 0.4907 |
| DCIS, low nuclear grade | 4 (22.2) | 11 (61.1) | 3 (16.7) | |
| DCIS, intermediate grade | 16 (16.8) | 54 (56.8) | 25 (26.3) | |
| DCIS, high nuclear grade | 11 (12.6) | 46 (52.9) | 30 (34.5) | |

Chi square analysis of HSF1-negative, HSF1-low and HSF1-high: P = 0.4907.

Example 4

HSF1 Expression is Associated with Reduced Survival in Breast Cancer

We next investigated the relationship between HSF1 expression and breast cancer survival. A total of 1841 women met inclusion criteria such as the absence of metastases at the time of diagnosis. Median follow-up time was 14.9 years. Kaplan-Meier curves show that women with HSF1-positive tumors had worse survival relative to women with HSF1-negative tumors (P<0.0001) (FIG. 3A). While a suggestive association was observed in the HER2-positive population (P=0.14) (FIG. 3B), no significant association was seen in triple-negative cases (P=0.63) (FIG. 3C). Because of the relatively small number of cases in the ER-negative groups, the study is likely underpowered to observe an effect in those populations. However, in women with ER-positive tumors, a strong association was observed between HSF1-positive tumors and worse outcome (P<0.0001) (FIG. 3D).

We also examined survival considering HSF1-status in three categories: HSF1-negative, HSF1-low and HSF1-high groups. Survival decreased as HSF1 levels increased from none to low and still further to high (P<0.0001) suggesting a dose-dependent association between HSF1 and survival outcomes (FIG. 3E). Dose-dependence was not seen for HER2-positive (P=0.22) and triple-negative populations (P=0.74) but was present in patients with ER-positive tumors (P<0.0001) (FIG. 3F).

Example 5

In Multivariate Models HSF1 is a Significant Independent Predictor of Worse Outcome To account for the effects of all variables considered on the relationship between HSF1 levels and survival, we assessed this relationship using several multivariate models. Across all cases, adjusting for age (model 1, Table 2), HSF1 positive tumors were associated with a 74% increase in breast cancer mortality (Table 2; Hazards Ratio (HR) 1.74, 95% Confidence Interval (CI), 1.35-2.25; P value<0.0001) relative to HSF1-negative tumors. After adjusting for age, ER-status, date of diagnosis, stage, grade, and treatment variables (radiotherapy, chemotherapy, endocrine therapy) (model 2, Table 2), HSF1 positive tumors were associated with a 50% increase in breast cancer mortality (Table 2; HR 1.50, 95% CI, 1.15-1.95; P value=0.0026). HSF1-low and HSF1-high tumors were associated with 45% (P=0.008) and 62% (P=0.001) increases in mortality, respectively (Table 3). Similar results were seen in the ER-positive population with HSF1-positive tumors associated with 86% increased mortality (Table 2; HR, 1.86; 95% CI, 1.34-2.59; P value=0.0002). Among the HSF1-positive tumors, HSF1-low and HSF1-high tumors were associated with 75% and 110% increases in mortality, respectively (Table 3).

74% (n=700) of the ER-positive patients received hormonal therapy. In this group, there was a significant association between HSF1-positive tumors and increased mortality (Table 2; HR, 2.20; 95% CI, 1.19-4.05; P value=0.0115). In women with ER-positive tumors who did not receive hormonal therapy (26%, n=247), the magnitude of the association was similar (Table 2; HR, 2.01; 95% CI, 0.69-5.88; P value=0.2002) but the study may have been underpowered to detect a significant association in this group. The data may suggest that HSF1 can contribute to tamoxifen resistance, an effect that may be evaluated further in follow-up studies prospectively in a uniformly-treated population.

HSF1 was also associated with worse clinical outcomes in patients with HER2-positive breast cancer. We observed that 88.4% of HER2-positive invasive tumors were HSF1-positive and 40.7% had high levels of HSF1, the greatest percentage of any molecular subtype. In Kaplan-Meier analysis, a suggestive association between HSF1-status and survival in patients with HER2-positive tumors was observed (FIG. 3B). In multivariate model 2, accounting for additional covariates, the strength of association increased and was statistically significant (Table 2; HR 2.87; 95% CI, 1.12-7.39; P value=0.0288). No association was observed between HSF1-status and survival among triple-negative patients (P=0.64) in multivariate models.

TABLE 2

Multivariate analysis of breast cancer-specific mortality by HSF1-status.

| Models | N Cases | Endpoints | Hazard Ratio (95% CI*) HSF1-negative | HSF1-positive |
|---|---|---|---|---|
| All cases: | | | | |
| Model[1] | 1841 | 463 | 1.00 | 1.74 (1.35-2.25) |
| Model[2] | 1841 | 463 | 1.00 | 1.50 (1.15-1.95) |
| ER-positive cases: | | | | |
| Model[1] | 1416 | 327 | 1.00 | 2.21 (1.60-3.06) |
| Model[3] | 1416 | 327 | 1.00 | 1.86 (1.34-2.59) |
| ER-negative cases: | | | | |
| Model[1] | 403 | 135 | 1.00 | 0.86 (0.56-1.32) |
| Model[3] | 403 | 135 | 1.00 | 0.88 (0.570-1.39) |
| HER2-positive cases: | | | | |
| Model[1] | 194 | 71 | 1.00 | 2.06 (0.83-5.12) |
| Model[2] | 194 | 71 | 1.00 | 2.87 (1.12-7.39) |
| HER2-negative cases: | | | | |
| Model[1] | 1621 | 386 | 1.00 | 1.61 (1.23-2.11) |
| Model[2] | 1621 | 386 | 1.00 | 1.37 (1.04-1.80) |
| Triple-negative cases: | | | | |
| Model[1] | 268 | 86 | 1.00 | 0.88 (0.52-1.50) |
| Model[3] | 268 | 86 | 1.00 | 0.88 (0.50-1.53) |
| ER-positive with hormone therapy cases: | | | | |
| Model[1] | 700 | 122 | 1.00 | 2.77 (1.52-5.02) |
| Model[4] | 700 | 122 | 1.00 | 2.20 (1.19-4.05) |
| ER-positive without hormone therapy cases: | | | | |
| Model[1] | 247 | 38 | 1.00 | 3.22 (1.14-9.10) |
| Model[4] | 247 | 38 | 1.00 | 2.01 (0.69-5.88) |

*CI denotes confidence interval.

Model[1]: Adjust for age at diagnosis (years).

Model[2]: Adjust for age at diagnosis (years), estrogen receptor status (positive, negative), date of diagnosis (months), disease stage (I, II, III), grade (I, II, III), radiation treatment (yes, no, missing), chemotherapy and hormonal treatment (no/no, yes/no, no/yes, yes/yes, missing).

Model[3]: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

Model[4]: Adjust for age at diagnosis (years), date of diagnosis (months), disease stage (I, II, III), grade (I, II, III), radiation treatment (yes, no, missing) and chemotherapy (yes, no, missing).

TABLE 3

Multivariate analysis of breast cancer-specific mortality by HSF1-status.

| Models | N Cases | Endpoints | Hazard Ratio (95% CI) None | Low | High |
|---|---|---|---|---|---|
| All cases: | | | | | |
| Model[1] | 1841 | 463 | 1.00 | 1.61 (1.23-2.11) | 1.97 (1.49-2.62) |
| Model[2] | 1841 | 463 | 1.00 | 1.45 (1.10-1.91) | 1.62 (1.21-2.17) |
| ER-positive cases: | | | | | |
| Model[1] | 1416 | 327 | 1.00 | 1.98 (1.41-2.78) | 2.66 (1.87-3.79) |
| Model[3] | 1416 | 327 | 1.00 | 1.75 (1.25-2.47) | 2.10 (1.45-3.03) |

*CI denotes confidence interval.
Model[1]: Adjust for age at diagnosis (years).
Model[2]: Adjust for age at diagnosis (years), estrogen receptor status (positive, negative), date of diagnosis (months), disease stage (I, II, III), grade (I, II, III), radiation treatment (yes, no, missing), chemotherapy and hormonal treatment (no/no, yes/no, no/yes, yes/yes, missing).
Model[3]: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

Example 6

HSF1 Activation is an Independent Prognostic Indicator of Poor Outcome in ER+/lymph Node Negative Breast Tumors We undertook an analysis of a subset of 947 women in the NHS cohort with ER+/lymph node negative tumors. This population is challenging to manage clinically since it is often unclear which small fraction of the population will experience a recurrence and could therefore benefit from early intervention and more aggressive treatment. Survival was examined by KM analysis considering HSF1-status in three categories: HSF1-negative, HSF1-low and HSF1-high groups. Survival decreased as HSF1 levels increased from none to low and further to high (P=0.0015) suggesting a dose-dependent association between HSF1 activation and survival (FIG. 4D). Multivariate analysis was performed to account for the effects of co-variates including age, date of diagnosis, stage, grade, and treatment variables (radiotherapy, chemotherapy, endocrine therapy). The association remained statistically significant, with the HSF1-positive (low+high cases) tumors associated with a 59% increase in mortality (Table 4), and with high-HSF1 tumors associated with a 98% increase in mortality (Table 5). This analysis demonstrates that even in one of the most challenging breast cancer populations from a prognostic standpoint, HSF1 activation is an independent prognostic indicator of poor outcome.

TABLE 4

Multivariate analysis of breast cancer-specific mortality by HSF1-status.

| Models | N Cases | Endpoints | Hazard Ratio (95% CI*) HSF1-negative | HSF1-positive |
|---|---|---|---|---|
| ER-positive, node negative cases: | | | | |
| Model[1] | 947 | 142 | 1.00 | 1.89 (1.20-2.98) |
| Model[2] | 947 | 142 | 1.00 | 1.59 (1.00-2.53) |

*CI denotes confidence interval.
Model[1]: Adjust for age at diagnosis (years).
Model[2]: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

TABLE 5

Multivariate analysis of breast cancer-specific mortality by HSF1-status.

| Models | N Cases | Endpoints | Hazard Ratio (95% CI) None | Low | High |
|---|---|---|---|---|---|
| ER-positive, node negative cases: | | | | | |
| Model[1] | 947 | 142 | 1.00 | 1.65 (1.02-2.66) | 2.41 (1.45-3.99) |
| Model[2] | 947 | 142 | 1.00 | 1.42 (0.88-2.31) | 1.98 (1.17-3.33) |

*CI denotes confidence interval.
Model[1]: Adjust for age at diagnosis (years).
Model[2]: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

Example 7

HSF1 mRNA Expression is Associated with Reduced Survival in Breast Cancer

Figure 7:
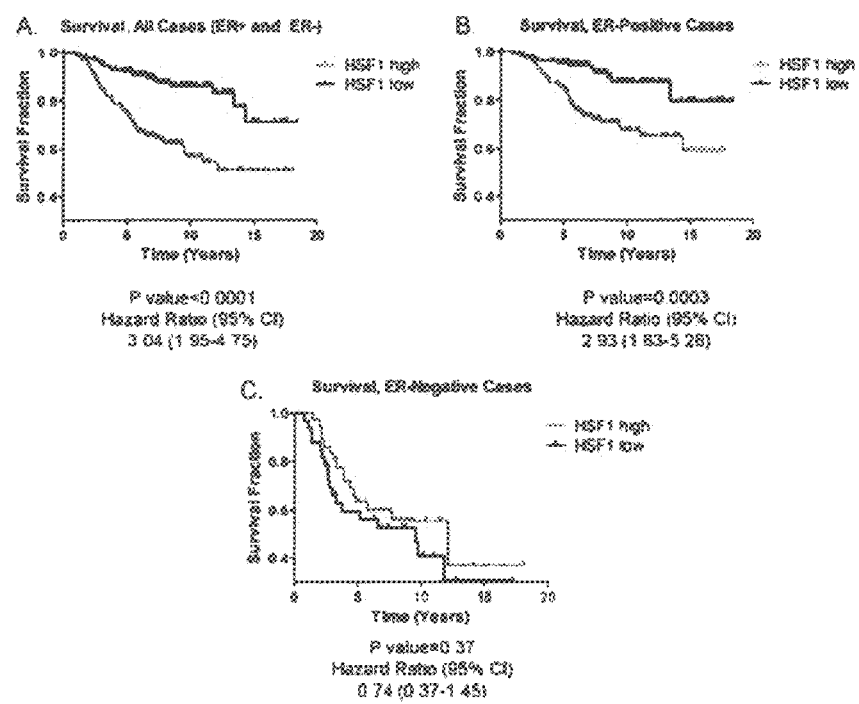
FIG. 7. HSF1 mRNA levels are associated with poor outcome in breast cancer. Kaplan-Meier analysis of all 295 individuals (A), only ER-positive (B) and only ER-negative patients (C) from Van de Vijver et al. (17). The highest 50% of cases expressing HSF1 constituted the HSF1-high group and the lowest 50% of cases constituted the HSF1-low group. Log-rank p values are shown.

We examined whether the associations between HSF1 protein level and outcome in breast cancer could also be detected using HSF1 mRNA levels. Since mRNA expression profiling data is not available from tumors in the NHS, we used data from the publicly available van de Vijver cohort (17) for this analysis. Consistent with our immunohistochemistry analysis in the NHS sample obtained from the tumors, HSF1 mRNA levels were higher in ER-negative than in ER-positive cancers (P<0.0001). We analyzed survival using two HSF1 categories: HSF1-high and HSF1-low. Kaplan-Meier curves show that women with HSF1-high tumors in the van de Vijver cohort had worse survival relative to women with HSF1-low tumors (FIG. 7A; HR 3.04; 95% CI, 1.95-4.75; P value<0.0001). The difference in survival between women with HSF1-high tumors and HSF1-low tumors was seen in the ER-positive (FIG. 7B; HR 2.93; 95% CI, 1.63-5.26; P value=0.0003) but not in the ER-negative population (FIG. 7C; HR 0.74, 95% CI, 0.37-1.45; P value=0.3736).

Example 8

HSF1 Expression is Associated with Reduced Survival in Lung Cancer

Figure 9A:
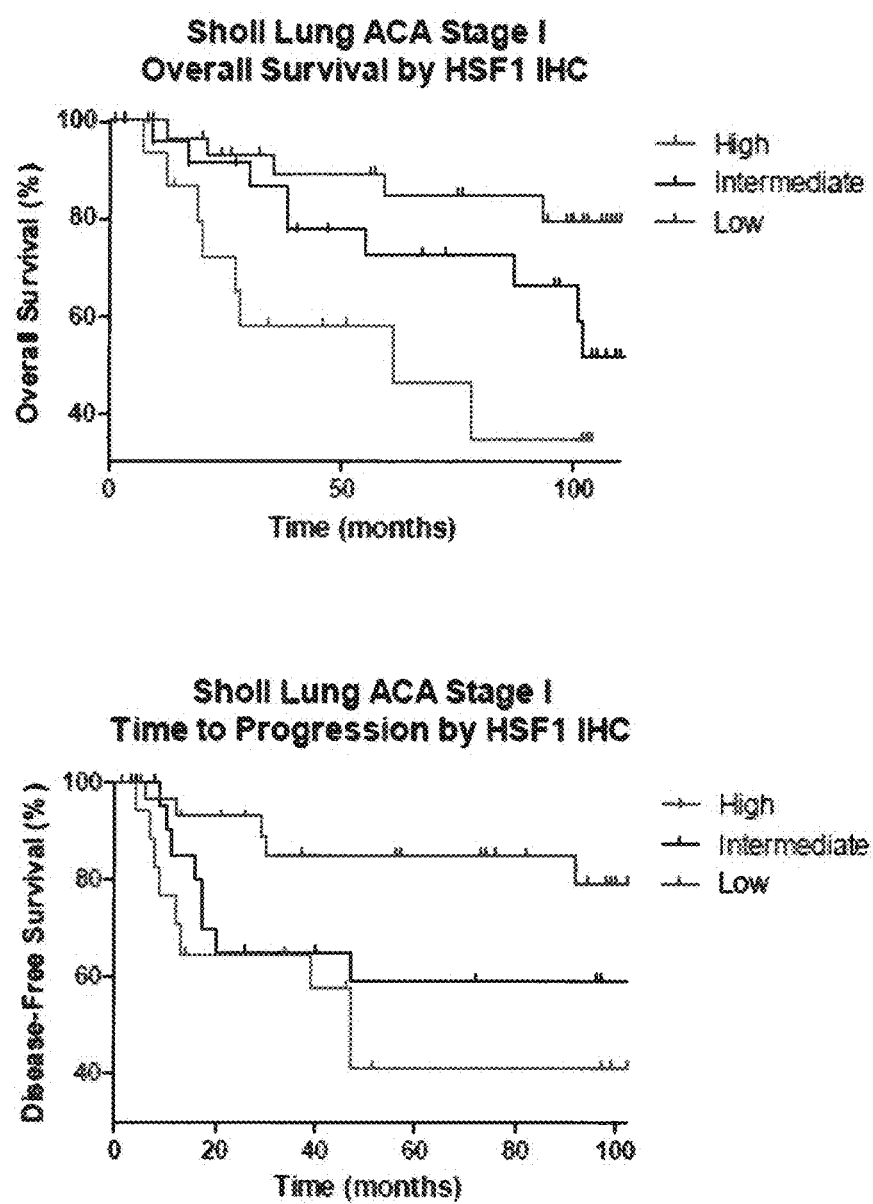
FIG. 9: HSF1 mRNA levels are associated with poor outcome in lung cancer. Kaplan-Meier analysis showing overall survival and disease free progression in a group of 70 stage I lung cancers. ACA=adenocarcinoma. (A) Panels showing KM analysis when tumors were grouped into HSF1 high, HSF1 intermediate, or HSF1 low group; (B) Panels showing KM analysis when tumors were grouped into HSF1 high/intermediate or HSF1 low group.

We performed IHC for HSF1 protein in tissue samples from a group of 70 stage I lung cancers (Stage I lung adenocarcinomas (T1 N0 M0 or T2 N0 M0)) and examined the relationship between HSF1 expression and overall survival and progression-free survival. Survival was examined by KM analysis considering HSF1-status in three categories: HSF1-low, HSF1-intermediate, and HSF1-high groups. Both overall survival and time to progression decreased as HSF1 levels increased from low to intermediate and further to high, suggesting a dose-dependent association between HSF1 activation and survival (FIG. 9A). The differences were statistically significant (P value=0.0186 for overall survival; P value=0.0314 for time to progression). When HSF1-intermediate and HSF1-high groups were combined, the difference between the HSF1-low and the HSF1-high/intermediate groups were even more evident (FIG. 9B; P value=0.0132 for overall survival; P value=0.0212 for time to progression). In FIG. 9A, the lower curve (red) is for the HSF1 high group, the middle curve (black) is for the HSF1 intermediate group, and the upper curve (blue) is for the HSF1 low group. In FIG. 9B, the lower curve (red) is for the HSF1 high/intermediate group, and the upper curve (black) is for the HSF1 low group.

REFERENCE LIST

1. Rabindran S K, Giorgi G, Clos J, & Wu C (1991) Molecular cloning and expression of a human heat shock factor, HSF1. *Proc Natl Acad Sci USA* 88(16):6906-6910.
2. Wiederrecht G, Seto D, & Parker C S (1988) Isolation of the gene encoding the *S. cerevisiae* heat shock transcription factor. *Cell* 54(6):841-853.
3. Xiao X, et al. (1999) HSF1 is required for extra-embryonic development, postnatal growth and protection during inflammatory responses in mice. *EMBO J.* 18(21):5943-5952.
4. Guertin M J & Lis J T (2010) Chromatin landscape dictates HSF binding to target DNA elements. *PLoS Genet.* 6(9).
5. Page T J, et al. (2006) Genome-wide analysis of human HSF1 signaling reveals a transcriptional program linked to cellular adaptation and survival. *Mol Biosyst* 2(12):627-639.
6. Dai C, Whitesell L, Rogers A B, & Lindquist S (2007) Heat shock factor 1 is a powerful multifaceted modifier of carcinogenesis. *Cell* 130(6):1005-1018.
7. Luo J, Solimini N L, & Elledge S J (2009) Principles of cancer therapy: oncogene and non-oncogene addiction. *Cell* 136(5):823-837.
8. Solimini N L, Luo J, & Elledge S J (2007) Non-oncogene addiction and the stress phenotype of cancer cells. *Cell* 130(6):986-988.
9. Meng L, Gabai V L, & Sherman M Y (2010) Heat-shock transcription factor HSF1 has a critical role in human epidermal growth factor receptor-2-induced cellular transformation and tumorigenesis. *Oncogene* 29(37):5204-5213.
10. Min J N, Huang L, Zimonjic D B, Moskophidis D, & Mivechi N F (2007) Selective suppression of lymphomas by functional loss of Hsf1 in a p53-deficient mouse model for spontaneous tumors. *Oncogene* 26(35):5086-5097.
11. Ciocca D R & Calderwood S K (2005) Heat shock proteins in cancer: diagnostic, prognostic, predictive, and treatment implications. *Cell Stress Chaperones* 10(2):86-103.
12. Barginear M F, et al. (2008) The heat shock protein 90 chaperone complex: an evolving therapeutic target. *Curr Cancer Drug Targets* 8(6):522-532.
13. Whitesell L & Lindquist S L (2005) HSP90 and the chaperoning of cancer. *Nat Rev Cancer* 5(10):761-772.
14. Hoang A T, et al. (2000) A novel association between the human heat shock transcription factor 1 (HSF1) and prostate adenocarcinoma. *Am J Pathol* 156(3):857-864.
15. Khaleque M A, et al. (2008) Heat shock factor 1 represses estrogen-dependent transcription through association with MTA1. *Oncogene* 27(13):1886-1893.
16. Khaleque M A, et al. (2005) Induction of heat shock proteins by heregulin beta1 leads to protection from apoptosis and anchorage-independent growth. *Oncogene* 24(43):6564-6573.
17. van de Vijver M J, et al. (2002) A gene-expression signature as a predictor of survival in breast cancer. *N Engl J Med* 347(25):1999-2009.
18. Robert F & Pelletier J (2009) Translation initiation: a critical signalling node in cancer. *Expert Opin Ther Targets* 13(11): 1279-1293.
19. Williams B R, et al. (2008) Aneuploidy affects proliferation and spontaneous immortalization in mammalian cells. *Science* 322(5902):703-709.
20. Scott K L, et al. (2011) Proinvasion metastasis drivers in early-stage melanoma are oncogenes. *Cancer Cell* 20(1):92-103.
21. Cowen L E & Lindquist S (2005) Hsp90 potentiates the rapid evolution of new traits: drug resistance in diverse fungi. *Science* 309(5744):2185-2189.
22. Michor F & Polyak K (The origins and implications of intratumor heterogeneity. *Cancer Prev Res (Phila)* 3(11):1361-1364.
23. Merlo L M, et al. (2010) A comprehensive survey of clonal diversity measures in Barrett's esophagus as biomarkers of progression to esophageal adenocarcinoma. *Cancer Prev Res (Phila)* 3(11):1388-1397.
24. Higgins M J & Stearns V (2009) Understanding resistance to tamoxifen in hormone receptor-positive breast cancer. *Clin Chem* 55(8):1453-1455.
25. Singh R R, Barnes C J, Talukder A H, Fuqua S A, & Kumar R (2005) Negative regulation of estrogen receptor alpha transactivation functions by LIM domain only 4 protein. *Cancer Res* 65(22):10594-10601.
26. Manavathi B, Singh K, & Kumar R (2007) MTA family of coregulators in nuclear receptor biology and pathology. *Nucl Recept Signal* 5:e010.
27. Kumar R, et al. (2002) A naturally occurring MTA1 variant sequesters oestrogen receptor-alpha in the cytoplasm. *Nature* 418(6898):654-657.
28. Zhao Y H, et al, (2009) Upregulation of lactate dehydrogenase A by ErbB2 through heat shock factor 1 promotes breast cancer cell glycolysis and growth. *Oncogene* 28(42):3689-3701.
29. Ince T A, et al. (2007) Transformation of different human breast epithelial cell types leads to distinct tumor phenotypes. *Cancer Cell* 12(2):160-170.
30. Calderwood S K (2010) Heat shock proteins in breast cancer progression—a suitable case for treatment? *Int J Hyperthermia* 26(7):681-685.
31. de Billy E, Powers M V, Smith J R, & Workman P (2009) Drugging the heat shock factor 1 pathway: exploitation of the critical cancer cell dependence on the guardian of the proteome. *Cell Cycle* 8(23):3806-3808.
32. Whitesell L & Lindquist S (2009) Inhibiting the transcription factor HSF1 as an anticancer strategy. *Expert Opin Ther Targets* 13(4):469-478.
33. Mayer I A (2009) Treatment of HER2-positive metastatic breast cancer following initial progression. *Clin Breast Cancer* 9 Suppl 2:S50-57.
34. Modi S, et al, (2007) Combination of trastuzumab and tanespimycin (17-AAG, KOS-953) is safe and active in trastuzumab-refractory HER-2 overexpressing breast cancer: a phase I dose-escalation study. *J Clin Oncol* 25(34):5410-5417.
35. Modi S, et al. (2011) HSP90 Inhibition is Effective in Breast Cancer: A Phase 2 Trial of Tanespimycin (17AAG) plus Trastuzumab in Patients with HER2-Positive Metastatic Breast Cancer Progressing on Trastuzumab. *Clin Cancer Res.* 17(15):5132-9.
36. Kamal A, et al. (2003) A high-affinity conformation of Hsp90 confers tumour selectivity on Hsp90 inhibitors. *Nature* 425(6956):407-410.
37. Ramanathan R K, et al. (2010) Phase I pharmacokinetic and pharmacodynamic study of 17-dimethylaminoethylamino-17-demethoxygeldanamycin, an inhibitor of heat-shock protein 90, in patients with advanced solid tumors. *J Clin Oncol* 28(9):1520-1526.

38. Trepel J, Mollapour M, Giaccone G, & Neckers L (2010) Targeting the dynamic HSP90 complex in cancer. *Nat Rev Cancer* 10(8):537-549.
39. Whitesell L, Bagatell R, & Falsey R (2003) The stress response: implications for the clinical development of hsp90 inhibitors. *Curr Cancer Drug Targets* 3(5):349-358.
40. Hu R, et al. (2011) Androgen receptor expression and breast cancer survival in postmenopausal women. *Clin Cancer Res* 17(7):1867-1874.
41. Tamimi R M, et al. (2008) Comparison of molecular phenotypes of ductal carcinoma in situ and invasive breast cancer. *Breast Cancer Res* 10(4):R67.
42. Dawood S, et al. (2011) Defining breast cancer prognosis based on molecular phenotypes: results from a large cohort study. *Breast Cancer Res Treat* 126:185-92.

\* \* \*

Those skilled in the art will recognize, or be able to ascertain using no more than routine experimentation, many equivalents to the specific embodiments of the invention described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more element(s), feature(s), or limitation(s) found in any other claim, e.g., any other claim that is dependent on the same base claim. Any one or more claims can be modified to explicitly exclude any one or more embodiment(s), element(s), feature(s), etc. For example, any particular type of tumor, tumor characteristic, for therapeutic agent, can be excluded from any one or more claims.

It should be understood that (i) any method of classification, assessment, diagnosis, prognosis, treatment-specific prediction, treatment selection, treatment, etc., can include a step of providing a sample, e.g., a sample obtained from a subject in need of classification, assessment, diagnosis, prognosis, treatment-specific prediction, treatment selection, or treatment for cancer, e.g., a tumor sample obtained from the subject; (ii) any method of classification, assessment, diagnosis, prognosis, treatment-specific prediction, treatment selection, treatment, etc., can include a step of providing a subject in need of classification, assessment, diagnosis, prognosis, treatment-specific prediction, treatment selection, or treatment for cancer.

Where the claims recite a method, certain aspects of the invention provide a product, e.g., a kit, agent, or composition, suitable for performing the method.

Where elements are presented as lists, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact. In some embodiments a request is fulfilled, e.g., a method or step is performed, in exchange for a fee or other consideration and/or pursuant to an agreement between a requestor and an individual or entity performing the method or step. It should also be understood that unless otherwise indicated or evident from the context, any product or composition described herein may be considered "isolated". It should also be understood that, where applicable, unless otherwise indicated or evident from the context, any method or step of a method that may be amenable to being performed mentally or as a mental step or using a writing implement such as a pen or pencil, and a surface suitable for writing on, such as paper, may be expressly indicated as being performed at least in part, substantially, or entirely, by a machine, e.g., a computer, device (apparatus), or system, which may, in some embodiments, be specially adapted or designed to be capable of performing such method or step or a portion thereof.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

TABLE 1

Means and frequencies of participants' characteristics by HSF1-status (N = 1841), Nurses' Health Study (1976-1996).

| Characteristic | None | Low | High |
|---|---|---|---|
| N (%) | 404 (21.9) | 882 (47.9) | 555 (30.2) |
| Age at diagnosis, mean (N), yr | 57.8 (404) | 56.8 (882) | 57.6 (555) |
| Menopausal status at diagnosis, N* (%) | | | |
| Premenopausal | 74 (18.6) | 219 (25.3) | 109 (20.2) |
| Postmenopausal | 325 (81.5) | 648 (74.7) | 432 (79.9) |
| ER status, N* (%) | | | |
| Positive | 334 (82.7) | 702 (79.4) | 412 (71.2) |
| Negative | 70 (17.3) | 182 (20.6) | 167 (28.8) |
| HER2 status, N* (%) | | | |
| Positive | 23 (5.8) | 95 (10.7) | 81 (14.1) |
| Negative | 375 (94.2) | 794 (89.3) | 494 (85.9) |
| Triple-negative tumors, N* (%) | | | |
| Yes | 49 (12.2) | 122 (13.7) | 108 (18.7) |
| No | 353 (87.8) | 766 (86.3) | 471 (81.4) |
| Nodal involvement, N (%) | | | |
| None | 290 (71.8) | 590 (66.9) | 324 (58.4) |
| 1-3 | 72 (17.8) | 166 (18.8) | 134 (24.1) |
| 4-9 | 26 (6.4) | 78 (8.8) | 55 (9.9) |
| ≥10 | 16 (4.0) | 48 (5.4) | 42 (7.6) |

TABLE 1-continued

Means and frequencies of participants' characteristics by HSF1-status (N = 1841), Nurses' Health Study (1976-1996).

| Characteristic | None | Low | High |
|---|---|---|---|
| Tumor size (cm), N (%) | | | |
| ≤2 | 301 (74.5) | 589 (66.8) | 295 (53.2) |
| >2 | 103 (25.5) | 293 (33.2) | 260 (46.9) |
| Histological grade, N* (%) | | | |
| I (low) | 143 (35.8) | 159 (18.2) | 51 (9.3) |
| II (intermediate) | 199 (49.8) | 543 (62.1) | 284 (51.7) |
| III (high) | 58 (14.5) | 173 (19.8) | 214 (39.0) |
| Stage†, N (%) | | | |
| I | 239 (59.2) | 452 (51.3) | 217 (39.1) |
| II | 114 (28.2) | 283 (32.1) | 225 (40.5) |
| III | 51 (12.6) | 147 (16.7) | 113 (20.4) |
| Chemotherapy, N* (%) | | | |
| Yes | 101 (33.2) | 263 (41.9) | 217 (50.6) |
| No | 203 (66.8) | 365 (58.1) | 212 (49.4) |
| Hormone treatment, N* (%) | | | |
| Yes | 207 (68.8) | 415 (66.3) | 280 (66.0) |
| No | 94 (31.2) | 211 (33.7) | 144 (34.0) |
| Radiation treatment, N* (%) | | | |
| Yes | 136 (44.4) | 275 (43.7) | 185 (43.3) |
| No | 170 (55.6) | 354 (56.3) | 242 (56.7) |

*N doesn't add to total because of missing information.
†Stage 1= tumor size <=2 cm and no nodal involvement;
II = tumor size <=2 cm & 1-3 nodes or 2-4cm & 0-3 nodes or 4+ cm & 0 nodes;
III = tumor size <=2 cm & 4+ nodes or 2-4cm & 4+ nodes or <4cm & 1+ nodes.

TABLE 2

Multivariate analysis of breast cancer-specific mortality by HSF1-status.

| Models | N Cases | Endpoints | Hazard Ratio (95% CI*) HSF1-negative | HSF1-positive |
|---|---|---|---|---|
| All cases: | | | | |
| Model[1] | 1841 | 463 | 1.00 | 1.74 (1.35-2.25) |
| Model[2] | 1841 | 463 | 1.00 | 1.50 (1.15-1.95) |
| ER-positive cases: | | | | |
| Model[1] | 1416 | 327 | 1.00 | 2.21 (1.60-3.06) |
| Model[3] | 1416 | 327 | 1.00 | 1.86 (1.34-2.59) |
| ER-negative cases: | | | | |
| Model[1] | 403 | 135 | 1.00 | 0.86 (0.56-1.32) |
| Model[3] | 403 | 135 | 1.00 | 0.88 (0.570-1.39) |
| HER2-positive cases: | | | | |
| Model[1] | 194 | 71 | 1.00 | 2.06 (0.83-5.12) |
| Model[2] | 194 | 71 | 1.00 | 2.87 (1.12-7.39) |
| HER2-negative cases: | | | | |
| Model[1] | 1621 | 386 | 1.00 | 1.61 (1.23-2.11) |
| Model[2] | 1621 | 386 | 1.00 | 1.37 (1.04-1.80) |
| Triple-negative cases: | | | | |
| Model[1] | 268 | 86 | 1.00 | 0.88 (0.52-1.50) |
| Model[3] | 268 | 86 | 1.00 | 0.88 (0.50-1.53) |
| ER-positive with hormone therapy cases: | | | | |
| Model[1] | 700 | 122 | 1.00 | 2.77 (1.52-5.02) |
| Model[4] | 700 | 122 | 1.00 | 2.20 (1.19-4.05) |

TABLE 2-continued

Multivariate analysis of breast cancer-specific mortality by HSF1-status.

| | N | | Hazard Ratio (95% CI*) | |
|---|---|---|---|---|
| Models | Cases | Endpoints | HSF1-negative | HSF1-positive |
| ER-positive without hormone therapy cases: | | | | |
| Model¹ | 247 | 38 | 1.00 | 3.22 (1.14-9.10) |
| Model⁴ | 247 | 38 | 1.00 | 2.01 (0.69-5.88) |

*CI denotes confidence interval.

Model¹: Adjust for age at diagnosis (years).

Model²: Adjust for age at diagnosis (years), estrogen receptor status (positive, negative), date of diagnosis (months), disease stage (I, II, III), grade (I, II, III), radiation treatment (yes, no, missing), chemotherapy and hormonal treatment (no/no, yes/no, no/yes, yes/yes, missing).

Model³: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

Model⁴: Adjust for age at diagnosis (years), date of diagnosis (months), disease stage (I, II, III), grade (I, II, III), radiation treatment (yes, no, missing) and chemotherapy (yes, no, missing).

TABLE 3

Multivariate analysis of breast cancer-specific mortality by HSF1-status.

| | N | | Hazard Ratio (95% CI) | | |
|---|---|---|---|---|---|
| Models | Cases | Endpoints | None | Low | High |
| All cases: | | | | | |
| Model¹ | 1841 | 463 | 1.00 | 1.61 (1.23-2.11) | 1.97 (1.49-2.62) |
| Model² | 1841 | 463 | 1.00 | 1.45 (1.10-1.91) | 1.62 (1.21-2.17) |
| ER-positive cases: | | | | | |
| Model¹ | 1416 | 327 | 1.00 | 1.98 (1.41-2.78) | 2.66 (1.87-3.79) |
| Model³ | 1416 | 327 | 1.00 | 1.75 (1.25-2.47) | 2.10 (1.45-3.03) |

*CI denotes confidence interval.

Model¹: Adjust for age at diagnosis (years).

Model²: Adjust for age at diagnosis (years), estrogen receptor status (positive, negative), date of diagnosis (months), disease stage (I, II, III), grade (I, II, III), radiation treatment (yes, no, missing), chemotherapy and hormonal treatment (no/no, yes/no, no/yes, yes/yes, missing).

Model³: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

TABLE 4

Multivariate analysis of breast cancer-specific mortality by HSF1-status.

| | N | | Hazard Ratio (95% CI*) | |
|---|---|---|---|---|
| Models | Cases | Endpoints | HSF1-negative | HSF1-positive |
| ER-positive, node negative cases: | | | | |
| Model¹ | 947 | 142 | 1.00 | 1.89 (1.20-2.98) |
| Model² | 947 | 142 | 1.00 | 1.59 (1.00-2.53) |

*CI denotes confidence interval.

Model¹: Adjust for age at diagnosis (years).

Model²: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

TABLE 5

Multivariate analysis of breast cancer-specific mortality by HSF1-status.

| | N | | Hazard Ratio (95% CI) | | |
|---|---|---|---|---|---|
| Models | Cases | Endpoints | None | Low | High |
| ER-positive, node negative cases: | | | | | |
| Model¹ | 947 | 142 | 1.00 | 1.65 (1.02-2.66) | 2.41 (1.45-3.99) |
| Model² | 947 | 142 | 1.00 | 1.42 (0.88-2.31) | 1.98 (1.17-3.33) |

*CI denotes confidence interval.

Model¹: Adjust for age at diagnosis (years).

Model²: Adjust for age at diagnosis (years), date of diagnosis (months), disease stage (I, II, III), grade (I, II, III), radiation treatment (yes, no, missing), chemotherapy and hormonal treatment (no/no, yes/no, no/yes, yes/yes, missing).

TABLE 6

Frequency of HSF1 expression in DCIS according to tumor grade, Nurses' Health Study (1976 to 1996). Number of cases and (%). Chi-square analysis.

| HSF1 Expression | None | Low | High | P-value |
|---|---|---|---|---|
| DCIS | | | | 0.4907 |
| DCIS, low nuclear grade | 4 (22.2) | 11 (61.1) | 3 (16.7) | |
| DCIS, intermediate grade | 16 (16.8) | 54 (56.8) | 25 (26.3) | |
| DCIS, high nuclear grade | 11 (12.6) | 46 (52.9) | 30 (34.5) | |

Chi square analysis of HSF1-negative, HSF1-low and HSF1-high: P = 0.4907.

We claim:

1. A method for treating a subject who has received local therapy for treatment for a tumor, wherein the tumor is a breast, lung, colon, prostate, cervical, pancreatic, meningeal, or nerve sheath tumor, the method comprising: treating the subject with an adjuvant therapy following said local therapy, wherein the tumor has been determined to have an increased level of nuclear HSF 1 expression relative to a control level prior to administration of the adjuvant therapy.

2. The method of claim 1, wherein the adjuvant therapy comprises adjuvant chemotherapy.

3. The method of claim 1, wherein the tumor is a carcinoma.

4. The method of claim 1, wherein the tumor is an adenocarcinoma.

5. The method of claim 1, wherein the tumor is a cancer in situ (CIS).

6. The method of claim 1, wherein the tumor is a Stage I or Stage II tumor.

7. The method of claim 1, wherein the tumor is a lung adenocarcinoma.

8. The method of claim 1, wherein the tumor is a breast tumor.

9. The method of claim 1, wherein the tumor is an estrogen receptor (ER) positive breast tumor.

10. The method of claim 1, wherein the tumor is a human epidermal growth factor 2 (HER2) positive breast tumor.

11. The method of claim 1, wherein the tumor is a lymph node negative breast tumor.

12. The method of claim 1, wherein the tumor is an estrogen receptor (ER) positive, lymph node negative breast tumor.

13. The method of claim 1, wherein the tumor has been determined to have an increased level of nuclear HSF1 expression by a method comprising measuring the level of nuclear HSF1 polypeptide in a sample from the tumor.

14. The method of claim 1, wherein the tumor has been determined to have an increased level of nuclear HSF 1 expression by a method comprising detecting nuclear HSF1 polypeptide in a sample from the tumor using an antibody that binds to nuclear HSF1 polypeptide.

15. The method of claim 1, wherein the tumor has been determined to have an increased level of nuclear HSF1 expression by a method comprising performing immunohistochemistry (IHC) on a sample from the tumor.

16. The method of claim 1, wherein the tumor has been determined to have an increased level of nuclear HSF1 expression by a method comprising determining the level of phosphorylation of nuclear HSF1 polypeptide on serine 326, wherein phosphorylation of nuclear HSF1 polypeptide on serine 326 is indicative of nuclear HSF1 activation.

17. The method of claim 1, wherein the adjuvant therapy is administered at a time when the tumor appears to have been completely eradicated by said local therapy.

\* \* \* \* \*